US010669543B2

(12) United States Patent
Hong et al.

(10) Patent No.: US 10,669,543 B2
(45) Date of Patent: Jun. 2, 2020

(54) METHODS TO PREVENT OR TREAT PERIODONTITIS OR PERI-IMPLANTITIS

(71) Applicant: University of Iowa Research Foundation, Iowa City, IA (US)

(72) Inventors: Liu Hong, Coralville, IA (US); Brad A. Amendt, Solon, IA (US); Aliasger K. Salem, Coralville, IA (US); Satheesh Elangovan, Iowa City, IA (US); Gustavo Avila Ortiz, Iowa City, IA (US); Thad Sharp, Chapel Hill, NC (US)

(73) Assignee: University of Iowa Research Foundation, Iowa City, FL (US)

( * ) Notice: Subject to any disclaimer, the term of this patent is extended or adjusted under 35 U.S.C. 154(b) by 0 days.

(21) Appl. No.: 15/543,816

(22) PCT Filed: Jan. 15, 2016

(86) PCT No.: PCT/US2016/013695
§ 371 (c)(1),
(2) Date: Jul. 14, 2017

(87) PCT Pub. No.: WO2016/115516
PCT Pub. Date: Jul. 21, 2016

(65) Prior Publication Data
US 2019/0144856 A1 May 16, 2019

Related U.S. Application Data

(60) Provisional application No. 62/117,254, filed on Feb. 17, 2015, provisional application No. 62/104,465, filed on Jan. 16, 2015.

(51) Int. Cl.
*C12N 15/113* (2010.01)
*A61P 19/04* (2006.01)
*A61P 19/02* (2006.01)
*A61K 47/34* (2017.01)
*A61K 47/14* (2017.01)
*A61K 47/18* (2017.01)

(52) U.S. Cl.
CPC ............ *C12N 15/113* (2013.01); *A61K 47/14* (2013.01); *A61K 47/18* (2013.01); *A61K 47/34* (2013.01); *A61P 19/02* (2018.01); *A61P 19/04* (2018.01); *C12N 2310/141* (2013.01); *C12N 2330/10* (2013.01)

(58) Field of Classification Search
None
See application file for complete search history.

(56) References Cited

U.S. PATENT DOCUMENTS

| 10,273,476 B2* | 4/2019 | Hong ................... C12N 15/113 |
| 2004/0143017 A1 | 7/2004 | Manning et al. |
| 2010/0105762 A1 | 4/2010 | Morishita et al. |
| 2011/0112654 A1 | 5/2011 | Faldt |
| 2012/0190651 A1 | 7/2012 | Pari et al. |
| 2013/0243876 A1 | 9/2013 | Mcdonald et al. |
| 2015/0125517 A1* | 5/2015 | McDonald ............... A61K 9/00 424/450 |
| 2017/0314020 A1 | 11/2017 | Hong et al. |

FOREIGN PATENT DOCUMENTS

| CN | 103405787 | 11/2013 | |
| WO | WO-2012020308 A2 | 2/2012 | |
| WO | 2012175357 | 12/2012 | |
| WO | WO-2015020769 A2 * | 2/2015 | ........... C12N 15/111 |
| WO | WO-2016115516 A1 | 7/2016 | |
| WO | WO-2016115516 A8 | 7/2016 | |

OTHER PUBLICATIONS

"International Application Serial No. PCT/US2016/013695, International Search Report dated Apr. 29, 2016", 3 pgs.
"International Application Serial No. PCT/US2016/013695, Written Opinion dated Apr. 29, 2016", 3 pgs.
Cochran, "Inflammation and Bone Loss in Periodontal Disease", J Periodontal, col. 79, No. 8, (Aug. 2008), 1569-1576.
Lacey, et al. "Proinflammatory Cytokines Inhibit Osteogenic Differentiation from Stem Cells: Implications for Bone Repair During Inflammation", Osteoarthritis and Cartilage, vol. 17, (2009), 735-742.
Wendlandt, et al., "The role of MicroRNAs miR-200b and miR-200c in TLR4 signaling and NF-iB activation", Innate Immunity, vol. 18, No. 6, (2012), 846-855.
"European Application Serial No. 16738004.7, Response filed Dec. 11, 2017 to Communicaiton Pursuant to Rules 161(2) and 162 EPC dated Aug. 31, 2017", 7 pgs.
"European Application Serial No. 16738004.7, Extended European Search Report dated Oct. 9, 2018", 5 pgs.
"European Application Serial No. 16738004.7, Response filed May 3, 2019 to Extended European Search Report dated Oct. 9, 2018", 8 pgs.
"European Application Serial No. 16738004.7, Partial Supplementary European Search Report dated Jul. 3, 2018", 15 pgs.
Database WPI Week 201425 Thomson Scientific. London. GB; AN 2014-B65239, 2 pgs.
Cao, H, "The Pitx2:miR-200c 141:noggin pathway regulates Bmp signaling and ameloblast differentiation", Development. vol. 140. No. 16, (Jul. 17, 2013), 3348-3359.
Liu, Qin, "Targeted delivery of miR-200c DOC to inhibit cancer stem cells and cancer cells by the gelatinases-stimuli nanoparticles", Biomaterials. Elsevier Science Publishers BV. Barking. GB.vol. 34. No. 29, (Jun. 24, 2013), 7191-7203.

(Continued)

*Primary Examiner* — Sean McGarry
(74) *Attorney, Agent, or Firm* — Schwegman Lundberg & Woessner, P.A.

(57) ABSTRACT

Compositions and methods to prevent, inhibit or treat aveolar or periodontal bone loss, enhance bone regeneration, prevent, inhibit or treat peri-implantitis or periodontitis, e.g., periodontitis or peri-implantitis associated with bone loss, or to prevent, inhibit or treat osteoarthritis are provided.

17 Claims, 32 Drawing Sheets

Specification includes a Sequence Listing.

(56) References Cited

OTHER PUBLICATIONS

Qiu, Weimin, "miR-141-3p inhibits human stromal (mesenchymal) stem cell proliferation and differentiation", Biochimica et Biophysica Acta. Molecular Cell Research . vol. 1843. No. 9., (Sep. 1, 2014), 2114-2121.
Zhou, Q, "Ibandronate promotes osteogenic differentiation of periodontal ligament stem cells by regulating the expression of microRNA", Biochemical and Biophysical Research Communications. Elsevier. Amsterdam. NL. vol. 404. No. 1, (Jan. 7, 2011), 127-132.
"European Application Serial No. 16738004.7, Response filed Nov. 27, 2019 to Communication Pursuant to Article 94(3) EPC dated Jul. 19, 2019", 78 pgs.
Humphries, Brock, et al,, "The microRNA-200 family: small molecules with novel roles in cancer development, progression and therapy", Oncotarget, www.impactjournals.com/oncotarget/, vol. 6, No. 9, published Jan. 30, 2015., 27 pgs.
Korpal, Manav, et al., "The miR-200 Family Inhibits Epithelial-Mesenchymal Transition and Cancer Cell Migration by Direct Targeting of E-cadherin Transcriptional Repressors ZEB1 and ZEB2", Accelerated Publication, The Journal of Biological Chemistry, v. 283, No. 22, May 30, 2008., pp. 14910-14914.

\* cited by examiner

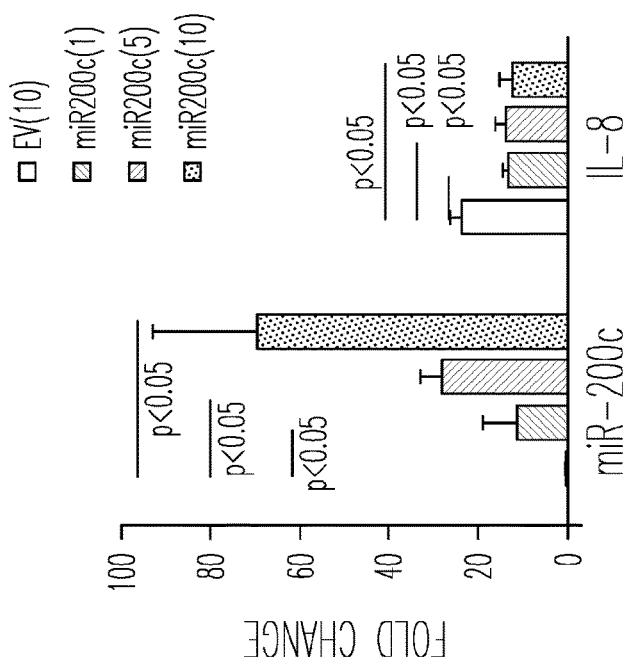
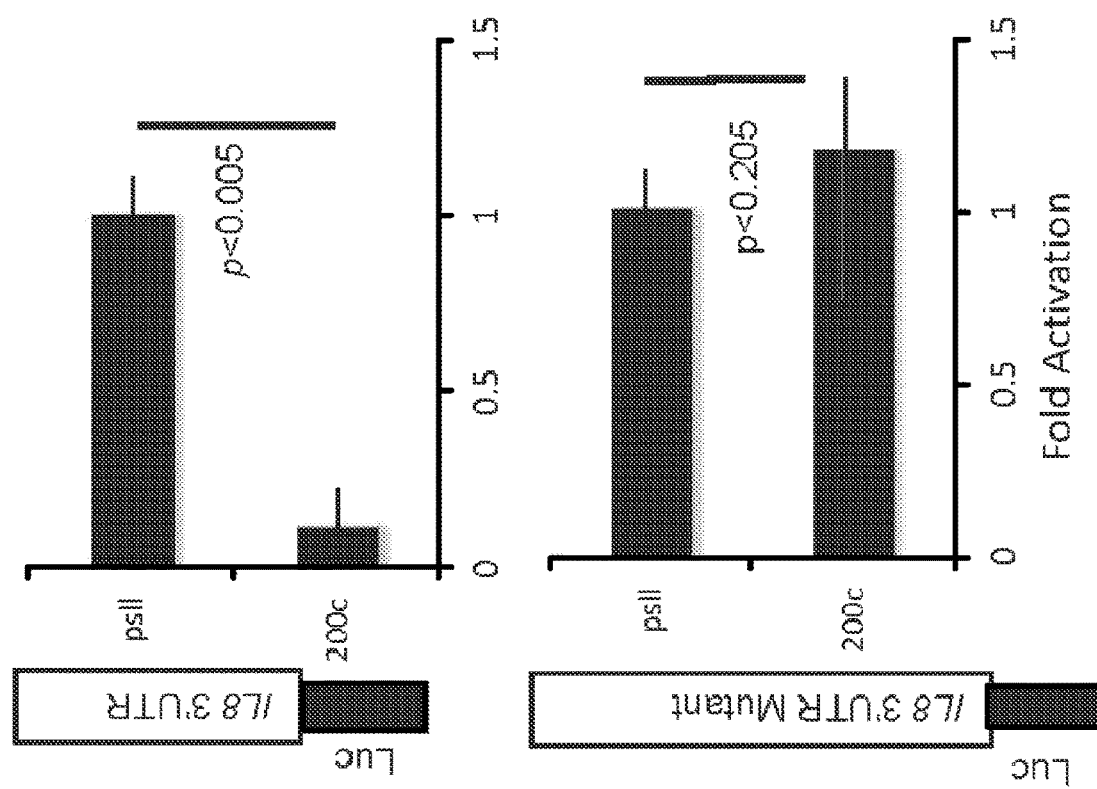
Fig. 1C
Fig. 1D

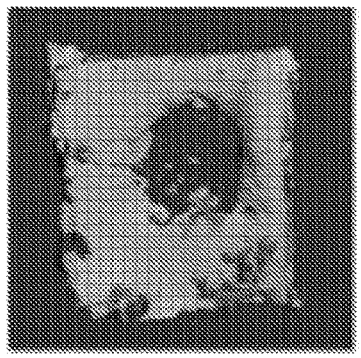 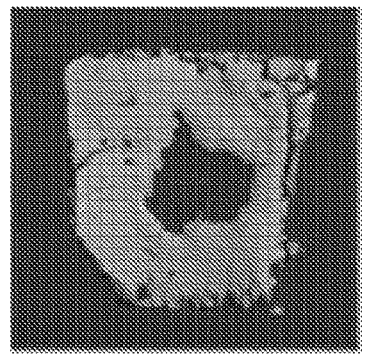 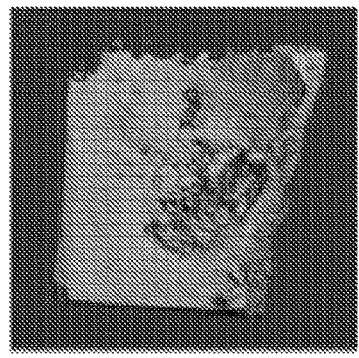
*Fig. 9A*      *Fig. 9B*      *Fig. 9C*
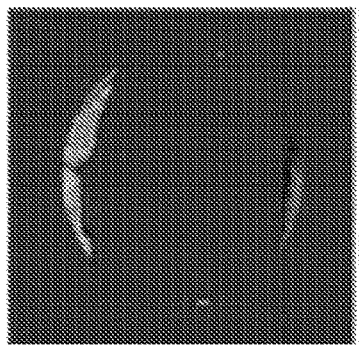 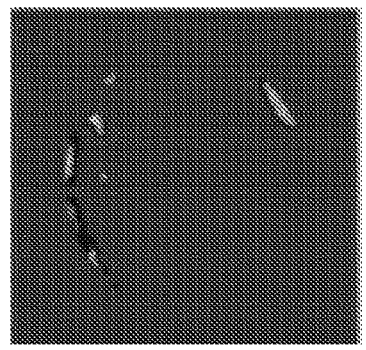 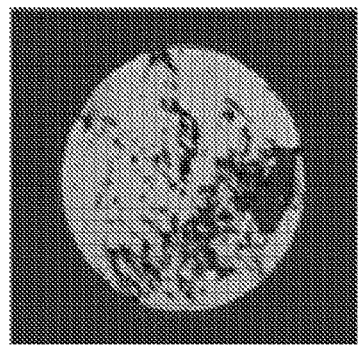
*Fig. 9D*      *Fig. 9E*      *Fig. 9F*

Has-miR-200c-3p  UAAUACUGCCGGGUAAUGAUGGA

IL-6 3'UTR   5'-TACCACTTGAAACATTTTATGTATTAG-3'          IL-6 Mut 3'UTR   5'-TTTATGTAACTGGTATCTATATTTTAA-3'
                    ||||||||||||||||
             AGGUAGUAAUGGGCCGGUCAUAAU

IL-8 3'UTR   5'-TTTATTTCTAAGTGGAAAAGTATAG-3'            IL-8 Mut 3'UTR   5'-TTCTAAGTGGAAAACTCGTAGCCA-3'
                    ||||||||||||||||
             AGGUAGUAAUGGGCCGGUCAUAAU

CCL5 3'UTR   5'-ATCTCTACTAAAATACAAAAATTAG-3'            CCL-6 Mut 3'UTR   5'-ACTCCTTCAGTACAACAACAACAA-3'
                    ||||||||||||||||
             AGGUAGUAAUGGGCCGGUCAUAAU

*Fig. 14A*

METHODS TO PREVENT OR TREAT PERIODONTITIS OR PERI-IMPLANTITIS

CROSS-REFERENCE TO RELATED APPLICATIONS

This application is a U.S. National Stage Filing under 35 U.S.C. 371 from International Application No. PCT/US2016/013695, filed on Jan. 15, 2016, and published as WO2016/115516 on Jul. 12, 2016, which claims the benefit of the filing date of U.S. application Ser. No. 62/104,465, filed on Jan. 16, 2015 and U.S. application Ser. No. 62/117,254, filed on Feb. 17, 2015; which applications and publication are incorporated herein by reference in their entirety.

GOVERNMENT GRANT SUPPORT

This invention was made with government support under grants DE024799 and DE13941 awarded by the National Institutes of Health. The Government has certain rights in the invention.

BACKGROUND

It has been reported that approximately half of American adults aged 30 years and older have periodontitis, and the prevalence of periodontitis further increase in aged populations and in patients with diabetes or that smoke (Eke et al., 2012; Papapanou and Tonetti, 2000). Approximately 50% of periodontitis patients aged 30 years and older have alveolar bone loss that eventually may lead to tooth loss and osseointegration failure of dental implants if patients do not receive efficient therapeutics to arrest the progression of this chronic disease (Papapanou and Tonetti, 2000). Although anti-resorptive and anabolic agents, including vitamin D, calcium, hormone replacements, and bisphosphonates, are currently used to prevent and treat systemic osteoporosis, the efficacy of these treatments in arresting periodontal bone loss and improving osseointegration of dental implants has not been confirmed (Armas et al., 2013; Jeffcoat, 1998; Sidiropoulou-Chatzigiannis, 2007). Long-term use of intravenous bisphosphonates has been shown to cause osteonecrosis of jaws (Khosla et al., 2012).

While bacteria derived factors initiate periodontitis, there is strong evidence that the majority of periodontitis occurs due to activation of host-derived immune and inflammatory defense mechanisms. Toll-like receptors (TLRs) are the major cell-surface initiators of inflammatory responses to pathogens. TLR-2 and TLR-4 have been demonstrated to play critical roles in recognizing periodontal pathogens and trigger the up-regulation of interleukin (IL)-6, IL-1β, and tumor necrosis factor (TNF)-α in periodontitis (Darveau, 2010; DiBenedetto et al., 2013). TLR-mediated signaling pathways also lead to activation of nuclear factor kappa-light-chain-enhancer of activated B cells (NF-κB), a key proinflammatory transcription factor (Herath at al., 2013). These cytokines and transcription factors in turn further amplify the inflammatory response and lead to production of lytic enzymes and stimulate the production of chemokines, including IL-6, IL-8 and CCL-5 (Darveau et al., Di Benedetto at al., 2013; Kajishengallis et al., 2012). Eventually, a cascade of events leads to osteoclastogenesis and subsequent bone resorption via the receptor activator of nuclear factor kappa-B ligand (RANKL)-osteoprotegerin (OPG) axis. Thus, imbalance and dysregulation of proinflammatory molecules and cytokine networks play essential roles in the process of periodontitis and associated bone resorption (Darveau, 2010; Di Benedetto at al., 2013). Reducing the expression and activation of proinflammatory and bone metabolism mediators that activate osteoclastogenesis and bone resorption may serve as an effective strategy for preventing and arresting the development of periodontal bone loss. In addition, proinflammatory mediators have been demonstrated to impair bone formation by reducing differentiation of osteoblasts and their progenitor cells (Yang et al., 2013; Lacey et al., 2009; Hikiji et al., 2000; Wang et al., 2012). Specifically, TNF-α and IL-1β have been demonstrated to inhibit osteogenic differentiation of bone marrow stem cells. TNF-α also have been reported to inhibit Osterix expression and promote degradation of Runx2. TNF-α and IL-17 activate IκB kinase (IKK)—NF-κB to reduce osteogenic differentiation of MSCs by promoting β-catenin degradation and impair bone formation. Thus, inhibiting proinflammatory mediators may prevent and restore periodontitis-associated bone loss by increasing osteogenic differentiation and bone formation.

SUMMARY

As described herein, miR-200c was transduced into a human embryonic palatal mesenchyme (HEPM) cell line (preosteoblast). Although the resulting miR-200c overexpression did not significantly affect the proliferation, it increased osteogenic differentiation biomarkers (osteocalcin (OCN) transcripts and calcium content). miR-200c expression also down-regulated interleukin (IL)-6, IL-8, and chemokine (C-C motif) ligand (CCL)-5 under lipopolysaccharide (LPS) stimulation and increased osteoprotegerin (OPG) in these cells. miR-200c directly regulates the expression of IL-6, IL-8 and CCL-5 transcripts by binding to their 3'UTRs. In addition, using polyethylenimine (PEI) nanoparticle delivery of miR-200c effectively inhibits IL-6, IL8 and CCL-5 in human primary periodontal ligament fibroblasts and increases the osteogenic differentiation biomarkers in human bone marrow mesenchymal stem cells (MSCs), including calcium content, ALP, and Runx2. These data demonstrate that miR-200c directly targets and represses IL-6, IL-8 and CCL-5 and improves osteogenic differentiation and increases OPG expression. The application of this miR may be an effective means of arresting inflammation and osteoclastogenesis, to prevent and restore periodontitis-associated bone loss.

The present invention thus provides compositions comprising one or more distinct miRNAs that modulate one or more proinflammatory cytokines, modulate osteoblastic and/or osteoclastic differentiation, modulate mesenchymal-to-epithelial transition, or a combination thereof. Also provided are methods of using miRNAs, e.g., from the miRNA 200 family, for instance, miR-200c, to suppress over-produced inflammatory cytokines and/or proinflammatory factors and/or to improve or maintain osteochondrogenic differentiation in mammals, thereby preventing inflammation-associated bone loss and joint degeneration and/or restoring bone or joints. In one embodiment, a composition having miR-200c is delivered using a delivery vehicle, e.g., a PLGA nanoparticle system or other non-viral gene delivery system, into human cells to prevent periodontitis and/or peri-implantitis associated oral bone loss. In one embodiment, the composition is useful to prevent systemic bone loss, including osteoporosis, and/or improve bone regeneration. In another embodiment, the composition may be useful to prevent and/or inhibit the progression of osteoarthritis, e.g., in orthopedic or dental patients.

The invention provides a method to prevent, inhibit or treat aveolar or periodontal bone loss. The method includes administering to a mammal an effective amount of a composition comprising isolated miRNA of one or more members of miR-200 family. In one embodiment, the mammal is a human, bovine, ovine, caprine, equine, porcine, canine or feline. In one embodiment, the amount is effective to enhance osseointegration of a dental implant. In one embodiment, the amount is effective to enhance alveolar bone regeneration. In one embodiment, the mammal is a diabetic or has hypertension. In one embodiment, the amount is effective to promote osteogenic differentiation. In one embodiment, the amount is effective to modulate or inhibit one or more proinflammatory cytokine. In one embodiment, the cytokine is IL-8 or IL-6. In one embodiment, the amount modulates osteoprotegerin (OPG) expression. In one embodiment, the composition comprises complexes of the isolated miRNA of one or more members of the miR-200 family and a carrier. In one embodiment, the carrier comprises PEI or PLGA. In one embodiment, one miR-200 family member comprises miR-200c, miR-200a, miR-200b, miR-141 or miR-429. In one embodiment, the amount is effective to inhibit cartilage degeneration.

The invention provides a method to enhance bone regeneration. The method includes administering to a mammal an effective amount of a composition comprising isolated miRNA of one or more members of miR-200 family. In one embodiment, the mammal is a human, bovine, ovine, caprine, equine, porcine, canine or feline. In one embodiment, the amount is effective to enhance osseointegration of a dental implant. In one embodiment, the amount is effective to enhance alveolar bone regeneration. In one embodiment, the mammal is a diabetic or has hypertension. In one embodiment, the amount is effective to promote osteogenic differentiation. In one embodiment, the amount is effective to modulate or inhibit one or more proinflammatory cytokine. In one embodiment, the cytokine is IL-8 or IL-6. In one embodiment, the amount modulates osteoprotegerin (OPG) expression. In one embodiment, the composition comprises complexes of the isolated miRNA of one or more members of the miR-200 family and a carrier. In one embodiment, the carrier comprises PEI or PLGA. In one embodiment, one miR-200 family member comprises miR-200c, miR-200a, miR-200b, miR-141 or miR-429. In one embodiment, the amount is effective to inhibit cartilage degeneration.

The invention provides a method to prevent, inhibit or treat peri-implantitis or periodontitis. The method includes administering to a mammal an effective amount of a composition comprising isolated miRNA of one or more members of miR-200 family. In one embodiment, the mammal is a human, bovine, ovine, caprine, equine, porcine, canine or feline. In one embodiment, the amount is effective to enhance osseointegration of a dental implant. In one embodiment, the amount is effective to enhance alveolar bone regeneration. In one embodiment, the mammal is a diabetic or has hypertension. In one embodiment, the amount is effective to promote osteogenic differentiation. In one embodiment, the amount is effective to modulate or inhibit one or more proinflammatory cytokine. In one embodiment, the cytokine is IL-8 or IL-6. In one embodiment, the amount modulates osteoprotegerin (OPG) expression. In one embodiment, the composition comprises complexes of the isolated miRNA of one or more members of the miR-200 family and a carrier. In one embodiment, the carrier comprises PEI or PLGA. In one embodiment, one miR-200 family member comprises miR-200c, miR-200a, miR-200b, miR-141 or miR-429. In one embodiment, the amount is effective to inhibit cartilage degeneration.

The invention provides a method to prevent, inhibit or treat osteoarthritis administering to a mammal an effective amount of a composition comprising isolated miRNA of one or more members of miR-200 family. In one embodiment, the mammal is a human, bovine, ovine, caprine, equine, porcine, canine or feline. In one embodiment, the amount is effective to enhance osseointegration of a dental implant. In one embodiment, the amount is effective to enhance alveolar bone regeneration. In one embodiment, the mammal is a diabetic or has hypertension. In one embodiment, the amount is effective to promote osteogenic differentiation. In one embodiment, the amount is effective to modulate or inhibit one or more proinflammatory cytokine. In one embodiment, the cytokine is IL-8 or IL-6. In one embodiment, the amount modulates osteoprotegerin (OPG) expression. In one embodiment, the composition comprises complexes of the isolated miRNA of one or more members of the miR-200 family and a carrier. In one embodiment, the carrier comprises PEI or PLGA. In one embodiment, one miR-200 family member comprises miR-200c, miR-200a, miR-200b, miR-141 or miR-429. In one embodiment, the amount is effective to inhibit cartilage degeneration.

The invention provides pharmaceutical compositions comprising isolated miRNA that modulates one or more proinflammatory cytokines, modulates osteoblastic and/or osteoclastic differentiation, modulates mesenchymal-to-epithelial transition, or a combination thereof. In one embodiment, the composition comprises a carrier. In one embodiment, the composition comprises a nucleic acid sequence with at least 60%, 65%, 70%, 75%, 80%, 85%, 90%, 92%, 93%, 94%, 95%, 96%, 97%, 98% or 99%, nucleic acid sequence identity to one of SEQ ID Nos. 1-3.

DETAILED DESCRIPTION

Definitions

Figure 1A:
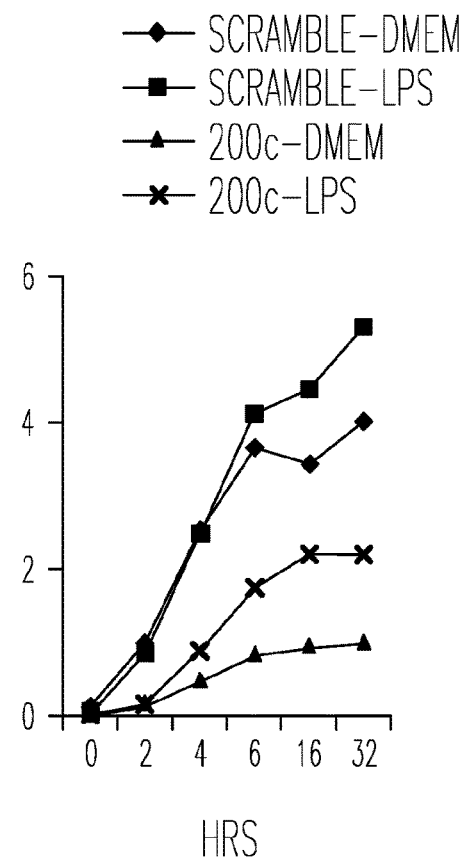
FIG. 1. miR-200c reduces IL-8 and improves OPG in human preosteoblasts. A) the amounts of IL-8 secreted by HEPM cells with miR-200c or scrambled miRs cultured in DMEM supplemented with or without LPS at different time points; B) the amounts of OPG secreted by HEPM cells with different miRs cultured in DMEM supplemented with or without LPS after 32 hours. Scramble-DMEM: cells with scrambled miRs in DMEM; 200c-DMEM: cells with miR-200c in DMEM; scramble-LPS: cells with scrambled miRs in medium supplemented with LPS; 200c-LPS: cells with miR-200c in medium with LPS. C) Normalized luciferase activities of the 3' UTR IL-8-luciferase reporters and IL-8 3'UTR-mutated-luciferase reporters treated with empty vector (psII) or miR-200c. D) Fold change of miR-200c and IL-8 mRNA in human periodontal cells transfected with empty vector (EV at 10 ug) and miR-200c (at 1, 5 and 10 ug) 24 hours after LPS stimulation.

As used herein, the term "isolated" refers to in vitro preparation and/or isolation of a nucleic acid molecule, e.g., a vector or plasmid, so that it is not associated with in vivo substances, or is substantially purified from in vitro substances.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Exemplary Inflammatory-Based Bone and Joint Disorders

It has been reported that 47.2% of 3,742 American adults aged 30 years and older have periodontitis: 8.7% had mild periodontitis, 30.0% had moderate periodontitis, and 8.5% had severe periodontitis. The prevalence further increase in aged populations and the patients with diabetes or smokers. Approximately 50% of periodontitis patients aged 30 years and older have been reported to have alveolar bone loss that may lead to tooth loss and osseointegration failure of dental implants. Although anti-resorptive and anabolic agents, including vitamin D, calcium, hormone replacements, and bisphosphonates, are currently used to prevent and treat systemic osteoporosis, the efficacy of these treatments in arresting periodontal bone loss and improving osseointegration of dental implants has not been confirmed. Long-term use of intravenous bisphosphonates has been shown to cause osteonecrosis of jaws.

While plaque bacteria and/or dental implants initiate and drive acute and chronic inflammatory responses in periodontal tissues, there is strong evidence that the majority of periodontitis and peri-implantitis occurs mainly as a result of activation of host-derived immune and inflammatory defense mechanism. Imbalance and dysregulation of proinflammatory molecules and cytokine networks play essential roles in the process of periodontitis and associated bone resorption. Proinflammatory factors, including IL-1, TNF-alpha, and NFkB induce expression of other mediators that amplify the inflammatory response and lead to production of lytic enzymes and stimulate the production of chemokines. Therefore, inhibition of host response pathways that mimic endogenous anti-inflammatory mechanisms may prove to be an effective strategy for treating periodontal diseases, which prevents periodontitis and peri-implantitis-associated bone loss. Further, reducing the expression and activation of proinflammatory cytokines and bone metabolism mediators that induce osteoclastogenesis and bone resorption may serve as an effective strategy for preventing and arresting the development of perio-dontal bone loss.

It has been reported that in 2005, nearly 27 million adults—more than 10% of the U.S. adult population—had clinical osteoarthritis (OA), a disease affecting the entire joint including the cartilage, joint lining, ligaments, and underlying bone. The breakdown of these tissues eventually leads to pain and joint stiffness. The joints most commonly affected are the knees, hips, and those in the hands and spine. In dentistry, OA majorly causes temporomandibular joint (TMJ) disorders. Current treatment for OA focuses on relieving symptoms and im-proving function, including a combination of patient education, physical therapy, weight control, and analgesic medications. However, these treatments have limited effects to slow the procession of OA disease. OA is the leading indication for joint replacement surgery. In 2009, 905,000 knee and hip replacements were performed in US at a cost of $42.3 billion. Thus, new medications both to alleviate pain and slow disease progression are needed.

Although the specific causes of OA are unknown, it has been believed that inflammation of the synovial membrane is one of the main contributors to cartilage matrix destruction. Macrophages in the synovial membrane of OA joints play a pivotal role in cartilage matrix degradation by releasing cytokines such as IL-1β and TNF, as well as pro-matrix metalloproteinases (pro-MMPs). These cytokines further activate inflammation by up-regulating a complex mixture of inflammatory and proinflammatory cytokines in synovial cells and chondrocytes, including TNFα, IL-1β, IL-6, IL-8, and IFN-γ, which eventually drive the catabolic process in the entire joint by stimulating the production of catalytic enzymes, lipid mediators, nitric oxide, and free radicals. In addition, the OA-associated proinflammatory cytokines impact cartilage repair mechanisms and affect the subchondral bone in the zone of calcified cartilage. Therefore, targeting inflammation of synovial membrane and controlling proinflammatory cytokines have been considered as a promising approach for OA treatment. Since the cytokines also contribute to peripheral and central pain transmission, reducing the proinflammatory molecules of cartilage breakdown may relieve pain in OA patients.

Exemplary Biological Modulators of Inflammation microRNAs (miRs), non-coding small RNAs, actively participate in inflammatory regulation by directly degrading and/or silencing the transcription of targeted genes (Singh et al., 2013; Plank et al., 2013). miRs also have been demonstrated to regulate osteogenic differentiation and bone homeostasis (Lian et al., 2012). miR-200c, a member of the miR-200 family can regulate the mesenchymal-to-epithelial transition (MTE) (Katoh and Katoh, 2008), and is significantly underexpressed in gingival tissues of periodontitis patients (Stoecklin-Wasmer et al., 2012). miR-200c also participates in stem cell proliferation and differentiation (Huang et al., 2014). miR-200c is also involved in signal pathways mediated by multiple proinflammatory factors and repress the expression and activity of NF-kB (Rokavec et al., 2012; Wendlandt et al., 2012; Howe et al., 2012). In addition, miR-200c was found to effectively inhibit Noggin, an antagonist of BMP signals, by directly targeting the 3'UTR of Noggin (Cao et al., 2013). This evidence strongly suggested that miR-200c may possess the molecular function to both improve osteogenic differentiation and modulate periodontitis-associated proinflammatory mediators.

MicroRNAs (miRs) actively participate in inflammatory regulation, including periodontitis, by modulating the expression of target genes. A recent study reported that 159 miRs were significantly differentially expressed between healthy and periodontitis gingiva in a total of 89 individuals. Of these, 91 were overexpressed and 68 were underexpressed in diseased versus healthy gingiva. miRs also regulate osteogenic differentiation and bone homeostasis. Therefore, by understanding the molecular function and underlying mechanisms of miRs on inhibiting proinflammatory cytokines and bone resorption factors and improving osteogenic capabilities, compositions are developed to effectively prevent, arrest, and/or restore periodontitis-associated alveolar bone loss using specific miRs. Moreover, miRs participate in the regulation of inflammation and pathophysiology of OA. By identifying specific miRs that can effectively repress OA-accelerating proinflammatory cytokines and modulate bone/cartilage metabolism mediators, an efficient therapeutics for OA that control synovial inflammation and chondrocyte differentiation are identified.

MicroRNA (miR)-200c is a member of the miR-200 family that is involved in regulation of mesenchymal-to-epithelial transition (MTE). miR-200c is significantly underexpressed in gingival tissues of periodontitis patients. miR-200c was found to regulate signal pathways mediated by multiple proinflammatory factors and repress the expression and activity of NF-kB. This evidence suggested that miR-200c may both improve osteogenic differentiation and repress the activation of proinflammatory molecules. Preliminary studies showed that overexpression of miR-200c effectively reduces IL-6 and IL-8 in human primary cells (see FIGS. 1-2 and 4). This evidence suggested that miR-200c may be used to prevent and inhibit cartilage degeneration in OA by repressing OA-associated proinflammatory molecules. As described I more detail below, in vitro data demonstrates that miR-200c can reduce multiple proinflammatory cytokines and improve osteogenic differentiation. Also, in vivo data show miR-200c delivered using PEI nanoparticles improves bone regeneration. Thus, the compositions may also inhibit bone loss and/or cartilage degeneration. Thus, miRNAs are capable of silencing the expression of target genes via base-pairing with complementary sequences within mRNA molecules, and these small molecules actively participate in inflammatory regulation and the differentiation of osteoblasts and their progenitor cells. Therefore, the action of these molecules may be utilized to prevent the bone loss and/or cartilage degeneration induced by chronic inflammatory diseases.

Exemplary Methods

Proinflammatory and bone metabolism mediators have been demonstrated to play critical roles in the development of periodontitis-associated bone loss by activating osteoclastogenesis and impairing bone formation. Thus, modulating the proinflammatory and bone metabolism mediators and promoting osteogenic differentiation may serve as an effective strategy to arrest and restore the bone loss.

MicroRNAs (miRs) are small non-coding RNAs which have anti-inflammatory functions via modulating activities and expressions of proinflammatory cytokines. miRs also participate in bone homeostasis by modulating osteoblastic and osteoclastic differentiation. The present invention provides a miR-based approach that can effectively arrest inflammation-induced periodontal bone loss and/or enhance bone regeneration. Specifically, a member of miR-200 family was identified that can effectively inhibit multiple proinflammatory cytokines in human primary oral cells. Overexpression of this miR also potentially improves osteogenic differentiation and bone formation. Thus, miR can be used to arrest and restore periodontal bone loss by inhibiting inflammation and improving osteogenesis.

In one embodiment, the invention employs mir-200c to suppress over-produced inflammatory cytokines and proinflammatory factors in periodontitis and/or peri-implantitis patients, thereby preventing periodontal disease-associated alveolar bone loss and osseointegration failure. Mir-200c may be delivered into human cells using a carrier such as in complexes with PEI or a PLGA nanoparticle system, or other non-viral gene delivery system. In one embodiment, mir-200 may be employed prevent periodontitis and peri-implantitis associated oral bone loss. In one embodiment, mir-200 may be employed prevent or inhibit systemic bone loss, e.g., prevent or inhibit osteoporosis and/or improve bone formation.

Figure 4:
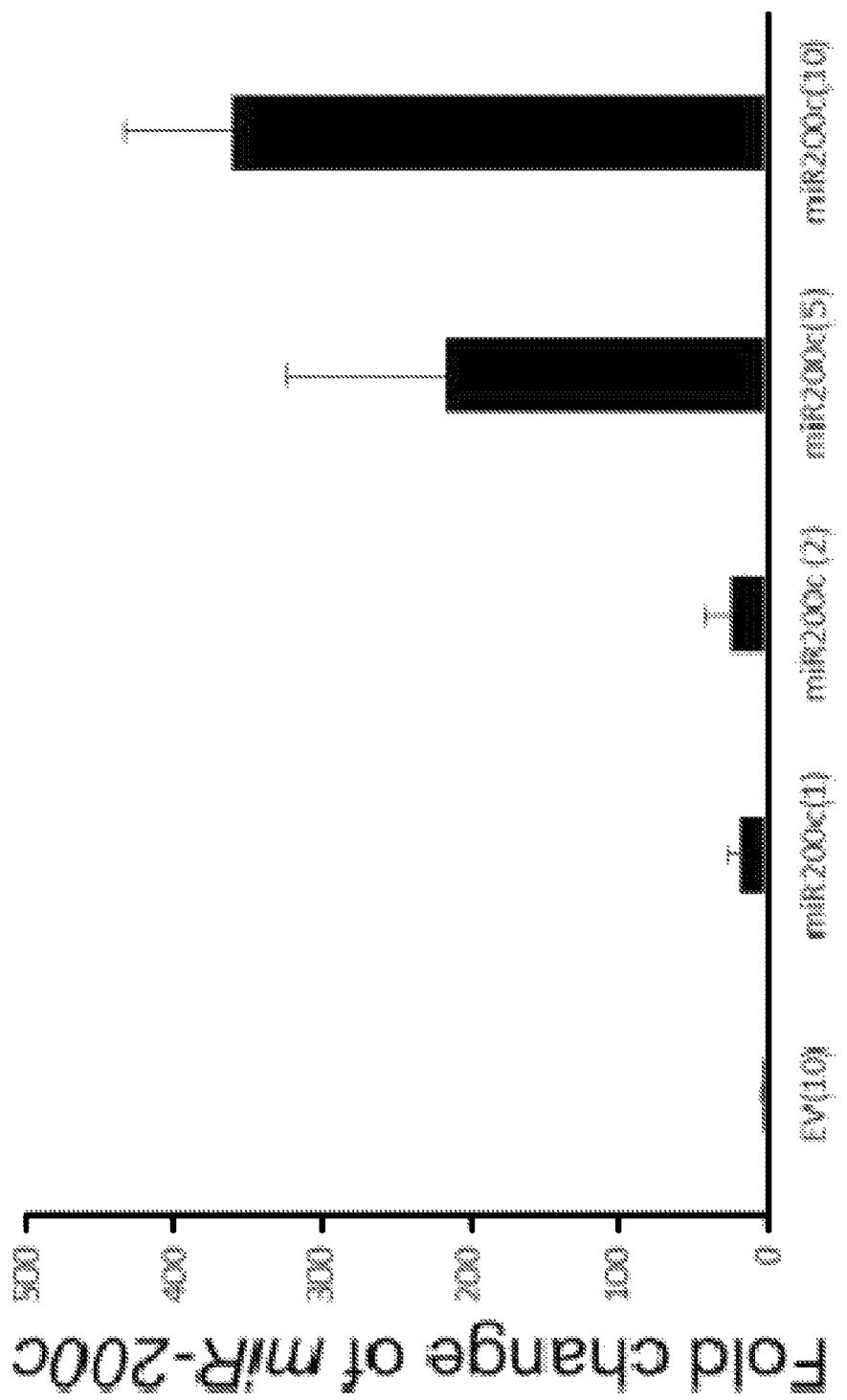
FIG. 4. mRNA expression of miR-200c in human MSCs one week after treatment with PEI nanoparticles incorporating empty vector (EV) at 10 μg or miR-200c at 1, 2, 5 and 10 μg, respectively.
Figure 5A:
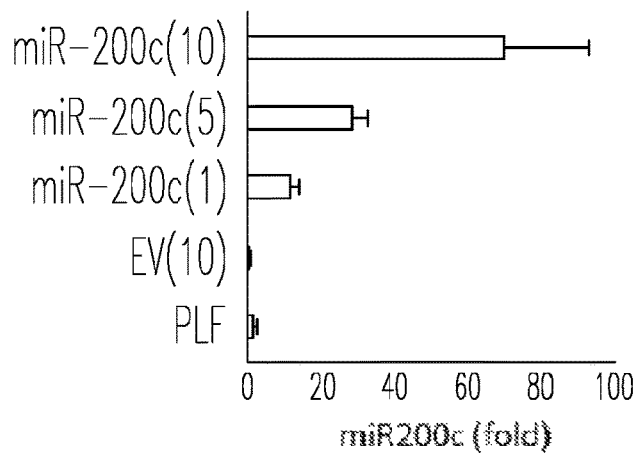
FIG. 5. miR-200c delivered using PEI nanoplexes reduces IL-8 and IL-6 in human primary periodontal ligament fibroblasts. A) Fold changes of miR-200c expression in human PLFs transfected with empty vector (EV) (10 μg/per well) and miR-200c (1, 5 or 10 μg/per well), respectively. B) and C) the amounts of IL-6 (B) and IL-8 (C) in the supernatant of cells treated with PEI-miR-200c (0.5, 5 or 10 μg/per well), PEI-empty vector, and PEI alone after 32 hours of exposure to LPS (1 μg/mL). N=3, *p<0.05.
Figure 5B:
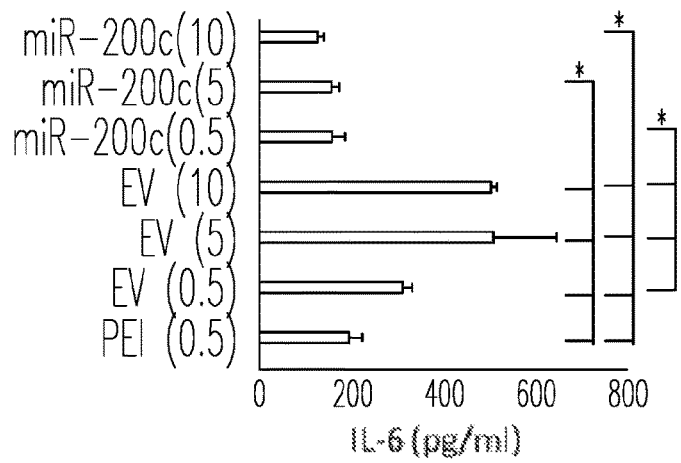
Figure 5C:
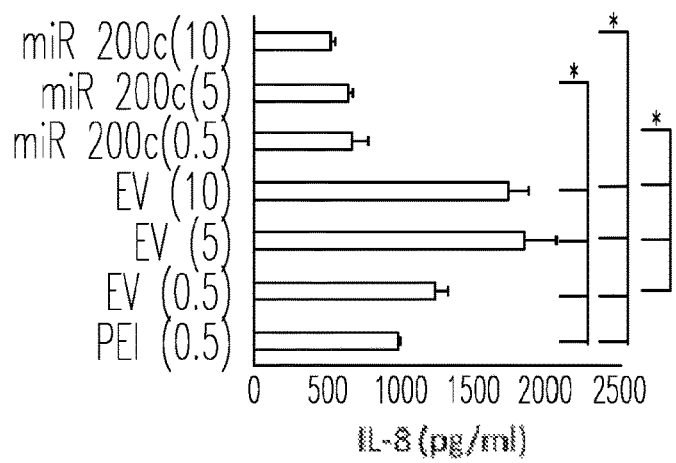
Figure 6A:
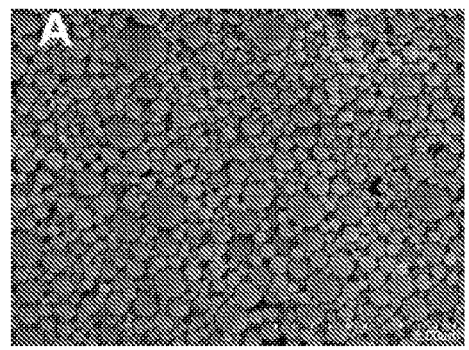
FIG. 6. Intracellular delivery of miR-200a using PLGA nanoparticles. A) SEM photograph of miR-200a-loaded PLGA-PEI nanoparticles; B) the Ct value of endogenous control gene (U6) and miR-200a (200a) of HEPM cells 3 days after receiving treatment of miR-200a or scrambled miR-loaded PLGA-PEI nanoparticles.
Figure 6B:
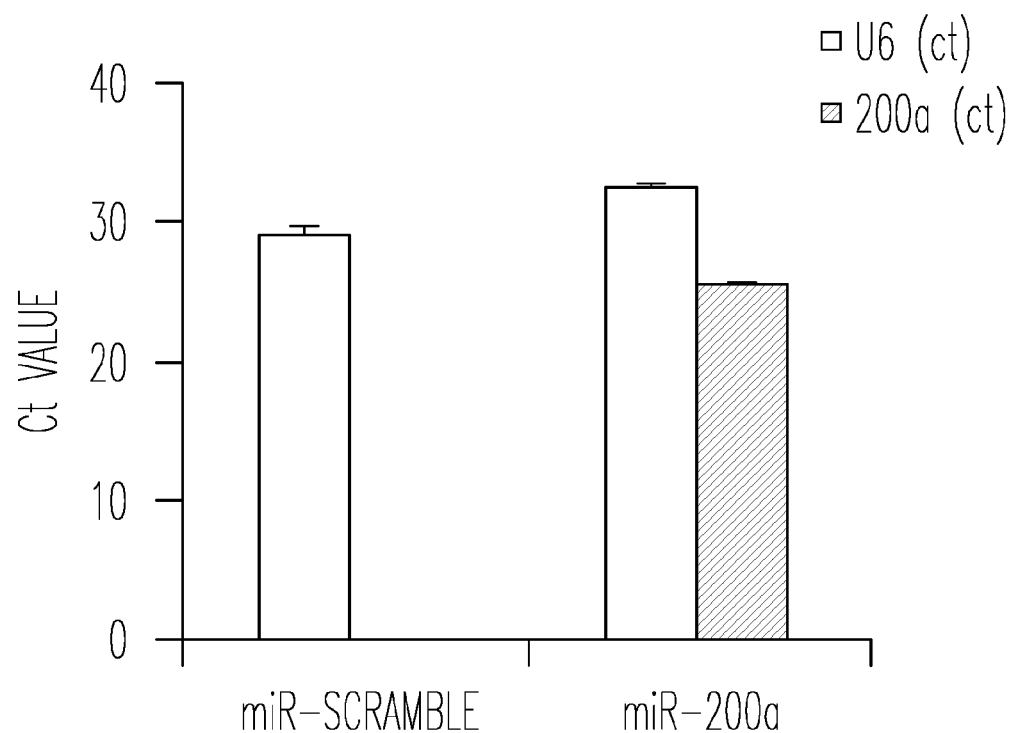
Figure 7:
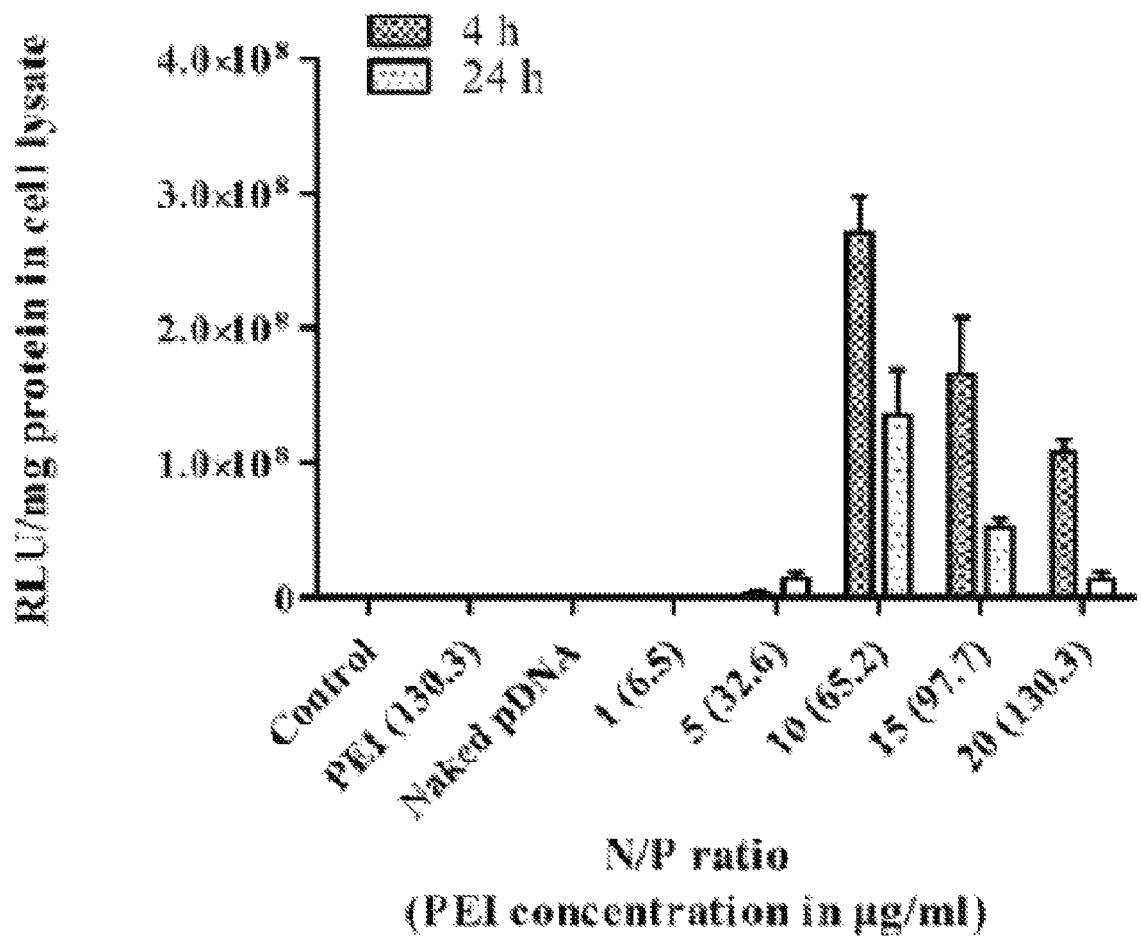
FIG. 7. Luciferase assay assessing the effect of N/P ratio on the transfection capability of PEI-pDNA (encoding for firefly luciferase reporter protein) complexes in MSCs at 4 hours or 24 hours (n=3).
Figure 8C:
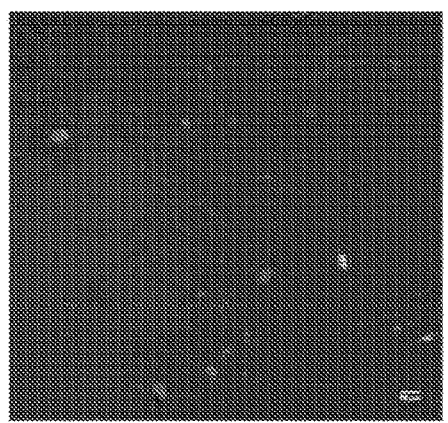
FIG. 8. Influence of the complexes-loaded scaffolds on proliferation of MSCs: confocal image demonstrating proliferating cells on empty scaffolds (A) and on PEI-pDNA (encoding for PDGF-B) complexes-loaded scaffolds (B), and measurement of proliferation of BMSCs seeded on complexes-loaded scaffolds (C) at day 3 of culture. Scale bar, 20 μm.
Figure 8C:
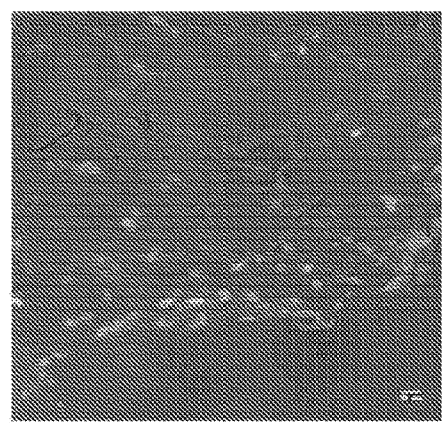
Figure 8C:
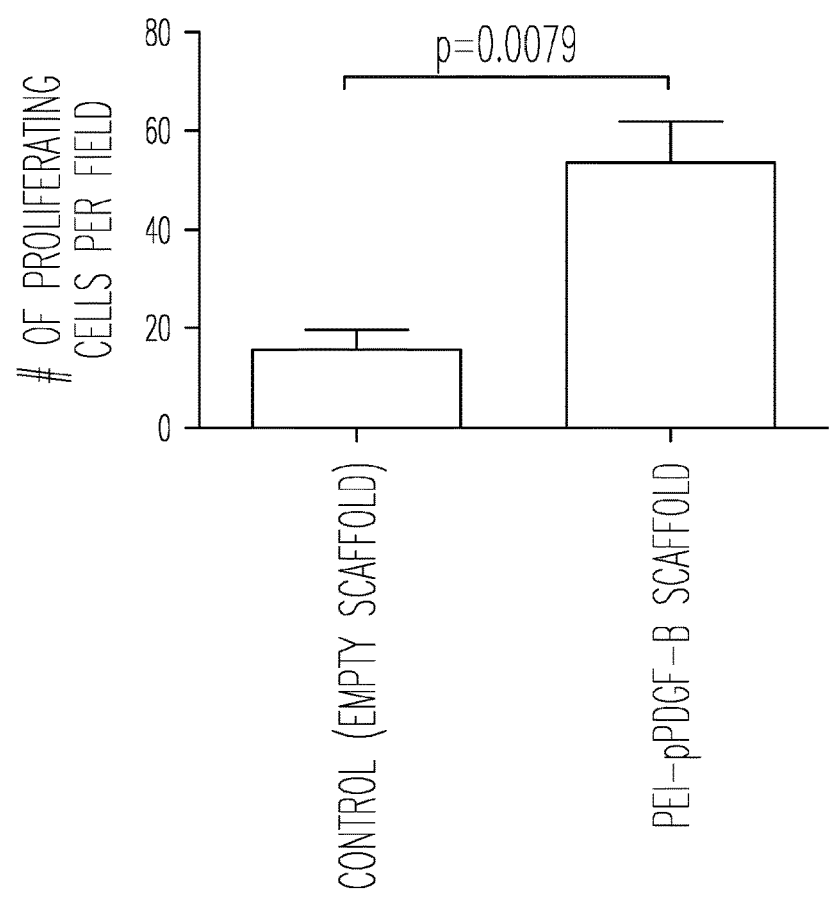

Studies revealed that the overexpression of mir-200c effectively reduced the amount of IL-8 (an inflammatory chemokine) produced in human preosteoblasts in vitro after exposure to lipopolysaccharide (LPS), one of the most powerful bacterial virulence factors (see FIGS. 1-2 and 4). In addition, a non-viral gene delivery system using poly (lactic-co-glycolic acid) (PLGA) nanoparticles was shown to effectively deliver mir-200c into human cells.

Exemplary miRNAs

In one embodiment, the composition includes at least one member of the miRNA-200 family that may be introduced to or expressed in a cell and transcribed to a mature miRNA. By "mature miRNA" is meant the final product of the normal in vivo processing of the transcript of the miRNA gene, i.e., the small non-coding RNA, from between about 19 to about 25 nucleotides, that binds to and cleaves the transcript (mRNA) of a target gene. In many embodiments, the miRNA gene introduced to or expressed in the cell and transcribed and processed to a mature miRNA is endogenous to the cell, i.e., an endogenous miRNA gene that is natively expressed in the cell and transcribed and processed to a mature miRNA. In some embodiments, the miRNA introduced to or expressed in the cell is a miRNA from a multi-gene miRNA family with a high level of mature miRNA sequence conservation.

The invention additionally includes embodiments where the mature miRNA introduced to or transcribed in the cell is from recombinant nucleic acid sequences, such as synthetic miRNA sequences engineered to suppress a particular target gene. Thus, further embodiments encompassed by this invention include a miRNA gene that is orthologous to an endogenous miRNA gene native to or natively expressed in the cell but that is obtained from another species, generally though not always related, e.g., a closely related species; in such embodiments the orthologous miRNA gene can be selected to substantially recapitulate the pattern of expression of a miRNA gene native to or natively expressed in the cell. In yet other embodiments, the miRNA gene is a synthetic sequence, typically one modified from a naturally occurring miRNA sequence selected to substantially recapitulate the pattern of expression of a miRNA gene native to or natively expressed in the cell, one that includes regulatory elements selected to substantially recapitulate the pattern of expression of a miRNA gene native to or natively expressed in the cell, or one that includes regulatory elements selected to not substantially recapitulate the pattern of expression of a miRNA gene native to or natively expressed in the cell. In one embodiment, the regulatory sequences are those of a native miRNA. In general, expression of miRNA from a recombinant DNA construct can be driven by various promoters, including, but not limited to, tissue-specific, cell-specific, temporal-specific, spatial-restricted, inducible, or constitutive promoters.

MicroRNA useful in a recombinant DNA construct and methods of the invention can be identified or designed for any mature miRNA, whether the mature miRNA is endogenously expressed in a cell or is transcribed from a recombinant DNA construct. In some embodiments, there exists at least 1 mismatch between the target and the mature miRNA. Mismatches that are permitted, but are not required, for example, 0, 1 or 2 mismatches between the target and the mature miRNA, wherein each of the mismatches may be adjacent to at least one complementary base-pair (so that there are not more than 2 contiguous mismatches. In some embodiments, there exist no mismatches (there are all complementary base-pairs). Non-limiting embodiments of a miRNA include 1, 2, 3, or 4 nucleotide insertions, or 1, 2, 3 or 4 mismatches, between the target and a mature miRNA.

The miRNA can be a RNA of any length as long as it is recognized and bound by a target to form a cleavable RNA duplex. Specific embodiments include but are not limited to miRNA of 18, 19, 20, 21, 22, 23, 24, 25, 26, 27, 28, 29, 30 or 31 nucleotides in length. The length of the single-stranded RNA is not necessarily equal to the length of the hybridized segment, since not all of the single-stranded RNA necessarily binds to the transcript of at least one target gene. In some embodiments, the length of the single-stranded RNA is about equal to, or exactly equal to, the length of the hybridized segment. In other embodiments, the length of the single-stranded RNA is greater than the length of the hybridized segment. Expressed in terms of numbers of contiguous nucleotides, the length of the single-stranded RNA is generally from about 10 nucleotides to about 500 nucleotides, or from about 20 nucleotides to about 500 nucleotides, or from about 20 nucleotides to about 100 nucleotides, for example, about 10, 11, 12, 13, 14, 15, 16, 17, 18, 19, 20, 21, 22, 23, 24, 25, 26, 27, 28, 29, about 30, about 35, about 40, about 45, about 50, about 60, about 70, about 80, about 90, about 100, about 120, about 140, about 160, about 180, about 200, about 240, about 280, about 320, about 360, about 400, or about 500 nucleotides.

The miRNA can be a naturally-occurring sequence or an artificial sequence. In one embodiment, the miRNA includes a naturally occurring sequence, for example, an endogenous miRNA identified by bioinformatics prediction from genomic sequence. In another embodiment, the miRNA includes a synthetic miRNA, for example, one that includes a nucleotide sequence designed de novo or ab initio, e.g., by using as guidelines the bioinformatics rules provided by this disclosure, to bind to a given mature miRNA to form a cleavable RNA duplex.

Recombinant DNA constructs of this invention may be employed to prepare miRNA, and these constructs may include at least one miRNA and can include multiple miRNAs (either multiple copies of a single miRNA, each copy having the same sequence or copies of different miRNA, or a combination of both). In one example, multiple copies of a single miRNA are arranged in tandem in a recombinant DNA construct.

One embodiment of the invention is a recombinant DNA construct including DNA that is processed to an RNA including single-stranded RNA that binds to the transcript of at least one target gene to form a hybridized segment of at least partially double-stranded RNA that allows for cleavage by an RNase III ribonuclease within or in the vicinity of the hybridized segment. The binding of the single-stranded RNA to the transcript (and the resultant formation of the hybridized segment), where the cleavage by an RNase III ribonuclease is mediated by binding of a mature miRNA, the binding is at a miRNA recognition site (that is recognized by the mature miRNA) in the transcript, the cleavage of the transcript occurs at the miRNA recognition site, and the hybridized segment is formed at least partially within the miRNA recognition site.

In one embodiment, the miRNA has at least 70%, 80%, e.g., at least 85%, 87%, 90%, 92%, 93%, 94%, 95%, 96%, 97%, 98% or 99% nucleic acid sequence identity to human miRNA-200c, e.g., having one of SEQ ID Nos. 1-3.

```
hsa-mir-200c (precursor miRNA)
Accession: MI0000650
Length:    68 bp
Sequence:  5'-
           CCCUCGUCUUACCCAGCAGUGUUUGGGUGCGGUUGGGAG
           UCUCUAAUACUGCCGGGUAAUGAUGGAGG-3'
           (SEQ ID NO: 1)

hsa-miR-200c* (-5p)(mature miRNA)
Accession: MIMAT0004657
Length:    23
Sequence:  5'-CGUCUUACCCAGCAGUGUUUGG-3'
           (SEQ ID NO: 2)

hsa-miR-200c-3p (mature miRNA)
Accession: MIMAT0000617
Length:    23
Sequence:  5'-UAAUACUGCCGGGUAAUGAUGGA-3'
           (SEQ ID NO:3)
```

Exemplary Delivery Vehicles

Delivery vehicles for the miRNAs in the compositions of the invention include, for example, naturally occurring polymers, microparticles, nanoparticles, and other macromolecular complexes capable of mediating delivery of a nucleic acid to a host cell. Vehicles can also comprise other components or functionalities that further modulate, or that otherwise provide beneficial properties.

In one embodiment, the delivery vehicle is a naturally occurring polymer, e.g., formed of materials including but not limited to albumin, collagen, fibrin, alginate, extracellular matrix (ECM), e.g., xenogeneic ECM, hyaluronan (hyaluronic acid), chitosan, gelatin, keratin, potato starch hydrolyzed for use in electrophoresis, or agar-agar (agarose). In one embodiment, the delivery vehicle comprises a hydrogel. In one embodiment, the composition comprises a naturally occurring polymer. For example, the miRNA may be in nanoparticles or microparticles. Table 1 provides exemplary materials for delivery vehicles that are formed of naturally occurring polymers and materials for particles.

TABLE 1

| Particle class | Materials |
| --- | --- |
| Natural materials or derivatives | Chitosan |
| | Dextran |
| | Gelatine |
| | Albumin |
| | Alginates |
| | Liposomes |
| | Starch |
| Polymer carriers | Polylactic acid |
| | Poly(cyano)acrylates |
| | Polyethyleneimine |
| | Block copolymers |
| | Polycaprolactone |

An exemplary polycaprolactone is methoxy poly(ethylene glycol)/poly(epsilon caprolactone). An exemplary poly lactic acid is poly(D,L-lactic-co-glycolic)acid (PLGA).

Some examples of materials for particle formation include but are not limited to agar acrylic polymers, polyacrylic acid, poly acryl methacrylate, gelatin, poly(lactic acid), pectin(poly gycolic acid), cellulose derivatives, cellulose acetate phthalate, nitrate, ethyl cellulose, hydroxyl ethyl cellulose, hydroxypropylcellulose, hydroxyl propyl methyl cellulose, hydroxypropylmethylcellulose phthalate, methyl cellulose, sodium carboxymethylcellulose, poly(ortho esters), polyurethanes, poly(ethylene glycol), poly(ethylene vinyl acetate), polydimethylsiloxane, poly(vinyl acetate phthalate), polyvinyl alcohol, polyvinyl pyrollidone, and shellac. Soluble starch and its derivatives for particle preparation include amylodextrin, amylopectin and carboxy methyl starch.

In one embodiment, the polymers in the nanoparticles or microparticles are biodegradable. Examples of biodegradable polymers useful in particles preparation include synthetic polymers, e.g., polyesters, poly(ortho esters), polyanhydrides, or polyphosphazenes; natural polymers including proteins (e.g., collagen, gelatin, and albumin), or polysaccharides (e.g., starch, dextran, hyaluronic acid, and chitosan). For instance, a biocompatible polymer includes poly (lactic) acid (PLA), poly (glycolic acid) (PLGA). Natural polymers that may be employed in particles (or as the delivery vehicle) include but are not limited to albumin, chitin, starch, collagen, chitosan, dextrin, gelatin, hyaluronic acid, dextran, fibrinogen, alginic acid, casein, fibrin, and polyanhydrides.

In one embodiment, the delivery vehicle is a hydrogel. Hydrogels can be classified as those with chemically crosslinked networks having permanent junctions or those with physical networks having transient junctions arising from polymer chain entanglements or physical interactions, e.g., ionic interactions, hydrogen bonds or hydrophobic interactions. Natural materials useful in hydrogels include natural polymers, which are biocompatible, biodegradable, support cellular activities, and include proteins like fibrin, collagen and gelatin, and polysaccharides like starch, alginate and agarose.

In one embodiment, a non-viral delivery vehicle comprises inorganic nanoparticles, e.g., calcium phosphate or silica particles; polymers including but not limited to poly (lactic-co-glycolic acid) (PLGA), polylactic add (PLA), linear and/or branched PEI with differing molecular weights (e.g., 2, 22 and 25 kDa), dendrimers such as polyamidoamine (PAMAM) and polymethoacrylates; lipids including but not limited to cationic liposomes, cationic emulsions, DOTAP, DOTMA, DMRIE, DOSPA, distearoylphosphatidylcholine (DSPC), DOPE, or DC-cholesterol; peptide based vectors including but not limited to Poly-L-lysine or protamine; or poly(β-amino ester), chitosan, PEI-polyethylene glycol, PEI-mannose-dextrose, DOTAP-cholesterol or RNAiMAX.

In one embodiment, the delivery vehicle is a glycopolymer-based delivery vehicle, poly(glycoamidoamine)s (PGAAs), that have the ability to complex with various polynucleotide types and form nanoparticles. These materials are created by polymerizing the methylester or lactone derivatives of various carbohydrates (D-glucarate (D), meso-galactarate (G), D-mannarate (M), and L-tartarate (T)) with a series of oligoethyleneamine monomers (containing between 1-4 ethylenamines. A subset composed of these carbohydrates and four ethyleneamines in the polymer repeat units yielded exceptional delivery efficiency.

In one embodiment, the delivery vehicle comprises polyethyleneimine (PEI), Polyamidoamine (PAMAM), PEI-PEG, PEI-PEG-mannose, dextran-PEI, OVA conjugate, PLGA microparticles, or PLGA microparticles coated with PAMAM.

In one embodiment, the delivery vehicle comprises a cationic lipid, e.g., N-[1-(2,3-dioleoyloxy)propel]-N,N,N-trimethylammonium (DOTMA), 2,3-dioleyloxy-N-[2-spermine carboxamide]ethyl-N,N-dimethyl-1-propanammonium trifluoracetate (DOSPA, Lipofectamine); 1,2-dioleoyl-3-trimethylammonium-propane (DOTAP); N-[1-(2,3-dimyristloxy) propyl]; N,N-dimethyl-N-(2-hydroxyethyl) ammonium bromide (DMRIE), 3-β-[N—(N,N'-dimethylaminoethane) carbamoyl] cholesterol (DC-Chol); dioctadecyl amidoglyceryl spermine (DOGS, Transfectam); or imethyldioctadeclyammonium bromide (DDAB). The positively charged hydrophilic head group of cationic lipids usually consists of monoamine such as tertiary and quaternary amines, polyamine, amidinium, or guanidinium group. A series of pyridinium lipids have been developed. In addition to pyridinium cationic lipids, other types of heterocyclic head group include imidazole, piperizine and amino acid. The main function of cationic head groups is to condense negatively charged nucleic acids by means of electrostatic interaction to slightly positively charged nanoparticles, leading to enhanced cellular uptake and endosomal escape.

Lipids having two linear fatty acid chains, such as DOTMA, DOTAP and SAINT-2, or DODAC, may be employed as a delivery vehicle, as well as tetraalkyl lipid chain surfactant, the dimer of N,N-dioleyl-N,N-dimethylammonium chloride (DODAC). All the trans-orientated lipids regardless of their hydrophobic chain lengths ($C_{16:1}$, $C_{18:1}$ and $C_{20:1}$) appear to enhance the transfection efficiency compared with their cis-orientated counterparts.

The structures of cationic polymers useful as a delivery vehicle include but are not limited to linear polymers such as chitosan and linear poly(ethyleneimine), branched polymers such as branch poly(ethyleneimine) (PEI), circle-like polymers such as cyclodextrin, network (crosslinked) type polymers such as crosslinked poly(amino acid) (PAA), and dendrimers. Dendrimers consist of a central core molecule, from which several highly branched arms 'grow' to form a tree-like structure with a manner of symmetry or asymmetry. Examples of dendrimers include polyamidoamine (PAMAM) and polypropyleneimine (PPI) dendrimers.

DOPE and cholesterol are commonly used neutral co-lipids for preparing cationic liposomes. Branched PEI-cholesterol water-soluble lipopolymer conjugates self-assemble into cationic micelles. Pluronic (poloxamer), a non-ionic polymer and SP1017, which is the combination of Pluronics L61 and F127, may also be used.

In one embodiment, PLGA particles are employed to increase the encapsulation frequency although complex formation with PLL may also increase the encapsulation efficiency. Other cationic materials, for example, PEI, DOTMA, DC-Chol, or CTAB, may be used to make nanospheres.

In one embodiment, no delivery vehicle is employed, e.g., naked cmRNA is employed alone or with a scaffold.

In one embodiment, physical methods including but not limited to electroporation, sonoporation, magnetoporation, ultrasound or needle injection may be employed to introduce naked miRNA, complexes of miRNA and a delivery vehicle or miRNA encapsulated in particles.

Formulations and Dosages

The miRNAs can be formulated as pharmaceutical compositions and administered to a mammalian host, such as a human patient in a variety of forms adapted to the chosen route of administration, e.g., orally or parenterally, by intravenous, intramuscular, topical, local, or subcutaneous routes. In one embodiment, the composition having isolated polypeptide or peptide is administered to a site of bone loss or cartilage damage or is administered prophylactically.

In one embodiment, the miRNAs may be administered by infusion or injection. Solutions of the miRNA or its salts, can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion may include sterile aqueous solutions or dispersions or sterile powders comprising the active ingredient which are adapted for the extemporaneous preparation of sterile injectable or infusible solutions or dispersions, optionally encapsulated in complexes, liposomes, nanoparticles or microparticles. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In some cases, it may be preferable to include isotonic agents, for example, sugars, buffers or sodium chloride. Prolonged absorption of the injectable compositions can be brought about by the use in the compositions of agents delaying absorption, for example, microparticles, or aluminum monosterate and gelatin.

Sterile injectable solutions are prepared by incorporating the active agent in the required amount in the appropriate solvent with various of the other ingredients enumerated above, as required, followed by filter sterilization. In the case of sterile powders for the preparation of sterile injectable solutions, the methods of preparation include vacuum drying and the freeze drying techniques, which yield a powder of the active ingredient plus any additional desired ingredient present in the previously sterile-filtered solutions.

Useful solid carriers may include finely divided solids such as talc, day, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as antimicrobial agents can be added to optimize the properties for a given use. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the miRNAs can be determined by comparing their in vitro activity and in vivo activity in animal models thereof. Methods for the extrapolation of effective dosages in mice, and other animals, to humans are known to the art; for example, see U.S. Pat. No. 4,938,949.

Generally, the concentration of the miRNAs in a liquid composition, may be from about 0.1-25 wt-%, e.g., from about 0.5-10 wt-%. The concentration in a semi-solid or solid composition such as a gel or a powder may be about 0.1-5 wt-%, e.g., about 0.5-2.5 wt-%.

The amount of the miRNAs for use alone or with other agents will vary with the route of administration, the nature of the condition being treated and the age and condition of the patient and will be ultimately at the discretion of the attendant physician or clinician.

The miRNAs may be conveniently administered in unit dosage form; for example, containing 5 to 1000 mg, conveniently 10 to 750 mg, or conveniently 50 to 500 mg of active ingredient per unit dosage form.

In general, a suitable dose may be in the range of from about 0.5 to about 100 mg/kg, e.g., from about 10 to about 75 mg/kg of body weight per day, such as 3 to about 50 mg per kilogram body weight of the recipient per day, for example in the range of 6 to 90 mg/kg/day, e.g., in the range of 15 to 60 mg/kg/day.

The invention will be described by the following non-limiting examples.

Example 1

Toll-Like Receptors (TLRs), which could recognize microbial pathogens, are major components in the innate and adaptive immune systems. TLR-2 and TLR4 have been demonstrated to play critical roles in recognizing periodontal pathogens and trigger the up-regulation of IL-6, IL-1β, and TNF-α to resistance to infection in periodontitis. TLR-mediated signaling pathways also lead to activation of NF-κB (a key proinflammatory transcription factor). These cytokines and transcription factors in turn further amplify the inflammatory response and lead to production of lytic enzymes and stimulate the production of chemokines.

Table 2 summarizes the major proinflammatory cytokines and transcription factors that are up-regulated in resident cells that involve in periodontitis-induced bone resorption, including oral epithelial cells, gingival fibroblasts, periodontal ligament fibroblasts, osteoblast, and dendritic cells. Migrating cells, including lymphocytes and phagocytes, produce RANKL, TNF-α, and IL-17. Eventually, a cascade of events leads to osteoclastogenesis and subsequent bone resorption via the RANKL-OPG axis. Thus, the imbalance and dysregulation of proinflammatory cytokine, transcription factors, and bone metabolism mediators play critical roles in causing periodontitis-induced bone resorption. In addition, proinflammatory factors have been demonstrated to impair bone formation by reducing differentiation of osteoblasts and their progenitor cells. These findings include: 1) TNF-α and IL-1β inhibit osteogenic differentiation of bone marrow MSCs; 2) TNF-α may inhibit Osterix expression and promote degradation of Runx2, 3) TNF-α and IL-17 activate IκB kinase (IKK)—NF-κB to reduce osteogenic differentiation of MSCs by promoting β-catenin degradation and impair bone formation. Inhibition of NF-kB increases trabecular bone mass and bone mineral density. miR-200c, a member of the miR-200 family, is significantly underexpressed in gingival tissues of periodontitis patients. miR-200c is down-regulated in the inflammatory signaling pathway mediated by IL-6. miR-200c has also been found to potentially inhibit NF-kB activation and IL-8 expression in leiomyoma smooth muscle cells. Preliminary Studies showed that miR-200c overexpression reduced IL-8 by targeting IL-8 3'UTR and increased OPG in human preosteoblasts. miR-200c overexpression also inhibited IL-8 in human primary periodontal ligament fibroblasts (PLFs). In addition, miR-200c has been reported to regulate stem cell proliferation and differentiation. Other preliminary studies also show that miR-200c can improve osteogenic differentiation of human preosteoblasts and bone marrow MSCs. In a recent study, it was shown that PEI nanoparticles can deliver miR-200c into human MSCs, demonstrating the feasibility of transfecting miR-200c using PEI nanoparticles as a non-viral vector.

TABLE 2

Up-regulated major proinflammatory factors in resident cells involving in periodontal bone resorption

Figure 1B:
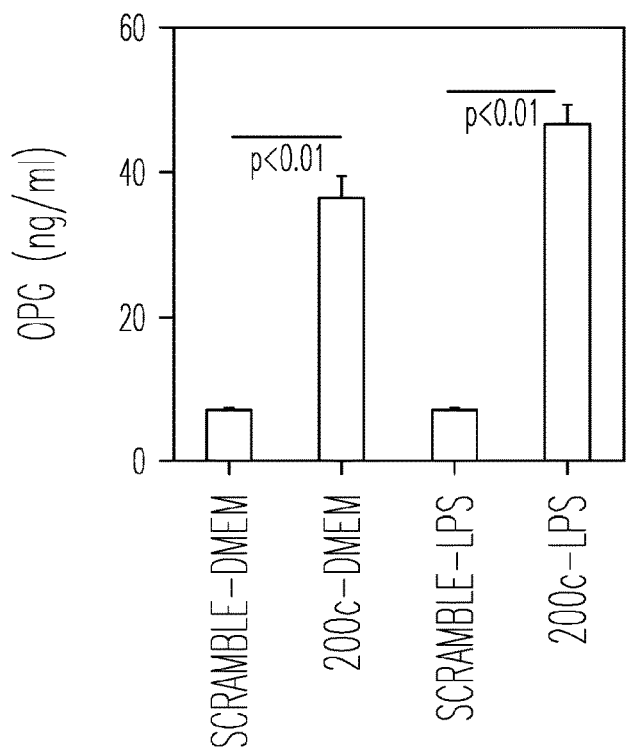
Figure 2A:
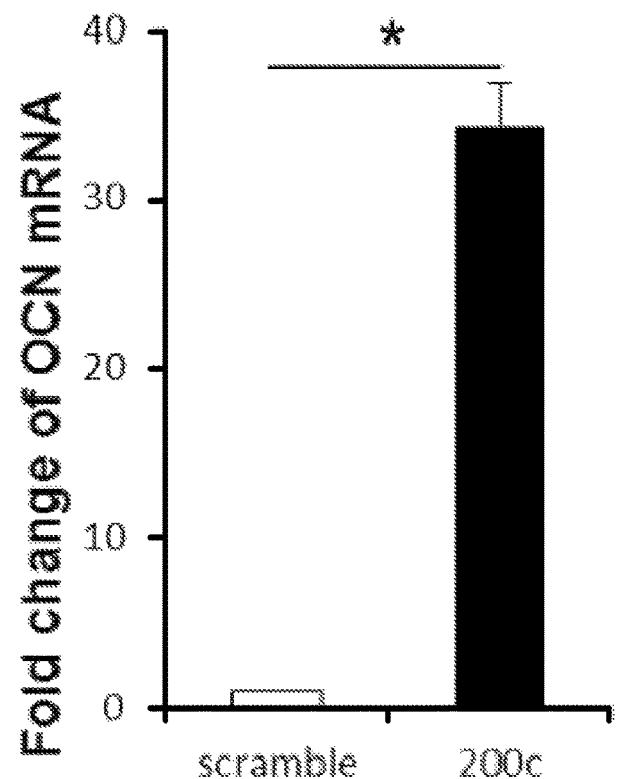
FIG. 2. miR-200c improves osteogenic differentiation of preosteoblasts. A) and B) mRNA and protein levels of OCN in HEPM cells with miR-200c or scrambled miRs, respectively. C) calcium content of preosteoblasts with miR-200c or scrambled miRs 2 weeks after in vitro culture. *: $p<0.05$.
Figure 2B:
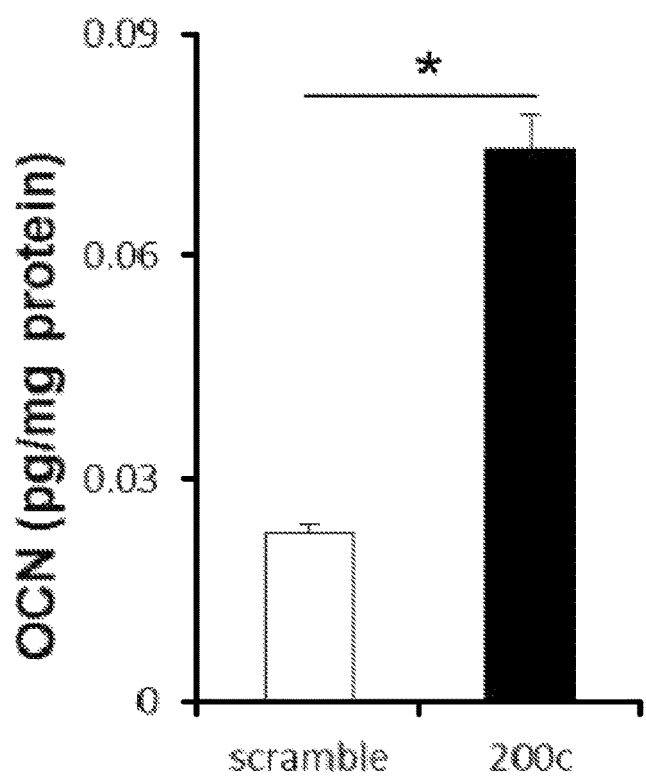
Figure 2C:
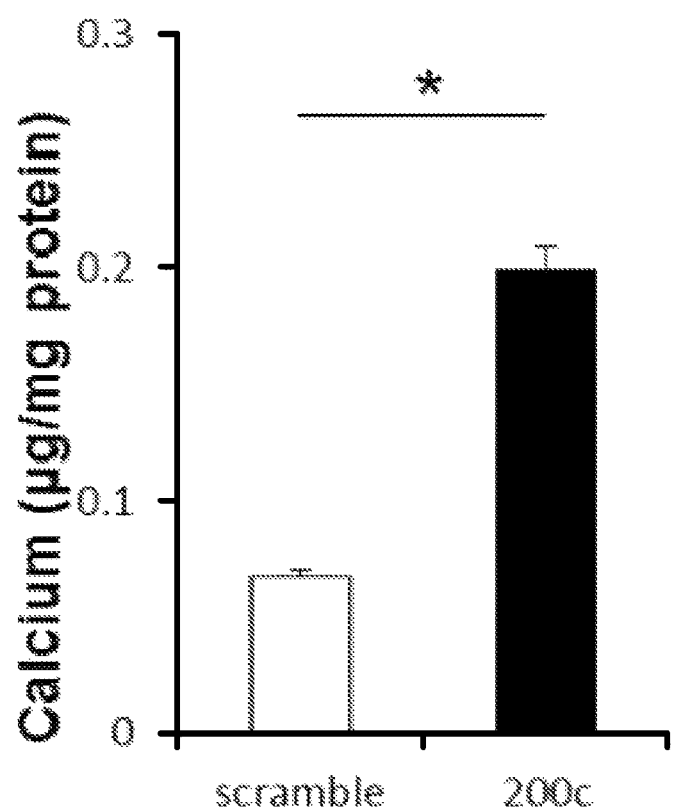

| | |
|---|---|
| Epithelia cells | IL-8 |
| Gingival cells | TNF-α, IL-6, IL-8 |
| Periodontal ligament fibroblast | IL-1β, IL-6, TNF-α, IL-8 |
| osteoblast | NF-kB, IL-1β, RANKL |
| Dendritic cells | IL-12, 18 | miR-200c Overexpression Inhibits IL-8 by Targeting IL-8 3'UTR and Increases OPG miR-200c was transduced into human embryonic palatal mesenchyme cells (HEPM), a preosteoblast cell line, using lentiviral vectors. Scrambled miRs were used as controls. The miR-200c expression in the cells after transduction with miR-200c is 15.9±0.1 (delta/delta Ct) higher than that of controls. The HEPM cells with miR-200c or scrambled miRs were cultured with or without Lonza N-185 LPS (1 µg/ml) (Lonza) up to 32 hours. The amounts of IL-8 and OPG in the culture medium were analyzed using a Luminex®-X100 Analyzer (Millipore Corp). FIG. 1A shows that the amounts of IL-8 in DMEM medium of HEPM cells with miR-200c overexpression are dramatically lower than that of HEPM cells with scrambled miRs at each time point LPS supplement increased the amount of IL-8 in HEPM cells with scrambled miRs starting after 4 hours. However, the cells with miR-200c produced much less IL-8 than that of controls even after they were exposed to LPS. FIG. 1B shows that, after 32 hours, the amount of OPG (an osteoclastogenesis inhibitory factor) secreted by the cells with miR-200c overexpression in culture medium with or without LPS supplement are higher (6-8 folds) than that of cells with scrambled miRs. It was determined if miR-200c directly targets IL-8 3'UTR using luciferase reporter assay. FIG. 1C summarizes the outcome of the luciferase reporter assay of IL-8 3' UTR after transfection with miR-200c. Normalized luciferase activity of the 3' UTR IL-8-luciferase reporter with empty plasmid or miR-200c shows loss of luciferase activity with expression of miR-200c. There is no loss of luciferase activity when the IL-8 3'UTR is mutated. To test the effects of miR-200c on human primary periodontal cells, we transfected miR-200c into primary PLFs at 1, 5, 10 μg/per well in a 6-well plate using a calcium phosphate method. Empty vector (10 μg/per well) was used as a control. After 2 days of transfection, the cells were exposed to LPS (1 ug/mL) for 24 hours. FIG. 1D shows a dose-dependent overexpression of miR-200c in PLFs transfected with miR-200 at different doses. The transcript of IL-8 measured using real-time PCR in miR-200c overexpressed PLFs is significantly lower, compared to control cells with empty vector (FIG. 1D).

miR-200c Overexpression Enhances Osteogenic Differentiation in Human Preosteoblasts and MSCs The HEPM with miR-200c or scrambled miRs were cultured in DMEM medium supplemented with β-glycerophosphate (1 mM) and ascorbic acid (5 mg/ml) up to 2 weeks. After one week, OCN transcripts measured using real-time PCR in miR-200c overexpression cells was 30-fold higher than control cells with scrambled miRs (FIG. 2A). The protein level of OCN measured using an ELISA kit (Invitrogen) was also 3-4 times higher in miR-200c cells than that of control cells after two weeks (FIG. 2B). The calcium content in miR-200c cells was 3 times higher than that of cells with scrambled miRs (FIG. 2C).

Figure 3A:
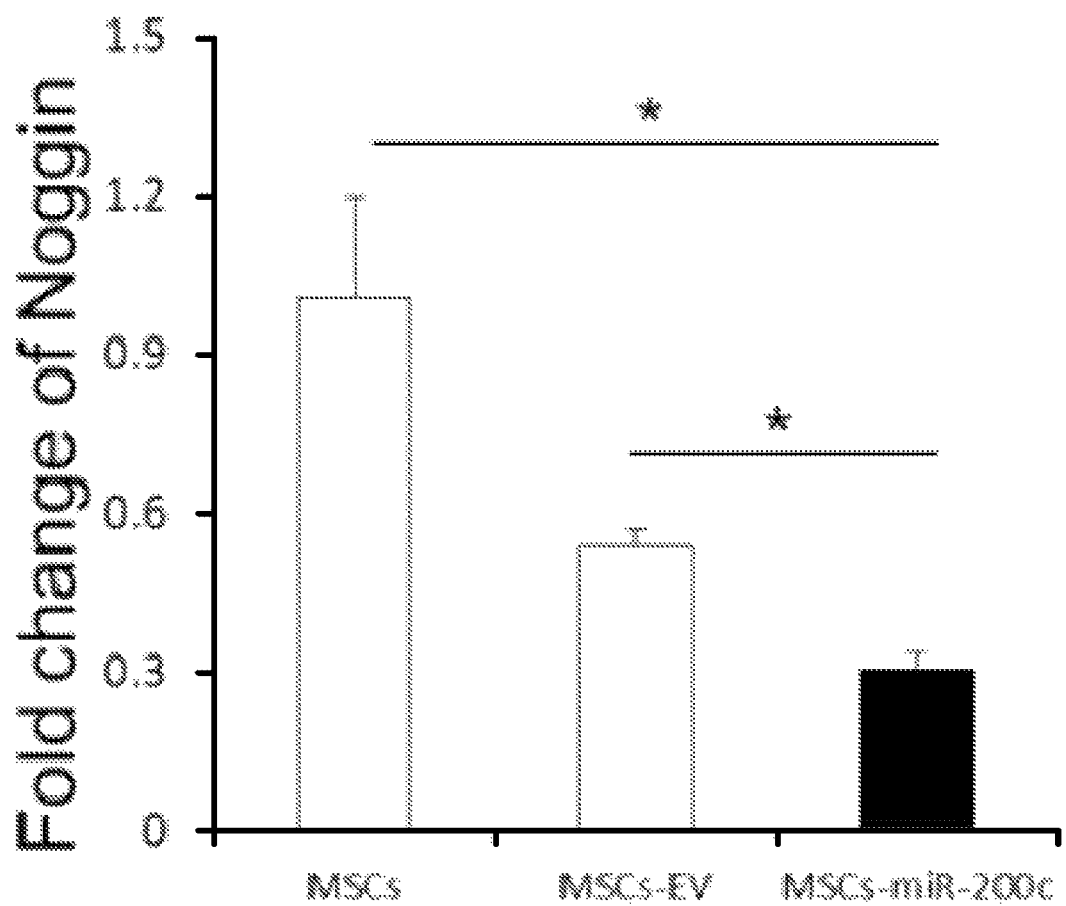
FIG. 3. miR-200c improves osteogenic differentiation of human MSCs. A) and B): mRNA expression of Noggin A) and Runx2 B) in human MSCs with transfection of miR-200c (MSCs-miR-200c) or empty vector (MSCs-EV), respectively 1 week after in vitro culture. *: $p<0.05$.
Figure 3B:
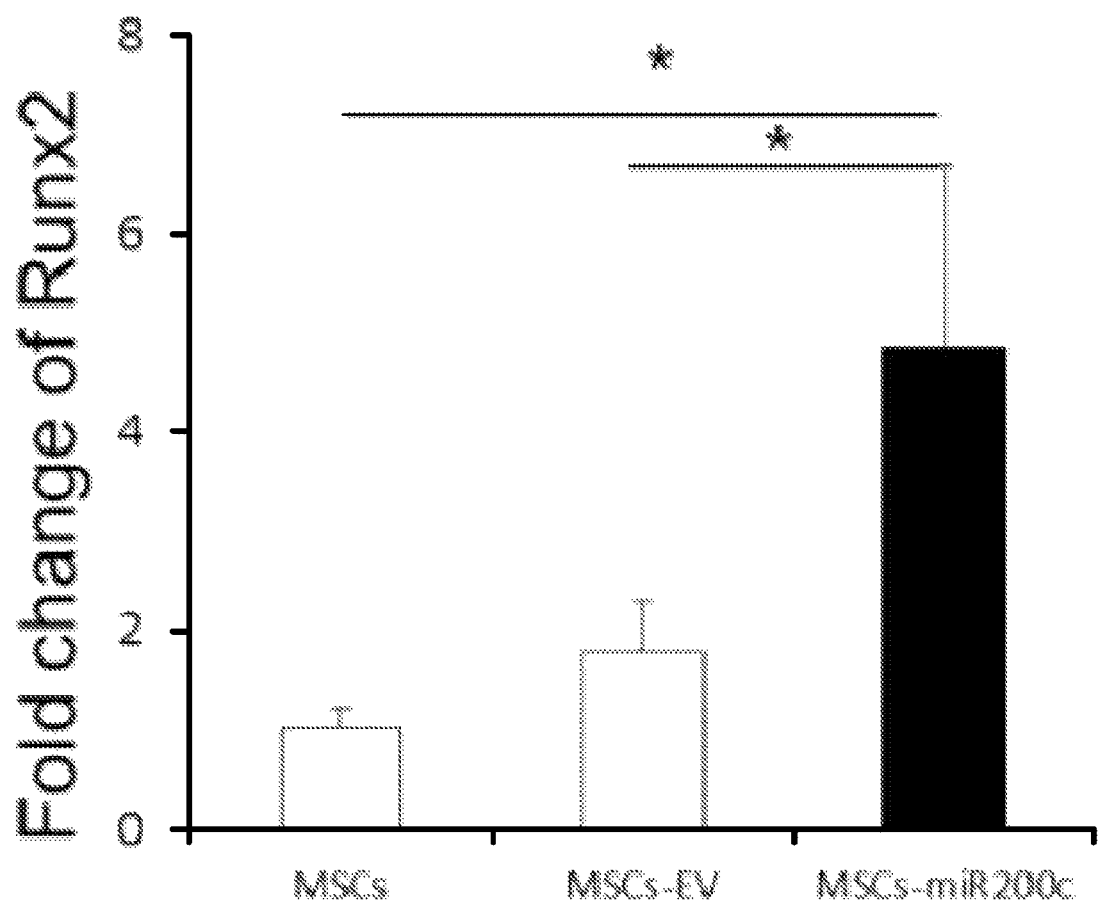

In a pilot study to test the effect of miR-200c on human MSCs, a non-viral vector (X-tremeGENE HP DNA Transfection Reagent, Roche) was used to transfect miR-200c into human bone marrow MSCs. Plasmid miR-200c (3 μg) was used to transfect $10^5$ cells in a 6-well plate according manufacturer's instruction. Empty vector was used as a control. The cells were subsequently cultured in osteogenic differentiation medium consisting of DMEM with dexamethasone (100 nM), ascorbic acid (5 mg/ml) and glycerophosphate (5 mM) up to one week. Overexpression of miR-200c (8.5±1.2, delta/delta Ct) was found in the cells with miR-200c transfection, compared to the cells with empty vector transfection or without transfection. Furthermore, Noggin expression was approximate 3-fold lower in the cells with miR-200c (FIG. 3A). Runx2 expression in the MSCs with miR-200c is about 5-fold higher than that of controls (FIG. 3B).

PEI Nanoparticles Deliver miR-200c into Human Bone Marrow MSCs

Plasmid miR-200c was incorporated into PEI to form nanoplexes at an NIP ratio of 10:1 [ratio of the total number of end amine groups (N) of PEI and the total number of DNA phosphate groups (P)]. The complexes were prepared by adding 50 μl PEI solution to 50 μl miR-200c (10 μg) solution and mixed for 30 seconds. The mixture was then incubated at room temperature for 30 min to allow complex formation between the positively charged PEI and the negatively charged plasmid DNA. The encapsulation efficiency and plasmid miR-200c condensation within the complex were elucidated using spectrophotometry and gel electrophoresis, respectively as our previous studies. In order to test the transfection efficiency, we added 1, 2, 5, and 10 μg PEI-miR-200c nanoplexes into the medium of cultured human MSCs. PEI-empty vector (10 μg) were used as controls. The medium was exchanged the next day to remove extra nanoplexes. After one week miR-200c overexpression in a dose-dependent manner was detected using real-time PCR analysis in the cells treated with PEI-miR-200c nanoplexes (FIG. 4).

The Function of miR-200c on Proinflammatory and Bone Metabolism Factors

Normal human primary cells, including gingival fibroblasts (HGnF, Scien Cell), oral epithelial cells (ABM), dendritic cells (NHDC, Lonza), periodontal ligament fibroblasts (Lonza), and osteoblasts (HOB, PromoCell) are purchased commercially. The cells are treated with PEI alone, miR-200c alone, PEI-miR-200c nanoplexes, and PEI-empty vector nanoplexes at 1, 2, 5, 10 μg at an NIP ratio of 10. The expression of miR-200c with different treatment is measured using real-time PCR. After 2 days of transfection, each type of cells ($10^5$) is cultured in 2 ml DMEM completed medium supplemented with or without LPS (1 μg/mL) (Lonza). A small portion of culture medium (300 μL) of different cells with different treatments is collected at 0, 1, 2, 4, 6, 12, 24, and 32 hours. The cells are collected after 32 hours. The amounts of TLR-2, 4, MYD88, inflammatory chemokine (IL-8, CCL5), cytokines (IL-1β, TNF-α, and IL-6), IKK-α/β, transcription factor (NF-kB p65), RANKL, and OPG in the medium samples and the lysates of the cells with different treatment at each time point are measured using a Luminex®-X100 Analyzer (Millipore) according to the manufacturer's protocol. Real-time PCR is used to quantify the transcripts of these proinflammatory and bone mediators.

Osteogenic Differentiation Induced by miR-200c Overexpression

Human bone marrow MSCs are treated with PEI-miR-200c nanoplexes. The cells are cultured in osteogenic medium consisting of DMEM supplemented with ascorbic acid (5 mg/ml) and glycerophosphate (5 mM) and lysed at 48, 72 and 96 hours. Noggin, alkaline phosphatase (ALP), Runx2, collagen type I, OCN, bone sialoprotein (BSP), and Osterix transcripts are determined using real-time PCR. ALP activity, the protein of OCN, BSP, collagen type 1 and calcium content of transfected MSCs are quantitated after 1 and 2 weeks.

Target Site of miR-200c in Proinflammatory and Bone Metabolism Mediators

A luciferase reporter assay is used to determine if miR-200c directly targets the 3'UTR of proinflammatory cytokines and bone metabolism mediators. The 3'UTR of cytokines or mediators that are repressed by miR-200c is cloned downstream of the luciferase gene in the pGL3 vector (Promega). The PCR-driven overlap extension method is used to mutate the binding site of miR-200c in the 3'UTR of these factors. HEPM cells are fed for 24 hours prior to transient transfection, resuspended in PBS and mixed with 2 μg miR-200c (p-Silencer), (pcDNA3.1) expression plasmids, 0.1 μg reporter plasmid (pGL3) and 0.5 μg β-galactosidase plasmid. Transfected cells are incubated for 48 hours, lysed and assayed for reporter activities and protein content by the Bradford assay (Bio-Rad). Luciferase is measured using reagents from Promega. β-galactosidase is measured using Galacto-Light Plus reagents (Tropix). All luciferase activities are normalized to β-galactosidase activity and are shown as mean-fold differences relative to empty luciferase plasmids.

In Vitro Conclusions

PEI nanoparticles can efficiently deliver and transfect miR-200c into human primary cells. Overexpression of miR-200c delivered by PEI will effectively down-regulate MYD88, IL-1β, TNF-α, IKK-α/β, IL-6, IL-8, NF-kB p65, and RANKL, and improve expression of OPG in human primary cells that participate in periodontitis-associated bone loss. mRNA expression and protein level of the specific biomarkers of osteogenic differentiation and bone formation is likely significantly higher in human MSCs transfected with miR-200c, compared to other treatments. The data demonstrate if there is a dose-dependent manner of miR-200c modulation on proinflammatory factors and osteogenic differentiation and potential off-target effects of miR-200c under high concentrations. N/P ratios significantly influence the size, surface charge, transfection efficiency and cytotoxicity of PEI nanoplexes.

In Vivo Experiments

NF-kB and IL-8 play critical roles in the development of periodontitis-associated bone loss by stimulating osteoclastogenesis and bone resorption. Thus, miR-200c-mediated suppression of IL-8 and NF-kB may effectively prevent and arrest periodontal bone loss. Since Noggin inhibition increases bone formation miR-200c overexpression may also improve bone formation by inhibiting Noggin. Studies described above revealed that miR-200c overexpression may improve osteogenic differentiation of human MSCs and preosteoblasts. This evidence strongly indicated that miR-200c can be used to arrest and restore periodontitis-induced alveolar bone loss. Degradable nanoparticles have been demonstrated to provide a targeted intracellular delivery with controlled release properties. Nanoparticles can also serve as a local drug delivery system to oral mucosa. In a pilot study miR-200c was delivered into human bone marrow MSCs using PEI nanoparticles. While there are a number of animal models of periodontitis, a rat model with a ligature of silk threads around the cervix of the 2nd maxillary molar has been used to investigate periodontitis-induced bone loss. Local injection at palatal/interproximal gingiva around the maxilla molar in this model has been extensively used to test the in vivo efficacy of different therapeutic agents for periodontal bone loss.

Animal Model of Periodontitis and Treatment with PEI-miR-200c Nanoplexes 4-week-old male Sprague Dawley (SD) rats are purchased from Charles River Laboratories. PEI-miR-200c nanoplexes are prepared as described. Under general anesthesia using ketamine and xylazine, a ligature of silk threads (4-0) soaked with LPS (1 mg/mL) are displaced apically into the gingival sulci of the 2nd maxillary molar of rats under a stereomicroscope. The rats then are randomly divided and receive different treatments of PEI-miR-200c or empty vector nanoplexes. Eight treatment groups are designed for this study, including: 1) sham operation; 2) LPS-soaked ligature without treatment; 3) LPS-soaked ligature with PEI nanoparticles alone; 4) LPS-soaked ligature with PEI-empty vector (1 µg); 5) LPS-soaked ligature with PEI-empty vector (10 µg); 6) LPS-soaked ligature with PEI-miR-200c (1 µg); 7) LPS-soaked ligature with PEI-miR-200c (10 µg) 8) LPS-soaked ligature with plasmid miR-200c (10 µg). The nanoplexes are suspended in 10-15 µL saline and injected into the palatal/interproximal gingiva between the maxillary first, second, and third molars using a 33-gauge Hamilton syringe. The ligature is checked and replaced if they become dislodged. Since periodontal bone loss occurs in this model after 8-10 days, the rats with different treatments are euthanized after 1 and 2 weeks and maxillas is hemisected. Gingival tissue around 2nd maxillary molar is collected to measure miR-200c expression using real-time PCR. The harvested maxillae block sections are fixed in 4% formaldehyde and analyzed using µCT imaging and histomorphometry to determine bone resorption.

Assessment of Bone Loss

µCT imaging is performed on the specimens using a cone-beam µCT system (µCT40, Scanco Medical AG). Specimens are scanned in 70% ethanol at 55 kVp and 145 µA with a voxel size of 10 µm and an integration time of 300 ms. Analysis is performed using a constant 3.5 mm diameter circular region of interest that is placed in the center of the machined defect and spanned a total of 50 reconstructed slices. µCT data will be acquired and reconstructed using the manufacturer's software. This enables the observation of the morphology around the tooth and dental alveolar bone in all dimensions, including the cemento-enamel junction (CEJ), root surface and dental alveolar crest, as well as the relationships among these areas. µCT with reconstructed three-dimensional images will be used to assess the distance between the CEJ and the coronal level of the alveolar bone crests (the µCT bone levels) at 4 sites, including the mesiobuccal and distobuccal sites, and the mesiopalatal and distopalatal sites of the maxillary 2nd molars. After µCT scanning, the maxillary specimens are prepared for histology. After decalcification with 10% acetic acid, 4% formaldehyde, and 0.85% NaCl for 3 weeks, the specimens are cut into 10 µm sections sagittally and stained with hematoxylin and eosin (HE) and tartrate-resistant acid phosphatase (TRAP) staining. The images are captured with a digital camera coupled with the microscope and connected to a computer, and are analyzed using Image J image-analysis software. On the mesial surfaces of the 2nd molars receiving different treatments, the following histometric measurements are performed: the distance of the CEJ to the coronal level of epithelial cells (attachment loss); the distance of the CEJ to the alveolar bone crest; the distance of the apical level of epithelial cells to the alveolar bone crest; and the area of inflammatory cell-infiltrated connective tissue.

Statistical Analysis

The primary outcomes are bone loss derived from µCT analysis, including the distance between the CEJ and the coronal level of the alveolar bone crests, and histomorphometric analysis, including the distances of the CEJ to the coronal level of epithelial cells and to the alveolar bone crest; the distance of the apical level of epithelial cells to the alveolar bone crest; and the area of inflammatory cell-infiltrated connective tissue. Sample sizes of 6 are used for in vivo studies and a total of 96 rats will be used in this experiment, although the final required sample sizes for the anticipated results will be estimated based upon pilot study data using a type I error of alpha-0.05 and 80% power. Longitudinal repeated measure analysis methodology, including ANOVA with repeated measures and linear mixed models with random effects, are used for analyzing in vivo studies. The post-hoc adjustments for multiple comparisons of the effects of miR-200c on bone resorption are conducted using the Tukey and Holm methods.

Nanoparticles miR-200c delivered using a non-viral vector can be used to prevent and arrest periodontitis-induced bone loss. PEI nanoparticles effectively deliver miR-200c into palatal/interproximal gingival tissue around the $2^{nd}$ maxilla molar, which is evidenced by overexpressed miR-200c in these tissues. Local injection of PEI-miR-200c nanoplexes effectively represses the inflammatory response induced by LPS ligature and inhibit alveolar bone loss by increasing osteoblasts and reducing osteoclasts. The injection dose of PEI-miR-200c nanoplexes is increased if the insufficiency of miR-200c expression in gingival tissue and limited inhibition of bone loss is observed. PEI-miR-200c nanoplexes may also be incorporated into poly (D, L-lactide-co-glycolide) (PLGA) nanospheres. This can be accomplished in two ways: making the PEI-miR-200c nanoplexes first and incorporating them on PLGA during PLGA synthesis or the nanoplexes are absorbed onto the surface of the microspheres after they are prepared. A viral vector may also be employed.

Example 2

Inflammation of the synovial membrane has been demonstrated to be one of the main contributors to cartilage matrix destruction in OA Synovitis can be caused by cartilage matrix debris and/or crystals in synovial fluid. After binding to the debris, macrophages in the synovial membrane of OA joints initially become activated and release cytokines, including IL-1β and TNF. These cytokines may further amplify the inflammatory response by overproducing a number of proinflammatory cytokines, including IL-6, IL-8, and RANTES, in synoviocytes, macrophages, and chondrocytes through NF-kB pathways. The overproduced cytokines subsequently activate bone/cartilage metabolism mediators, including RANKL, RANK, OPG, and PGE2, and stimulate the production of OA-associated catalytic enzymes, including ADAMTS-4, and MMP-1/9/13. The proinflammatory cytokines induced by NF-kB signaling also contribute to progressive chondrocyte proliferation and develop chondrocyte hypertrophy. miR-200c is a member of the miR-200 family that is found to be down-regulated in the inflammatory signaling pathway mediated by IL-6. miR-200c has also been found to potentially inhibit NF-kB activation and IL-8 expression in leiomyoma smooth muscle cells. Preliminary studies showed that miR-200c overexpression effectively reduced IL-8 by targeting IL-8 3'UTR in human preosteoblasts. miR-200c delivered using polyethyleneimine (PEI) effectively inhibits IL-6 and IL-8 (PS-2) in human primary periodontal ligament fibroblasts after exposure to bacterial endotoxin.

miR-200c Inhibits IL-8 by Targeting IL-8 3'UTR miR-200c was transduced into human embryonic palatal mesenchyme cells (HEPM), a preosteoblast cell line, using lentiviral vectors. Scrambled miRs were used as controls. The miR-200c expression in the cells after transduction with miR-200c is 15.9±0.1 (delta/delta Ct) higher than that of controls (FIG. 1). The HEPM cells with miR-200c or scrambled miRs in DMEM medium were cultured with or without bacterial endotoxin lipopolysaccharides (LPS) supplement (1 μg/mL) (Lonza N-185) up to 32 hours. The amounts of IL-8 in the culture medium were analyzed using a Luminex®-X100 Analyzer (Millipore Corp). FIG. 1 shows that the amounts of IL-8 in culture medium of HEPM cells with miR-200c overexpression are dramatically lower than that of HEPM cells with scrambled miRs at each time point LPS supplement increased the amount of IL-8 in HEPM cells with scrambled miRs starting after 4 hours. However, the cells with miR-200c produced much less IL-8 than that of controls even after they were exposed to LPS. FIG. 1 also summarizes the outcome of the luciferase reporter assay of IL-8 3' UTR after transfection with miR-200c. Normalized luciferase activity of the 3' UTR IL-8-luciferase reporter with empty plasmid or miR-200c shows loss of luciferase activity with expression of miR-200c. There is no loss of luciferase activity when the IL-8 3'UTR is mutated.

miR-200c Delivered Using PEI Inhibits IL-6 and IL-8 in Human Primary Periodontal Cells Plasmid miR-200c was incorporated into PEI to form nanoplexes at an N/P ratio of 10:1 [ratio of the total number of end amine groups (N) of PEI and the total number of DNA phosphate groups (P)]. The complexes were prepared by adding 50 μL PEI solution to 50 μl miR-200c (10 μg) solution and mixed for 30 seconds. The mixture was then incubated at room temperature for 30 minutes to allow complex formation between the positively charged PEI and the negatively charged plasmid DNA. The encapsulation efficiency and plasmid miR-200c condensation within the complex were elucidated using spectrophotometry and gel electrophoresis, respectively. In order to test the transfection efficiency, 1, 5, and 10 μg/per well PEI-miR-200c nanoplexes was added to the medium of cultured human primary periodontal fibroblasts (PLFs) in 6-well plates. PEI-empty vector (10 μg) was used as a control. No cytotoxicity of miR-200c-PEI nanoplexes in the dose range we used was observed. After 48 hours, overexpression of miR-200c in a dose-dependent manner in the cells treated with PEI-miR-200c nanoplexes was confirmed using real-time PCR. To test the function of miR-200c, PEI-miR-200c nanoplexes were added to human PLFs in a 6-well plate at 0.5, 5, 10 μg/per well. PEI alone and PEI with empty vectors at the same amounts were used as controls. After 3 days of transfection, the cells were exposed to LPS (1 ug/mL) for 32 hours. The concentrations of IL-6 and IL-8 in the media of cells with miR-200c are significantly lower compared to controls.

The Function of miR-200c on OA-Related Proinflammatory and Bone/Cartilage Metabolism Factors Normal human primary synoviocytes (HS, ScienCell), macrophages (Celprogen), and articular chondrocytes (NHAC-kn, Lonza) are purchased commercially. The cells are treated with PEI alone, miR-200c alone, PEI-miR-200c nanoplexes, and PEI-empty vector nanoplexes at 1, 2, 5, 10 μg at an N/P ratio of 10. The expression of miR-200c with different treatments is evaluated using real-time PCR. After 2 days of transfection, each cell type ($10^5$) is cultured in 2 ml DMEM medium supplemented with or without IL-1β (0.1 ng/mL). A small portion of culture medium (300 μL) of cells with different treatments are collected at 0, 1, 2, 4, 6, 12, 24, and 32 hours. The cells are collected after 32 hours. The amounts of inflammatory chemokines (IL-8, RNTES), cytokines (IL-1β, TNF-α, and IL-6), bone/cartilage metabolism mediators (IKBKB, NF-kB p65, RANKL, RANK, OPG, and PGE2), and proteolytic enzymes (ADAMTS-4, and MMP-1/9/13) in the culture medium and cell lysates from each different treatment at each time point are measured using a Luminex®-X100 Analyzer (Millipore) according to the manufacturer's protocol. Real-time PCR is used to quantify the transcripts of proinflammatory molecules and bone/cartilage metabolism mediators.

Chondrocyte Differentiation Affected by miR-200c

IL-8 has been used to induce chondrocyte hypertrophy in vitro to simulate terminal differentiation of chondrocytes in OA. Human primary articular chondrocytes are treated with PEI-miR-200c nanoplexes and controls. The cells then will be cultured in chondrogenic growth medium (CGM, Lonza) supplemented with IL-8 (10 ng/mL) and lysed at 24, 48 and 96 hours. The biomarkers of human chondrocyte hypertrophy including collagen II and X, MMP13, osteopontin, osteocalcin, Indian Hedgehog, Runx2, and VEGF are determined using real-time PCR. The protein level of these biomarkers is quantitated after 1 and 2 weeks using ELISA.

Target Sites of miR-200c in Proinflammatory Molecules and Bone Metabolism Mediators A luciferase reporter assay is used to determine if miR-200c directly targets the 3'UTR of proinflammatory and bone/cartilage metabolism mediators, as wells as proteolytic enzymes of cartilage. The 3'UTR of mediators or enzymes that are repressed by miR-200c is cloned downstream of the luciferase gene in the pGL3 vector (Promega). The PCR-driven overlap extension method is used to mutate the binding site of miR-200c in the 3'UTR of these factors. HEPM cells are fed for 24 hours prior to transient transfection, resuspended in PBS and mixed with 2 µg miR-200c (p-Silencer), (pcDNA3.1) expression plasmids, 0.1 µg reporter plasmid (pGL3) and 0.5 µg β-galactosidase plasmid. Transfected cells are incubated for 48 hours, lysed and assayed for reporter activities and protein content by the Bradford assay (Bio-Rad). Luciferase are measured using reagents from Promega. β-galactosidase are measured using Galacto-Light Plus reagents (Tropix). All luciferase activities are normalized to β-galactosidase activity and shown as mean-fold differences relative to empty luciferase plasmids.

PEI efficiently transfects miR-200c into human primary chondrocytes, synoviocytes, and macrophages. Overexpression of miR-200c effectively inhibits the proinflammatory responses stimulated by PEI. miR-200c overexpression also represses IL-8, RNTES, IL-6, IKBKB, NF-kB p65, RANKL, RANK, and PGE2 in these cells after they are exposed to IL-1β. miR-200c also inhibits the production of proteolytic enzymes, including ADAMTS-4, and MMP-1/9/13. miR-200c overexpression likely can maintain or reduce the transcript and protein level of the biomarkers of chondrocyte hypertrophy after they are stimulated with IL-8. N/P ratios influence the size, surface charge, transfection efficiency, and cytotoxicity of PEI nanoplexes.

Inflammatory processes play a fundamental role in OA. Synovitis, detectable in both early and advanced OA, is associated with increased pain severity and cartilage lesion progression in joints. Inflammation also causes subchondral bone loss. OA-associated proinflammatory cytokines, such as IL-6 and IL-8, impair cartilage repair mechanisms, resulting in chondrolysis. In addition, cytokines, including IL-1β, IL-8, and TNF-α, are involved in nociceptive pathways in OA, inducing persistent mechanical nociceptor hypersensitivity in OA. Therefore, by modulating OA-associated proinflammatory and cartilage/bone metabolism mediators we will effectively inhibit inflammation and catalytic progress of cartilage and relieve joint pain. Since NF-kB transcription factors play critical roles in inflammation, cartilage degradation, cell proliferation, and angiogenesis in OA, blocking NF-kB signaling will be effective against both the chondrolytic (MMP expression) and proinflammatory effects of IL-1β and TNF. miR-200c has exhibited its inhibitory function on NF-kB signal pathways by targeting IKBKB in leiomyoma smooth muscle cells[20]. In addition, our preliminary studies have shown that miR-200c directly targets IL-8 3' UTR and effectively inhibits IL-6 and IL-8 expression. These data strongly indicate that miR-200c can be used to develop a novel therapeutic for OA by targeting NF-kB, IL-8, and IL-6. Although PEI may serve as a non-viral vector for miR-200c, incorporating PEI-miR-200c nanoplexes into degradable nanoparticles will provide a targeted intracellular delivery with controlled release properties. PLGA nanoparticles with surface cationic modification can intracellularly deliver and sustain the release of small interfering RNAs. In addition, PLGA-PEI nanoparticles can be employed to incorporate miR-200c. Intra-articular injection of PLGA-PEI nanoparticles incorporating miR-200c may prevent cartilage degeneration and synovitis in a rat OA model induced by anterior cruciate ligament transection (ACLT). This OA model has been the most widely used because its underlying initiating mechanism is altered mechanical loading, one of the most common causes of secondary OA in humans.

PLGA-PEI Nanoparticles Transfect miR-200a into Human Preosteoblasts

Plasmid miR-200a was incorporated into PEI to form nanoplexes at an N/P ratio of 10. The complexes were subsequently incorporated into the PLGA (50:50, ester end) to make PLGA nanoparticles using double emulsion. The characteristics of the nanoparticles were analyzed. The average size of nanoparticles was 750 nm. The surface charge of complex-loaded nanoparticles was −6 mV. The amount of plasmid miR-200a loaded in PLGA nanoparticles was 1.2 µg pDNA/mg nanoparticles, which was determined by a spectrophotometer (NanoDrop 2000 UV-Vis). In order to test the transfection of miR-200a, 1 mg miR-200a or scrambled miR-loaded PLGA-PEI nanoparticles was added into the medium of cultured HEPM cells. The medium was exchanged the next day to remove extra particles. On Day 3, overexpression of miR-200a in cells treated with miR-200a-loaded nanoparticles was confirmed using real-time PCR, while no expression of miR-200a was detected in cells treated with scrambled miRs.

Animal Model Preparation and Experimental Design 8-week-old male Sprague Dawley (SD) rats are commercially purchased from Charles River Laboratories. PLGA-PEI nanoparticles incorporating miR-200c will be prepared. Under general anesthesia using ketamine and xylazine, the skin is prepped with a topical antiseptic, and a 1 cm midline incision is made in the skin laterally to the right knee joint. After the joint capsules are opened, the ACL is transected using a surgical scalpel. The capsular incision is closed using 4-0 Vicryl sutures and the skin is closed with staples. In all animals, the right knee joint is the operated joint and the left knee joint is the ACL-intact control joint. The animals then are randomly divided and receive different treatments of PLGA-PEI nanoparticles incorporating miR-200c or controls. Nine treatment groups are designed for this study, including: 1) sham operation; 2) no treatment; 3) empty PLGA-PEI (1 mg); 4) 0.1 mg PLGA-PEI particles containing about 0.12 µg empty vector; 5) 1.0 mg PLGA-PEI containing 1.2 µg empty vector, 6) 0.1 mg PLGA-PEI particles containing about 0.12 µg miR-200c; 7) 1.0 mg PLGA-PEI containing 1.2 µg miR-200c 8) PEI-miR-200c (1.2 µg); 9) plasmid miR-200c (1.2 µg). The PLGA-PEI-miR-200c nanoparticles are suspended in 40 µL saline and intra-articularly injected using a 25-gauge syringe. Overexpression of miR-200c in synovial membranes and cartilages after intra-articular injection is confirmed using real-time PCR. The rats with different treatments are euthanized after 4 and 8 weeks and both knees from each animal are harvested. Serum samples and synovial fluid lavages are obtained from both knees of each animal to measure the biomarkers of inflammation and bone/cartilage metabolism mediators. The synovial tissue inflammation and degeneration of cartilage and bone of joints are evaluated using µCT and histomorphometry.

Analysis of Proinflammatory and Bone/Cartilage Metabolism Mediators

Serum is obtained by intracardiac aspiration and centrifuged at 10,000 g at 4° C. for 20 minutes to remove cellular debris. The aliquots of serum are then frozen. After euthanasia, each hindlimb is disarticulated and 100 µl of isotonic saline will be injected intra-articularly into the knee joint. The knee is manually cycled through flexion and extension ten times to distribute the fluid throughout the joint. The fluid will be then aspirated from the joint and frozen at −80° C. The proinflammatory cytokines and bone/cartilage metabolism mediators in serum and synovial fluid lavage, including TNF-α, IL-1, IL-6, IL-8, RANTES, NF-kB p65, RANKL, RANK, OPG, PGE2, ADAMTS-4, and MMP-1/9/13, are quantitated using the Luminex assay according to the manufacturer's protocol.

Assessment of Subchondral Bone Resorption

The specimens are immersed in 10% formalin for 72 hours after harvest. µCT imaging is performed on the specimens of knee joints using a cone-beam µCT system (µCT40, Scanco Medical AG). Specimens are scanned in 70% ethanol at 55 kVp and 145 µA with a voxel size of 10 µm and an integration time of 300 ms. Analysis is performed using a constant 3.5 mm diameter circular region of interest that is placed in the subchondral zone of the femoral and tibial condyles and spanned a total of 50 reconstructed slices. µCT data is acquired and reconstructed using the manufacturer's software. Subchondral bone volume and bone mineral density are calculated.

Histomorphometric Analysis of Synovial Inflammation and Cartilage Degeneration

After µCT analysis, synovial tissues with patella but without menisci are removed, dehydrated, embedded in paraffin, and cut into 5 µm-thick sections. After hematoxylin eosin (H&E) staining, the severity of acute inflammatory changes is quantitated histologically by grading several measures of joint inflammation on a scale of 0 to 3 as follows: nil (Grade 0), mild (Grade 1), moderate (Grade 2), severe (Grade 3). The following variables are assessed histologically: (1) subsynovial cellular infiltration with polymorphonuclear leukocytes; (2) synovial lining cell hyperplasia; (3) patella erosion; (4) peri-articular soft tissue cellular infiltration. To histologically assess degeneration of bone and cartilage, the joint specimen will be decalcified, embedded in paraffin, and trimmed to produce coronal sections in the weight bearing regions of the femoral condyles and tibial plateau using a rotary microtome. The samples are sectioned 5 microns thick and stained with Safranin-O/fast green. The slides are viewed and photographed under light microscopy. The Osteoarthritis Research Society International (OARSI) histopathology grading will be used to evaluate cartilage degeneration. OARSI scores are assigned by four experienced independent examiners who are blinded to the treatment group.

Statistical Analysis

The primary outcomes include the proinflammatory and bone/cartilage metabolism mediators in serum and synovial fluid lavage, subchondral bone volume and mineral density, synovial inflammation score, as well as OARSI scores of cartilage degeneration in ACLT rats receiving different treatments. Sample sizes of 6 are used for in vive studies and a total of 108 rats are used in this experiment, although the final required sample sizes for the anticipated results are estimated based upon pilot study data using a type I error of alpha=0.05 and 80% power. Longitudinal repeated measure analysis methodology, including ANOVA with repeated measures and linear mixed models with random effects, are used for analyzing in vivo studies. The post-hoc adjustments for multiple comparisons of the effects of miR-200c on inflammation and bone/cartilage degeneration are conducted using the Tukey and Holm methods.

Summary miR-200c delivered using biodegradable nanoparticles can be used to prevent OA-associated cartilage and bone degeneration by repressing inflammation. Intra-articular injection of PLGA-PEI nanoparticles incorporating miR-200c effectively delivers miR-200c intracellularly into synovial and cartilage tissues in vivo and overexpress miR-200c for a sustained period of time. Intra-articular injection of PLGA-PEI-miR-200c effectively reduces the proinflammatory and cartilage metabolism mediators in synovial fluid lavage induced by ACLT. The injection also prevents ACLT-induced bone volume and mineral density reduction in subchondral bone of the femoral and tibial condyles. In addition, PLGA-PEI-miR-200c injection maintains the cartilage thickness and characteristics in the femoral condyles and tibial plateau and prevent cartilage degeneration induced by ACLT. A 75:25 ratio of PLGA may also be employed to slow the degradation rate and adjust the dose of PLGA-PEI-miR-200c nanoparticles. The surface of PLGA nanoparticles may be modified using cationic PAMAM dendrimers to increase uptake efficiency of nanoparticles. A viral vector may also be employed.

Example 3

Recent studies found that miR-200c can repress the expression and activity of multiple proinflammatory factors, including NF-kB and IL-8. These proinflammatory factors have been demonstrated to impair bone formation by reducing differentiation of osteoblasts and their progenitor cells. Inhibition of NF-kB was reported to improve osteogenic differentiation and bone formation. In addition, miR-200c targets Noggin 3'UTR and down-regulates Noggin expression in dental epithelial cells. Noggin is a secreted protein that binds and inactivates a number of BMPs, including BMP-2, 7. While BMP-2 may induce Noggin expression, inhibition of Noggin has been demonstrated to enhance BMP-2-induced bone formation in vivo. However, the in vitro effect of Noggin inhibition on osteogenic differentiation is vanes with cell type. For instance, treatment with siRNA of Noggin was reported to improve osteogenic differentiation induced by BMP-2 in human adipose-derived stem cells, while the Noggin inhibition reduces osteogenic differentiation in human bone marrow MSCs. Noggin also was reported to improve osteogenic differentiation of human bone marrow MSCs by induction of anabolic inflammation in vitro. It was observed that overexpression of miR-200c can effectively improve osteocalcin (OCN) and calcium content in human preosteoblasts. MiR-200c overexpression also effectively improve Runx-2 expression in human bone marrow MSCs and down-regulate Noggin expression. These data strongly indicate that miR-200c may improve osteogenic differentiation in human bone marrow MSCs, however, its molecular function on osteogenic differentiation is not, or not completely, mediated by Noggin inhibition. miR-203 can modulate BMP signaling by targeting BMPER. This indicates that miR-200c may also regulate osteogenic differentiation via modulating BMP-related signaling.

PEI nanoparticles have been used as a non-viral vector for gene delivery due to their "proton-sponge" effect and high transfection efficiency. PEI was shown to be effective in transfecting cells even in the presence of serum. N/P ratios [ratio of the total number of end amine groups (N) of PEI and the total number of DNA phosphate groups (P)] influence the size, surface charge, transfection efficiency and cytotoxicity of PEI nanoplexes. PEI nanoparticles can be employed as a non-viral vector to efficiently transfect miR-200c into human MSCs.

miR-200c Overexpression Enhances Osteogenic Differentiation in Human Preosteoblasts and MSCs miR-200c was transduced into human embryonic palatal mesenchyme cells (HEPM), a preosteoblast cell line, using lentiviral vectors. The cells with scrambled miRs were used as controls. The expression of miR-200c in the cells after transduction with miR-200c is 15.9±0.1 (delta/delta Ct) higher than that of controls. The cells were then cultured in DMEM medium supplemented with β-glycerophosphate (1 mM) and ascorbic acid (5 mg/ml) up to 2 weeks. After one week, OCN transcripts measured using real-time PCR in miR-200c overexpression cells was 30-fold higher than control cells with scrambled miRs. The protein level of OCN measured using a ELISA kit (Invitrogen) was also 3-4 times higher in miR-200c cells than that of control cells after two weeks. The calcium content in miR-200c cells was 3 times higher than that of cells with scrambled miRs.

A non-viral vector (X-tremeGENE HP DNA Transfection Reagent, Roche) was initially used to transfect miR-200c into human bone marrow MSCs. Plasmid miR-200c (3 µg) was used to transfect $10^5$ cells in a 6-well plate according manufacturer's instruction. Empty vector was used as a control. The cells were subsequently cultured in osteogenic differentiation medium consisting of DMEM with dexamethasone (100 nM), ascorbic acid (5 mg/ml) and glycerophosphate (5 mM) up to one week. Overexpression of miR-200c (8.5±1.2, delta/delta Ct) was found in the cells with miR-200c transfection, compared to the cells with empty vector transfection or without transfection. Furthermore, Noggin expression was approximate 3-fold lower in the cells with miR-200c. Runx2/cbfa-1 expression in the MSCs with miR-200c is about 5-fold higher than that of controls.

PEI Nanoparticles Deliver miR-200a into Human Preosteoblasts.

Plasmid miR-200a was incorporated into PEI to form nanoplexes at an N/P ratio of 10:1. The complexes were prepared by adding 50 µl PEI solution to 50 µL miR-200a (10 µg) solution and mixed for 30 seconds. The mixture was then incubated at room temperature for 30 min to allow complex formation between the positively charged PEI and the negatively charged plasmid DNA. In order to test the transfection efficiency, 1, 2, and 4 µg PEI-miR-200a nanoplexes were added into the medium of cultured HEPM cells. PEI-loaded scrambled miRs were used as controls. The medium was exchanged the next day to remove extra nanoplexes. On Day 3, real-time PCR analysis showed that 6.58±0.02, 7.15±0.06, and 10.8±0.1 (delta/delta Ct) miR-200a overexpression were detected in the cells treated with PEI-miR-200a at different doses, respectively. MiR-200a expression was not detected in the cells treated with PEI-scrambled miRs.

Synthesis and Characterization of PEI-miR-200c Nanoplexes

In order to optimize the biocompatibility and transfection efficiency, PEI nanoparticles encapsulating plasmid miR-200c with a range (1, 5, 10, 15, and 20) of N/P ratios are synthesized. The effect of N/P ratio of PEI-miR-200c nanoplexes on their encapsulation efficiency, cytotoxicity, and transfection efficiency will be thoroughly evaluated. After the synthesis of PEI-miR-200c nanoplexes, the size and polydispersity of the synthesized nanoplexes are determined using dynamic light scattering and transmission electron microscopy (TEM) Zeta potential (surface charge) that is based on the electrophoretic mobility of the nanoplexes using folded capillary cells are determined using the laser scattering method. The encapsulation efficiency and plasmid miR-200c condensation within the complex are elucidated using spectrophotometry and gel electrophoresis, respectively.

Biocompatibility and Transfection Efficiency of PEI-miR-200c Nanoplexes

To test cytotoxicity, human bone marrow MSCs will be seeded at 10,000 cells/per well in a 96-well plate and treated with PEI-miR-200c nanoplexes at different N/P ratios. Untreated cells act as controls while cells treated with high dose PEI will be used as a positive control to induce cytotoxicity. The same amount of PEI-empty vector is included as a control. The cytotoxicity of PEI-miR-200c nanoplexes is determined using MTT assay after 4 and 24 hrs. To test transfection efficiency human MSCs are seeded at $10^5$ cells/per well in a 6-well plate and treated with 1 µg of PEI-miR-200c nanoplexes with different N/P ratios. The expression of miR-200c is determined by real time-PCR after 48 hours.

Osteogenic Differentiation of Human MSCs by miR-200c Overexpression

Human bone marrow MSCs are treated with PEI alone, miR-200c alone, PEI-miR-200c nanoplexes, and PEI-empty vector nanoplexes at 1, 2, 5, 10 µg at a N/P ratio of 10. The N/P ratio of PEI-miR-200c are adjusted. The cells are then cultured in osteogenic medium consisting of DMEM medium supplemented with ascorbic acid (5 mg/mL) and glycerophosphate (5 mM) and lysed at 48, 72 and 96 hrs. Noggin, BMP-2, BMP-7, BMPER, alkaline phosphatase (ALP), Runx2, collagen type I, OCN, bone sialoprotein (BSP), and Osterix transcripts are determined using real-time PCR. In addition, ALP activity, the protein of OCN, BSP, collagen type I and calcium content of transfected MSCs are quantitated after 1 and 2 weeks.

Molecular Function of miR-200c in Human MSCs

MSCs are treated with PEI-miR-200c nanoparticles at 5 µg for 4 hours and the cells are exposed to osteogenic medium. The dose of PEI-miR-200c will be adjusted based on dose dependent studies. The transcript and protein levels of β-catenin, Wnt-3A, Wnt-7A, Smad 1/5/8 are measured using real-time PCR and western blot after 1 and 7 days, respectively. These signal pathways have been demonstrated to interact with BMPs in osteogenic differentiation. For RNA-seq 1 µg RNA and the TruSeq Stranded Total RNA Library Prep kit (Illumina) are used to perform reverse transcription with bar-coded primers, complementary DNA amplification, and 100×100 paired ended sequencing with Illumina HiSeq 2000. Quality control of the obtained reads and mapping to the human reference genome (GRCm38/mm10) is performed using the combination of the Galaxy (https://main.g2.bx.psu.edu/) web-based analysis suite and in-house Perl scripts. Cufflink tool set will be used to analyze mapped reads to identify significant changes in gene expression. The low expression transcripts (less than 10 reads in all samples) is filtered out, and P values will be adjusted using a threshold for false discovery rate (FDR) ≤0.001. Differentially expressed transcripts are identified using threshold of fold change≥2 and FDR≤0.001. The differentially expressed genes are further used for hierarchical clustering performed using Cluster 3.0. Java Treeview is used for visualization ( ). Gene ontology category enrichment is assessed using GOrilla (http://cbl-gorilla.cs.technion.ac.il/).

Summary

Figure 9H:
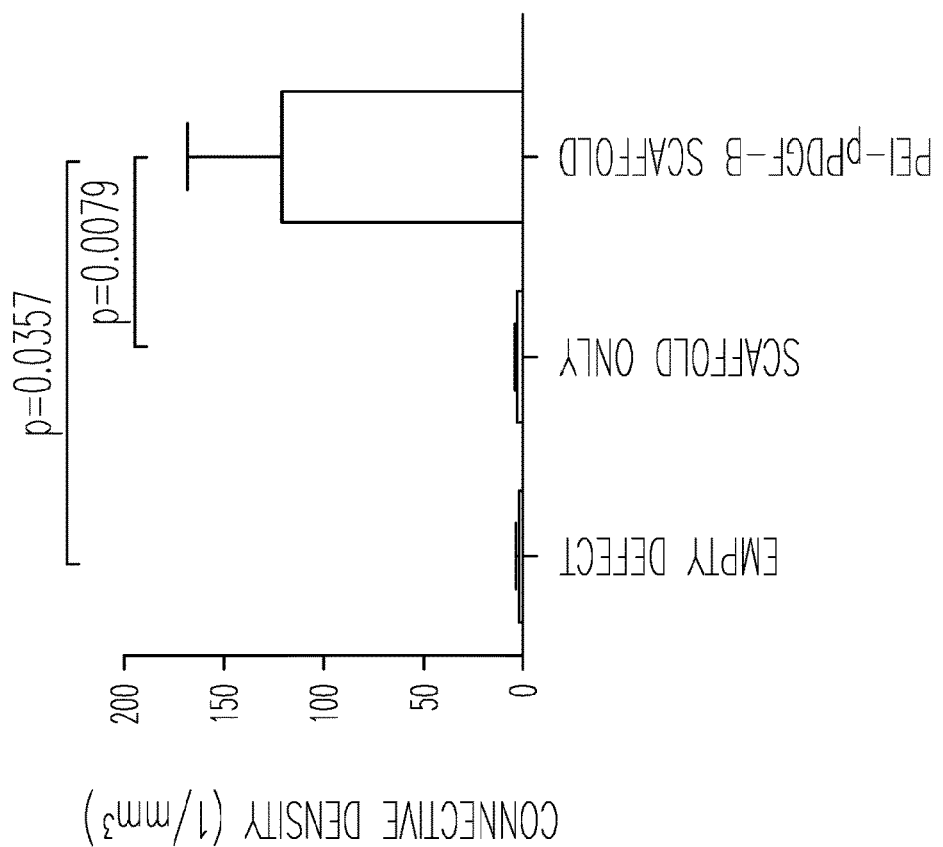
FIG. 9. Evaluation of in vivo bone formation: representative μCT scans showing the level of regenerated bone tissue after 4 weeks in empty defects (A, D, n=3), empty scaffolds (B, E, n=5) and PEI-pPDGF-B complex-loaded scaffolds (C, F, n=5), assessment of regenerated bone volume fraction (G), bone connectivity density (H) in different groups.
Figure 9G:
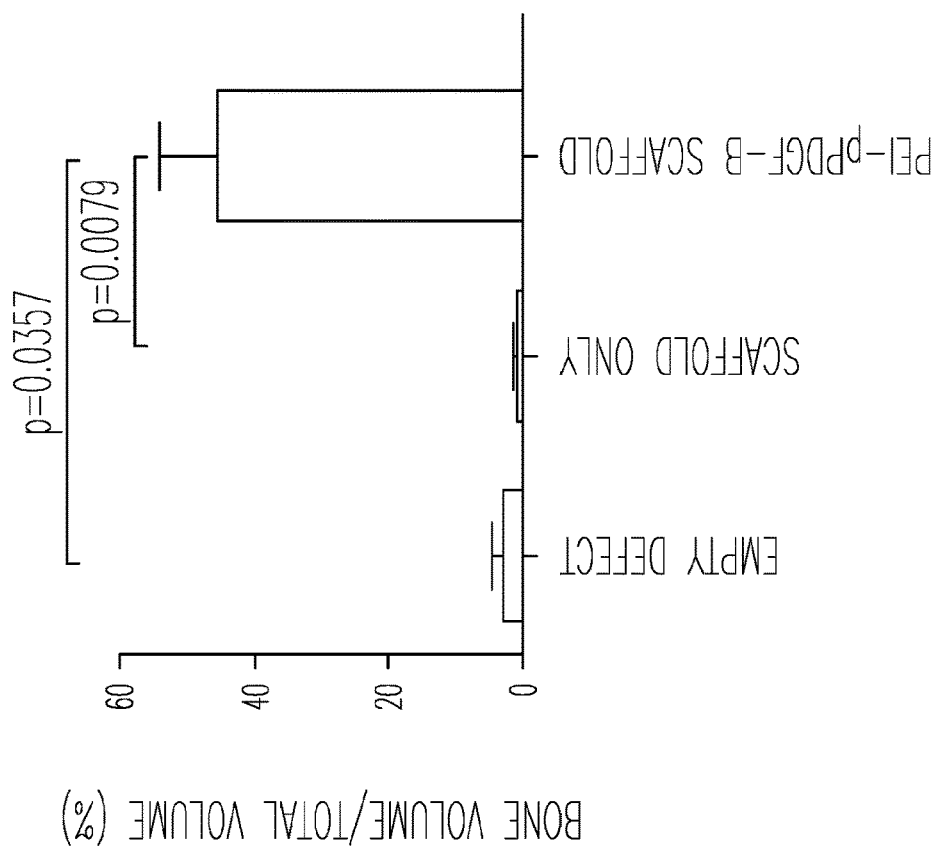

PEI nanoparticles can efficiently intracellularly deliver miR-200c into human MSCs and significantly increase miR-200c expression. mRNA expression and protein level of the specific biomarkers of osteogenic differentiation and bone formation is likely to be significantly higher in cells transfected with miR-200c, compared to other treatments. miR-200c delivered using PEI nanoparticles will likely enhance osteogenic differentiation of human MSCs. The results of β-catenin, Wnts and Smads will determine the role of miR-200c modulation in BMP-related signal pathways during osteogenic differentiation. RNA-seq will provide the expression variations of total RNA and small RNA in human MSCs with miR-200c overexpression. RNA-Seq also will elucidate the potential cellular pathway alterations in MSCs with overexpressed miR-200c and gene expression level changes during osteogenic differentiation. The NIP ratio of the PEI-miR-200c nanoplexes and miR-200c concentration within the nanoplexes may impact transfection efficiency and cytotoxicity. The nanoplexes may also be incorporated into poly (D, L-lactide-co-glycolide) (PLGA) microspheres. This can be accomplished in two ways: making the PEI-miR-200c nanoplexes first and incorporating them on PLGA during PLGA synthesis or the nanoplexes will be absorbed onto the surface of the microspheres after they are prepared Calvarial bone defects in a rat model have been extensively used to evaluate the efficacy of synthetic materials on bone formation in vivo. This animal model is used to determine the efficacy of PEI-miR-200c nanoplexes on bone regeneration in vivo. A collagen sponge will be used as a scaffold to carry and release nanoplexes. The same delivery system can induce a significantly higher bone regeneration in a 5-mm calvarial defect in rats (FIG. 9).

A Rat Model to Test the In Vivo Efficacy of PEI-miR-200c on Bone Regeneration

PEI-miR-200c nanoplexes at an N/P ratio of 10 are synthesized. The nanoplexes are then injected into a collagen sponge (8 mm-in-diameter and 2 mm thickness) and freeze-dried. A total of 144 twelve-week old male Fisher 344 rats (about 200 to 250 grams) are purchased. Under general anesthesia using ketamine and xylazine, an incision is made along the sagittal plane of the cranium and a full thickness flap is reflected to expose the calvarial bone. Using a trephine bur, a single circular defect of 8 mm in diameter is created under saline irrigation without damaging the dura mater. The animals are randomly assigned to one of 12 groups (See Table 3 below). Collagen sponges loaded with PEI-pPDGF nanoplexes are used as a positive control that has been demonstrated to significantly induce bone regeneration). The sample size per group is 6. Alter implantation, the periosteum and the skin are secured with sutures. Animals are sacrificed alter 4 and 8 weeks and samples are harvested for image and histological analyses.

TABLE 1

Treatment groups for in vivo regenerative studies

| Groups | Description |
| --- | --- |
| I | Empty defect |
| II | Collagen scaffold alone |
| III | miR-200c (1 µg) in collagen scaffold |
| IV | miR-200c (10 µg) in collagen scaffold |
| V | miR-200c (50 µg) in collagen scaffold |
| VI | PEI-empty vector (1 µg) in collagen scaffold |
| VII | PEI-empty vector (10 µg) in collagen scaffold |
| VIII | PEI-empty vector (50 µg) in collagen scaffold |
| IX | PEI-miR-200c (1 µg) in collagen scaffold |
| X | PEI-miR-200c (10 µg) in collagen scaffold |
| XI | PEI-miR-200c (50 µg) in collagen scaffold |
| XII | PEI alone in collagen |

Assessment of Bone Regeneration

Bone regeneration is evaluated using micro-computed tomography (ICT), histology, and histomorphometry. After euthanasia, calvarial tissue Is harvested, fixed in buffered formalin and scanned in 70% ethanol using a cone-beam µCT system at 55 kVp and 145 mA with a voxel size of 10 µm. Analysis is performed using a constant 8 mm circular region of interest to determine bone volume/tissue volume and connectivity density. After µCT analysis, the specimens are decalcified and histological analysis is performed on the 5 µm sections in the central portion of the wound. New bone area (within the defect area) is calculated using optical images of the stained sections and image analysis software.

Statistical Analysis

The primary outcomes are percentage new bone volume derived from µCT analysis and new bone area derived from histomorphometric analysis. Two-way analysis of variance (ANOVA) is used to assess effects of treatment and time, including possible interactions, using a Type I error level of 0.05. Pairwise comparisons among treatments within a specific time are assessed using the Holm modification of the Bonferroni adjustment for multiple comparisons in conjunction with an overall Type I error level of 0.05. In the presence of interaction. pairwise comparisons are made a time point. The sample size of 6 animals for each combination of time and treatment was obtained based on planned multiple comparisons.

There is significantly increased bone formation in the calvarial defects treated with PEI-miR-200c delivered in a collagen scaffold, compared to all the other groups tested.

Example 4

Materials and Materials
Materials

Plasmids, including psPAX2, pMD2G, and those carrying miR-200c, scrambled miRs, or the empty vector were purchased from Addgene. HEK 293T and HEPM cells were purchased from ATCC. Primary human bone marrow MSCs and periodontal ligament fibroblasts were purchased from Stemcell Preparation of Lentiviral Vectors Carrying miR-200c Lentiviral vectors carrying plasmid miR-200c or scrambled miRs were produced by transfecting psPAX2, pMD2G, and plasmid carrying miR-200c or scrambled miRs into HEK 293T cells using a standard $CaCl_2$ method. Briefly, 1.8 µg of psPAX2, 1.2 µg of pMD2G, and 4.2 µg of plasmid miR-200c or scrambled miRs were mixed with 14 µL of 2 M $CaCl_2$, and 2 µL of 10 mg/mL polybrene in HBS buffer (pH 7.05) to constitute the transfection solution. The transfection solution was then applied to culture plates containing HEK 293T cells at 20-30% confluence, and replaced with fresh medium after 24 hours. Supernatant containing the miR-200c lentivirus was then harvested after 72 hours and filtered through a 0.45-μm sterile syringe.

Transduction of HEPM Cells with miR-200c Using Lentivirus

In order to transduce the HEPM cells with plasmid miR-200c or scrambled miRs, the lentiviral vector carrying miR-200c (about $10^8$ TU/mL) was added to a suspension of HEPM cells and incubated overnight. For 3 days, the medium was replaced each day with fresh medium containing the same amount of lentivirus carrying miR-200c or scrambled miRs after which the cells were collected. The cells were then sorted by flow cytometry for the presence of green fluorescent protein (GFP), and the positive cells were analyzed for the proliferation, osteogenic capacity, and proinflammatory mediators.

Analysis of Proliferative and Osteogenic Capacity of HEPM Cells

HEPM cells infected with miR-200c or scrambled miRs were cultured in Dulbecco's Modified Eagle Medium (DMEM) containing 10% fetal bovine serum (FBS). The doubling time of the cells was measured to determine the proliferation rate. To analyze osteogenic capacity, the cells were cultured with osteogenic medium consisting of DMEM supplemented with 1 mM β-glycerophosphate and 0.05 mM ascorbic acid-2-phosphate, for up to 2 weeks. The cells transduced with the scrambled miRs served as controls. Transcripts of OCN were quantified using real-time PCR and calcium content was quantified using commercially available kits, as in our previous studies. Primers and probes were designed using the Primer Express software (Applied Biosystems, Foster City, Calif.). The forward and reverse primers and real-time probes for OCN was Construction of miR Expression and Inhibitor Plasmids In order to construct a miR expression plasmid, miR genes were PCR amplified that include approximately 100 bp upstream and 100 bp downstream sequence flanking the approximately 80 bp stem loop sequence. The PCR product was ligated into pSilencer 4.1 vector (Ambion) digested by BamHI and HindIII. The construction of miR inhibitor plasmids has been purchased from NaturemiRI (NaturemiRI.com). To construct different designs of miR inhibitors for miR-200c and miR-17-18, we annealed and ligated the miR-200c or miR-17-18 binding sites with a central bulge flanked by different sequences into pLL3.7 vector (Addgene) digested with HpaI and XhoI. To construct the miR inhibitor clone vector, we replaced the miR-200c binding site with two BsmBI sites in the most effective inhibitor design. AscI and PmeI sites were inserted between ApaI and XbaI sites before the U6 promoter. A SmaI site was inserted before XhoI after the polIII terminator. This vector is termed PMIS-empty vector (EV) for plasmid of miR inhibitor. After digestion by BsmBI, pmiRi can be used to done different miR inhibitors into it after annealing and ligation of different miR binding sites with a central bulge.

Transfection of miR-200c Using PEI into Primary Human Cells

Plasmid DNA containing miR-200c was incorporated into PEI to form nanoplexes at an N/P ratio of 10:1 according to our previous studies. Briefly, the complexes were prepared by adding 50 μl PEI solution to 50 μl miR-200c (10 μg) solution and mixed for 30 seconds. The mixture was then incubated at room temperature for 30 minutes to allow complex formation between the positively charged PEI and the negatively charged plasmid DNA. The encapsulation efficiency and plasmid miR-200c condensation within the complex were elucidated using spectrophotometry and gel electrophoresis, respectively as in our previous studies (Chang et al., 2009; Chang et al., 2013). In order to test the transfection efficiency, primary human periodontal ligament fibroblasts and bone marrow MSCs cultured with DMEM medium were seeded in 6-well plates at 510 cells/well. PEI-miR-200c nanoplexes at different doses (1, 2, 5, and 10 μg/per well) were added into the medium of cultured cells. The medium was exchanged after 4 hours to remove extra nanoplexes and the cells with different treatment were continuously cultured using DMEM medium. After 48 hours the cells with different treatment were harvested using Trizol. Total RNA was collected using miRNeasy Mini Kit (QIAGEN) and cDNA was prepared using TaqMan microRNA reverse transcription kit. miR-200c transcripts were detected using real-time PCR.

Measurement of Proinflammatory Mediators in HEPM Cells and Periodontal Ligament Fibroblasts with Overexpression of miR-200c The HEPM cells with miR-200c or scrambled miRs were placed in DMEM medium at $10^6$ cells/per 25 $cm^2$ tissue culture flask. For periodontal ligament fibroblasts, the cells were placed in DMEM medium at 105 cells/per well and cultured in 6-well plates and subsequently treated with PEI-miR-200c at different concentrations for 4 hours. The cells treated with the same amount of PEI-empty vector sever as controls. The cells were then cultured in DMEM medium for 48 hours. In order to determine the proinflammatory mediators in HEPM cells and periodontal ligament fibroblasts, the cells were cultured using DMEM with or without lipopolysaccharide (LPS) supplement (1 μg/mL) (Lonza N-185). A small portion of culture medium (300 μl) from different cells with different treatments will be collected at different time points up to 32 hours. Chemokine and cytokine concentrations were measured in cell supernatants using Milliplex immunoassays (Millipore, Billerica, Mass. USA) as previously described (Borgwardt et al., 2014). Cell supernatants (25 μL) were incubated with anti-human multi-cytokine magnetic beads at 4° C. for 18 hours before removing unbound material using a magnetic plate washer (ELx405TS, BioTek, Winooski, Vt. USA). Samples were then incubated with anti-human multi-cytokine biotin reporters for IL-6, IL-8, and CCL-5 for one hour at room temperature, streptavidin-phycoerythrin was added, and plates were incubated for an additional 30 minutes. Samples were washed and suspended in sheath fluid before analysis using a Luminex 100 (Austin, Tex.). Standard curves for each cytokine were prepared from 3.20 to 10,000 pg/ml and concentrations of chemokines and cytokines in each sample were interpolated from standard curves (xPonent v3.1, Luminex, Austin, Tex. USA; MILLIPLEX Analyst v5.1, Millipore, Billerica, Mass. USA).

Analysis of Osteogenic Differentiation of Human Bone Marrow MSCs Transfected with miR-200c Human bone marrow MSCs were placed in DMEM medium at $10^5$ cells/per well in 6-well plates and subsequently treated with PEI-miR-200c at 1 μg/per well for 4 hours. The cells were cultured with DMEM medium supplemented with 1 mM β-glycerophosphate and 0.05 mM ascorbic acid-2-phosphate, for up to 2 weeks. Biomarkers of osteogenic differentiation, including ALP and calcium, were quantified using commercially available kits, as in our previous studies. Transcripts of ALP and Runx2 were quantified using real-time PCR. The forward and reverse primers and real-time probes for Runx2 were:

```
5'-CAACAAGACCCTGCCCGT-3',           (SEQ ID NO: 4)

5'-TCCCATCTGGTACCTCTCCG-3',         (SEQ ID NO: 5)
and

5'-CTTCAAGGTGGTAGCCC-3'.            (SEQ ID NO: 6)
```

Luciferase Reporter Assays miR-200c was cloned into pSilenser 4.1 (Life Technologies). Luciferase reporters were generated by inserting 3'UTR DNA fragments into pGL3 CXCR4 vector (Addgene), as previously described. All the cloned constructs were confirmed by DNA sequencing. All plasmids used for transfection were purified by double-banding in CsCL. Luciferase, Bgal and protein concentration assay were done as previously described (Cao et al., 2013). LS-8 cells were cultured in DMEM supplemented with 5% FBS, 5% BGS and penicillin/streptomycin, and transfected by electroporation. Cells were fed and seeded in 60 mm dishes 24 hour prior to transient transfection. Cells were resuspended in PBS and mixed with 2.5 µg of expression plasmid, 5 µg of reporter plasmid and 0.2 µg of SV-40 β-galactosidase plasmid. Transfection was performed by electroporation at 380 v and 950 µF (Gene Pulser XL, Bio-Rad), or using the Lipofectamine 200 (life technologies) transfection reagent. Transfected cells were incubated in 60 mm culture dishes, for 24 hours unless otherwise indicated, and fed with 10% FBS and DMEM. Following lysis, assays for reporter activity (luciferase assay, Promega) as well as for protein content (Bradford assay, Bio-Rad) were carried out. β-galactosidase was measured using the Galacto-Light Plus reagents (Tropix Inc.) as an internal normalizer. For each assay, all luciferase activity was normalized to the mean value of the first experimental group, and is shown as mean±SEM.

Statistical Analysis

All quantitative data were calculated as means±standard deviation. The osteogenic differentiation biomarkers and proinflammatory mediators in HEPM cells, human periodontal ligament fibroblasts, and MSCs with overexpressing miR-200c were analyzed by one-way ANOVA with LSD's post hoc test, using commercially available statistics software (SPSS Inc., Chicago, Ill.), and p values less than 0.05 are considered significant. Each experiment was performed in triplicate.

Results

Figure 10A:
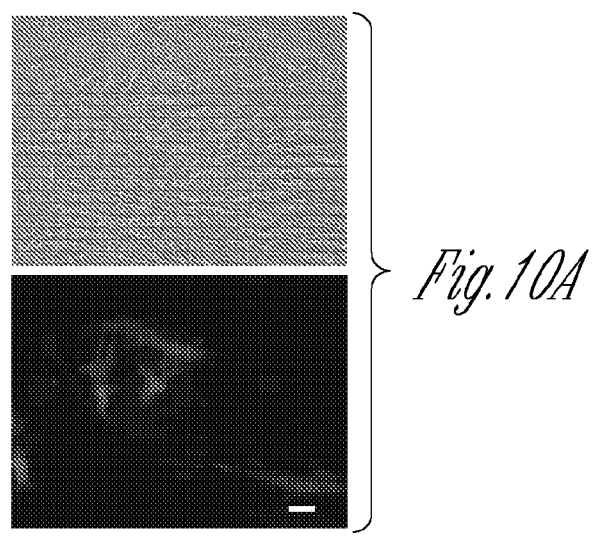
FIG. 10. miR-200c overexpression in HEPM cells and the effects on their proliferation. A) Microphotographs of HEPM cells after infection of with miR-200c under phase-contrast (upper panel) and fluorescent microscopes (lower panel). Bar-10 μm. B) Expression of miR-200c in HEPM cells transfected with miR-200c or a scrambled miRs. C) The doubling time of HEPM cells in the context of miR infection.
Figure 10B:
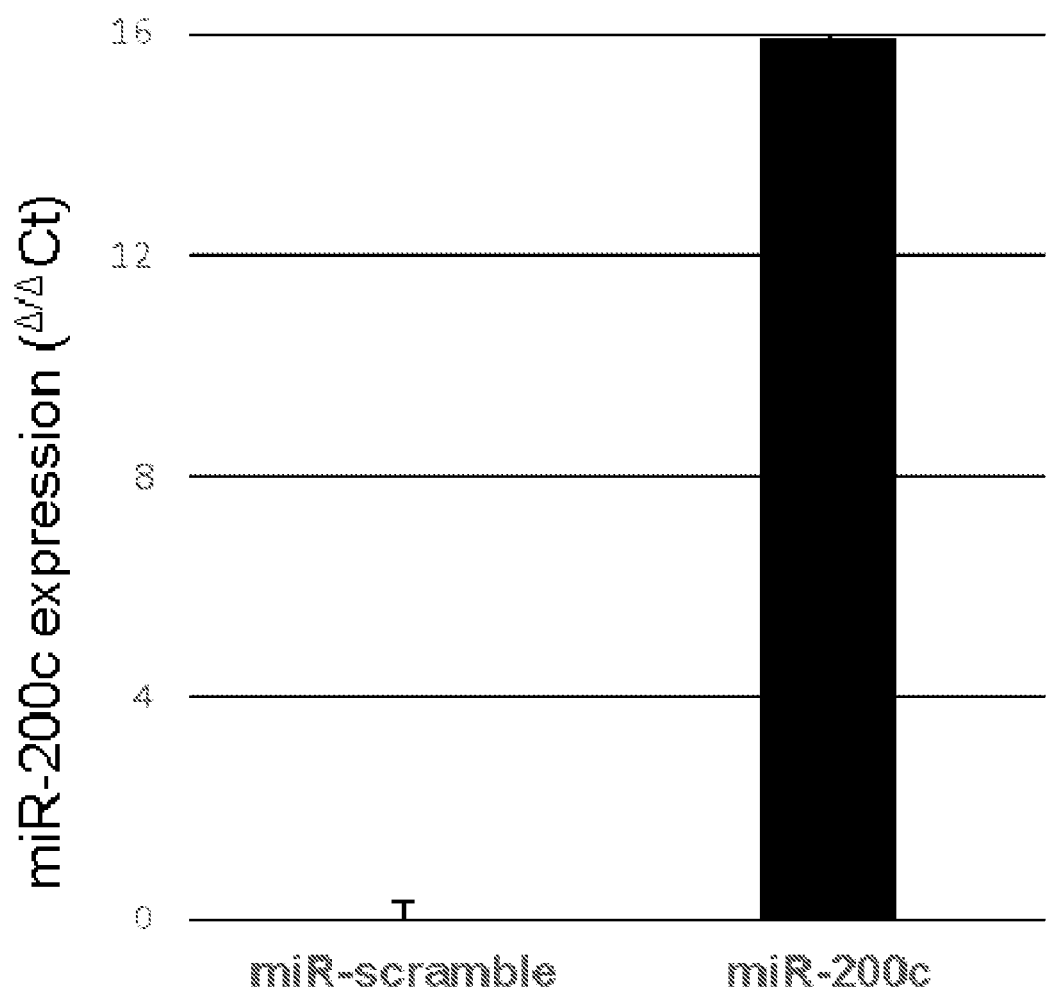
Figure 10C:
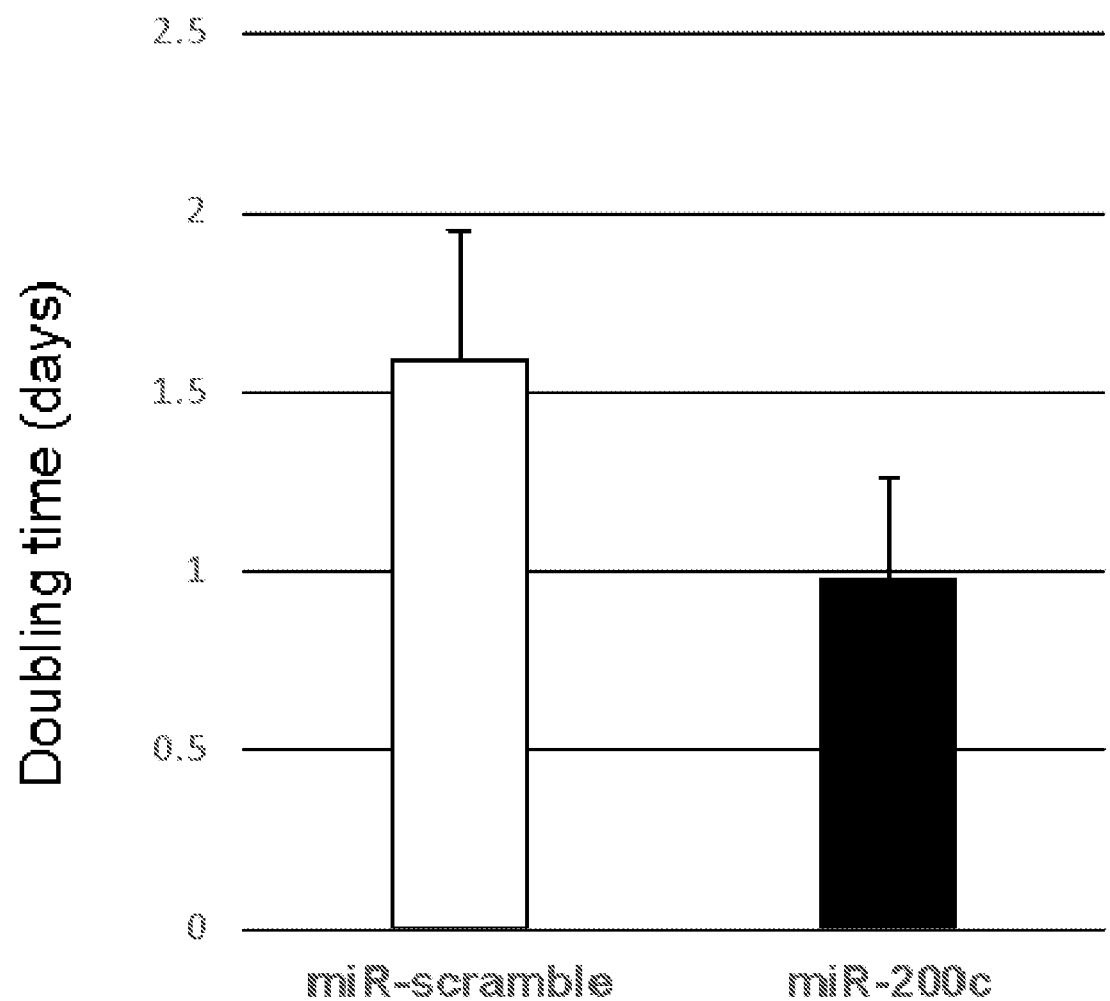
Figure 11A:
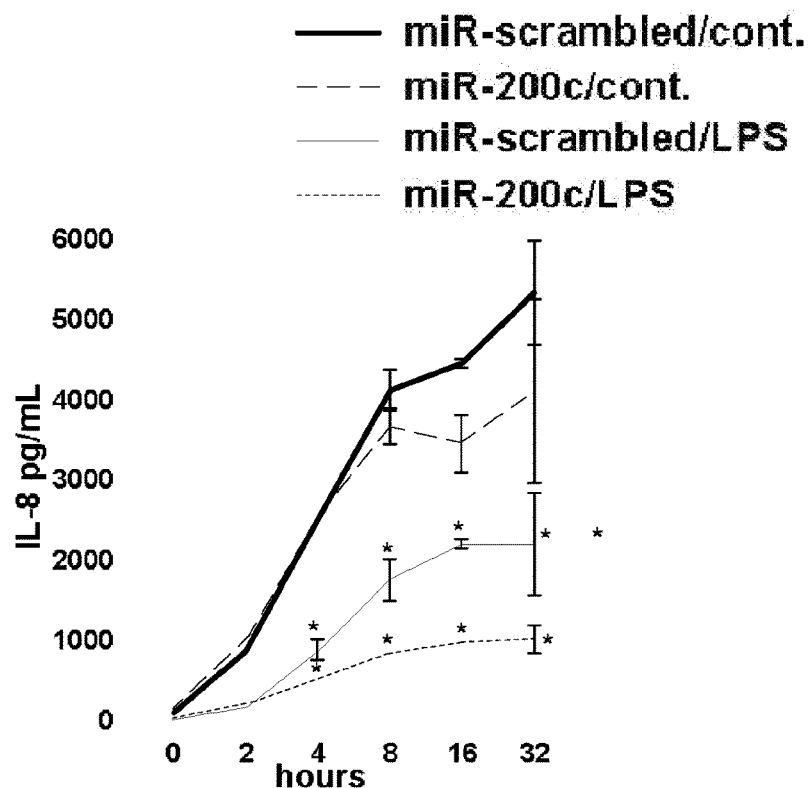
FIG. 11. miR-200c modulates proinflammatory and bone metabolism mediators and increases osteogenic biomarkers in human preosteoblasts. A) the amounts of IL-8 secreted by HEPM cells with miR-200c or scrambled miRs cultured in DMEM supplemented with or without LPS at different time points; B) and C) the amounts of IL-6 (B) and CCL-5 (C) secreted by HEPM cells with miR-200c or scrambled miRs cultured in DMEM supplemented with or without LPS after 24 hours; D) the amounts of OPG secreted by HEPM cells with different miRs cultured in DMEM supplemented with or without LPS after 32 hours. E) and F) the amounts of the transcript of OCN (E) and calcium content (F) in HEPM cells with miR-200c or scrambled miRs cultured in DMEM supplemented β-glycerophosphate and ascorbic acid after 1 and 2 weeks, respectively. *: p<0.05.
Figure 11B:
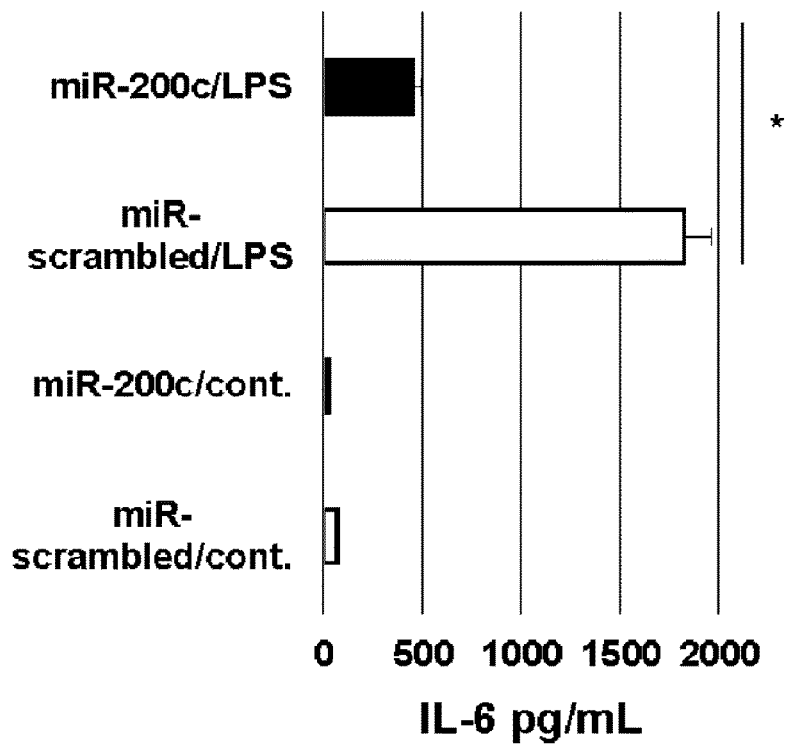
Figure 11C:
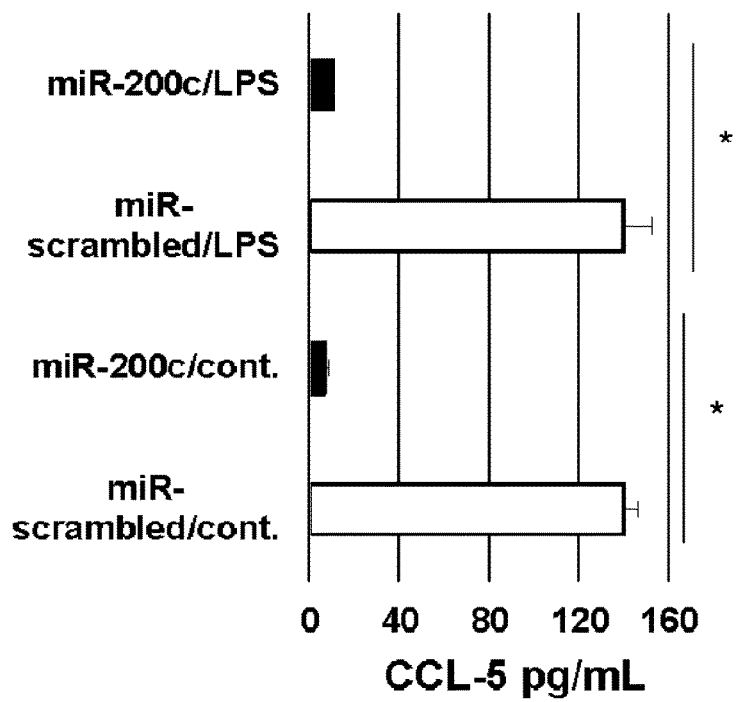
Figure 11D:
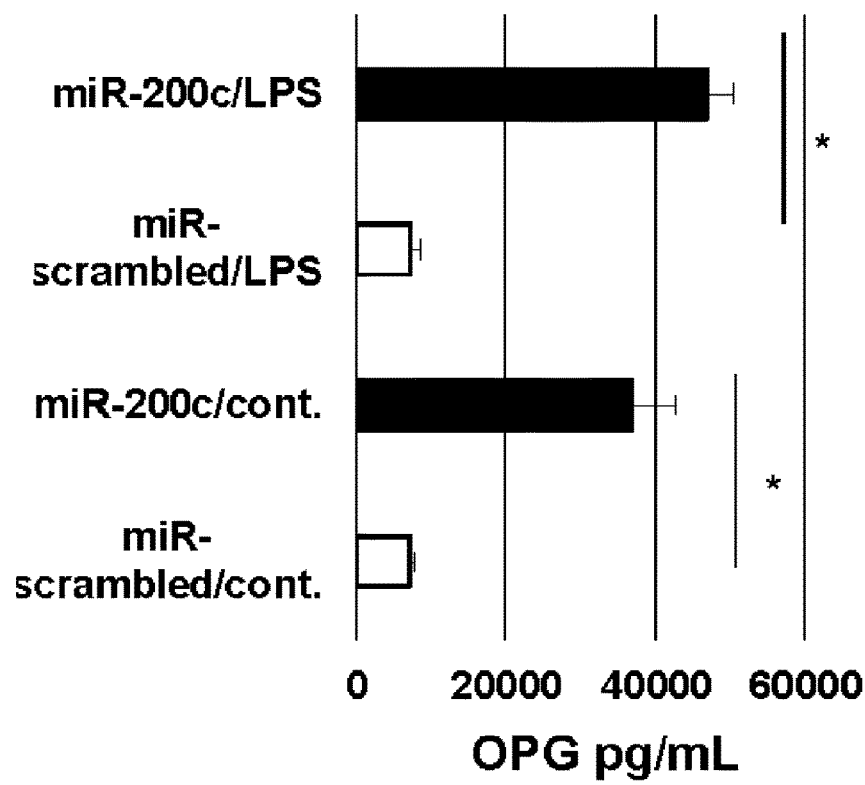
Figure 11E:
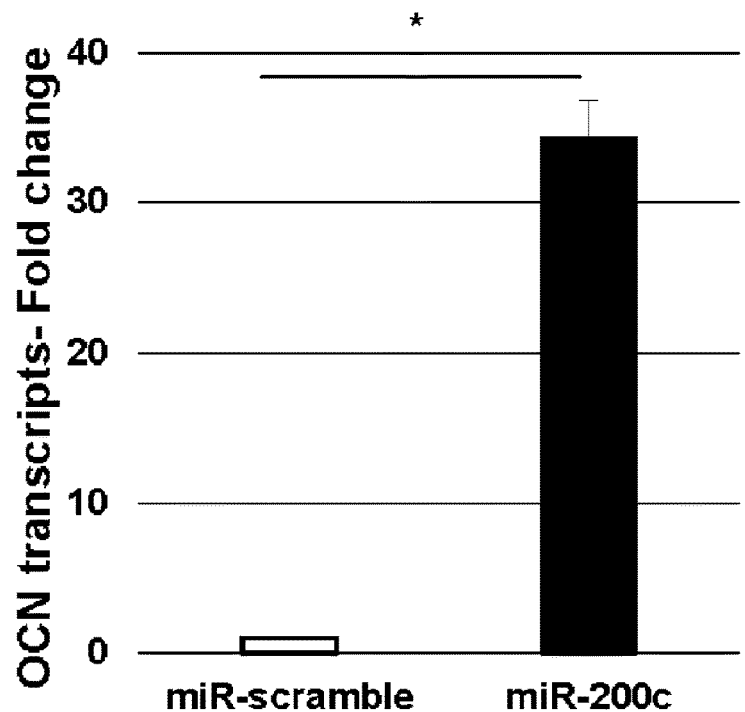
Figure 11F:
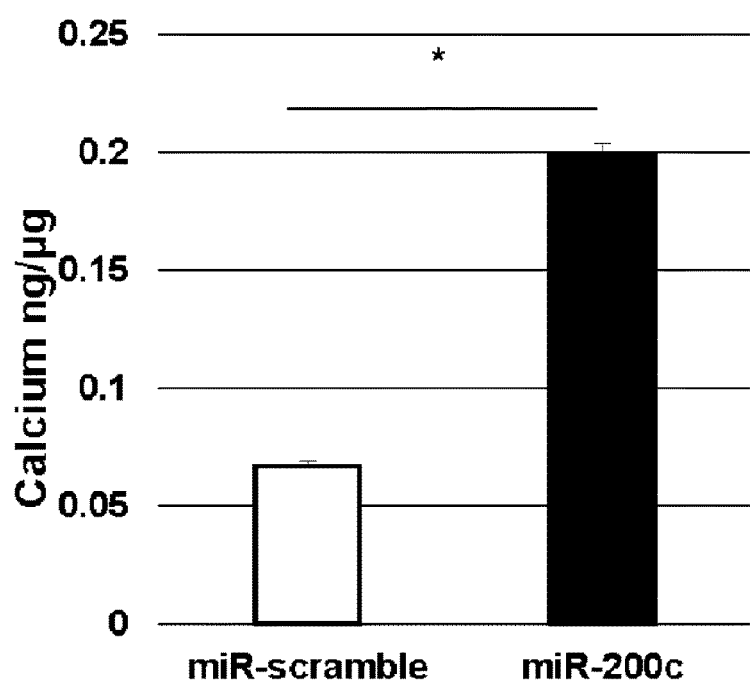

Human Preosteoblast Morphology and Proliferation are not Affected by miR-200c Expression Lentiviral vectors were used to infect miR-200c into HEPM cells. The cells positive for miR-200c marked by green fluorescent protein (GFP) expression, as shown in FIG. 10A, were used to analysis the effect of overexpression of miR-200c. The cells overexpressing miR-200c maintained a fibroblastic morphology. The level of miR-200c expression was measured using real-time PCR, and found to be approximately 16-fold (Δ/ΔCt) higher in HEPM cells infected with miR-200c than in control cells transfected with scrambled miRs (FIG. 10B). Limited miR-200c was detected in HEPM cells and the cells transfected with scrambled miRs. The doubling time for the miR-200c-infected HEPM cells did not differ significantly from that in either untreated cells or cells infected with scrambled miRs (FIG. 10C).

miR-200c Modulates Proinflammatory and Bone Metabolism Mediators and Increases Osteogenic Biomarkers in Human Preosteoblasts HEPM cells transduced with miR-200c or scrambled miRs were cultured with or without lipopolysaccharide (LPS) supplement (1 µg/ml) (Lonza N-185) up to 32 hours. The amounts of IL-8 in the culture medium with miR-200c overexpression are significantly lower than cells with scrambled miRs at each time point (FIG. 11A). Cells were cultured with FBS, which contains cytokines and growth factors, however we measured relative concentrations of IL-8, IL-6 and CCL-5 compared to controls cells also cultured in FBS. LPS supplement increased the amount of IL-8 in HEPM cells with scrambled miRs starting after 4 hours. However, the cells with miR-200c produced much less IL-8 than that of controls even after they were exposed to LPS (FIG. 11A). Similarly, the amount of IL-6 secreted by the cells with miR-200c overexpression in culture medium are lower (3-4 fold) than that of cells with scrambled miRs after 24 hours (FIG. 11B). With LPS treatment, IL-6 concentrations in the media are significantly increased, the IL-6 concentration of cells with miR-200c are significantly lower (2-3 fold) than that of cells with scrambled miRs (FIG. 11B). In addition, although LPS treatment didn't effectively increase CCL-5 production in HEPM cells, the cells with overexpression of miR-200c produced significantly lower CCL-5 (approximately 20-fold) than the cells with scrambled miRs (FIG. 11C). The amount of OPG secreted by the cells with miR-200c overexpression with or without LPS supplement are higher (6-8 folds) than that of cells with scrambled miRs after 32 hours (FIG. 11D). In addition, the HEPM cells with miR-200c or scrambled miRs were cultured in DMEM medium supplemented with glycerophosphate (1 mM) and ascorbic acid (5 mg/ml) up to 2 weeks. After one week, OCN transcripts measured using real-time PCR in miR-200c overexpression cells was 30-fold higher than control cells with scrambled miRs (FIG. 11E). The calcium content in miR-200c cells was 3 times higher than that of cells with scrambled miRs (FIG. 11F).

PEI Nanoparticles Effectively Deliver miR-200c to Primary Cell Cultures

Figure 12A:
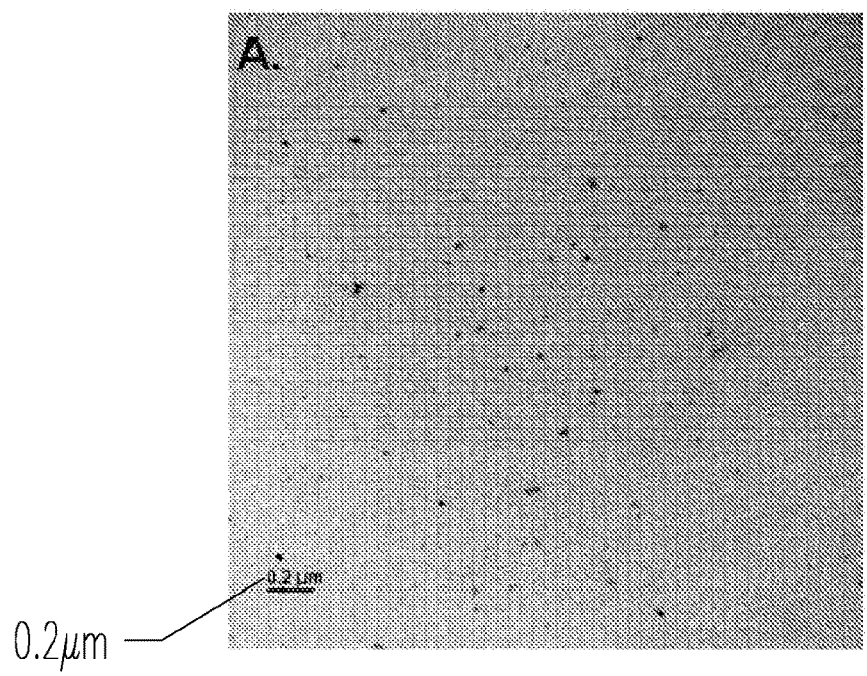
FIG. 12. Intracellular delivery of miR-200c using PEI nanoparticles to human primary periodontal ligament fibroblasts and bone marrow MSCs. A) TEM image of PEI-miR-200c nanocomplexes. B) and C) Fold change of the transcript of miR-200c in human periodontal ligament fibroblasts (B) and bone marrow MSCs (C) transfected with empty vector (EV) (10 μg/per well) and miR-200c (1, 5, 10 μg/per well).
Figure 12B:
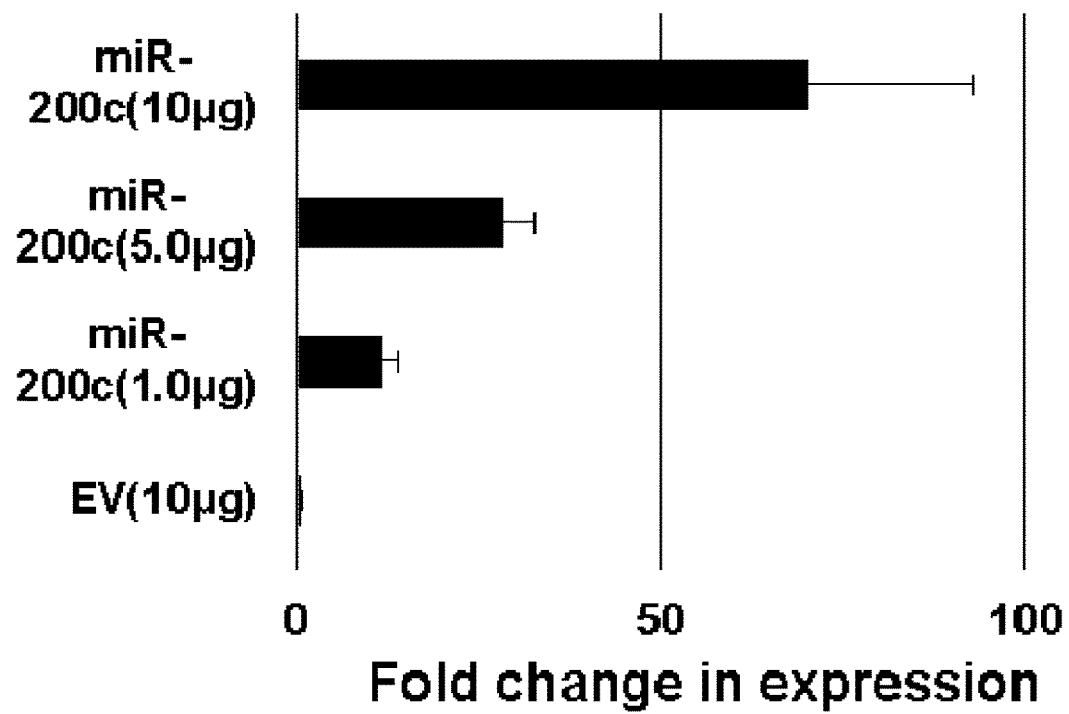
Figure 12C:
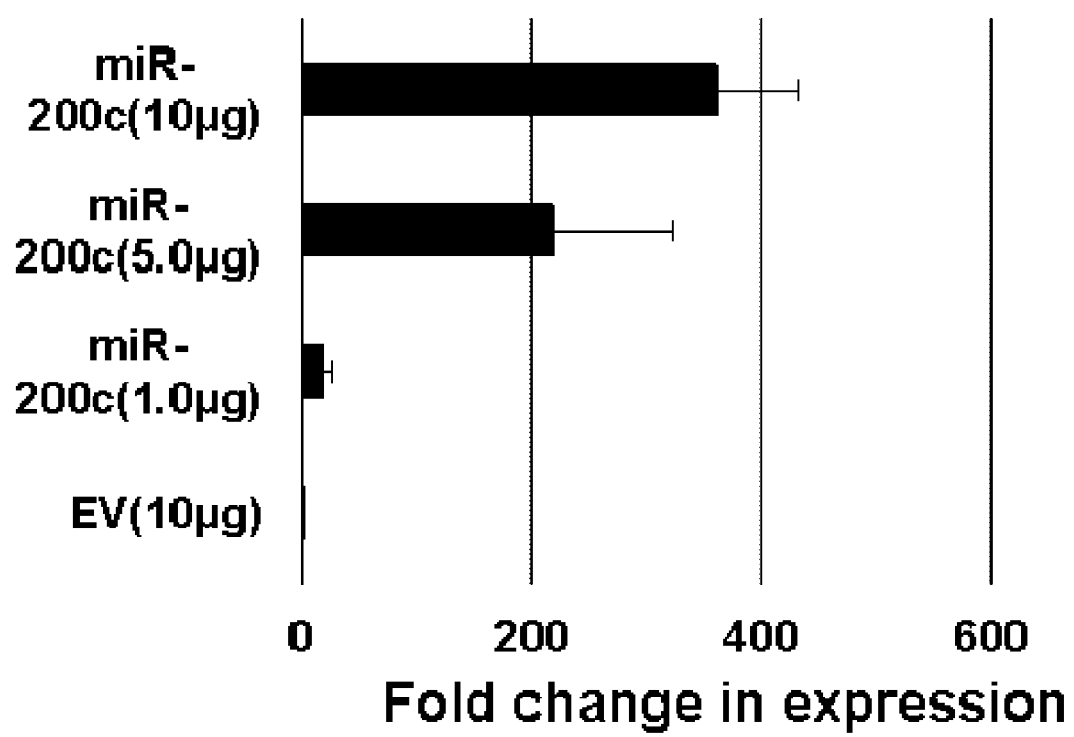
Figures 13A, 13B:
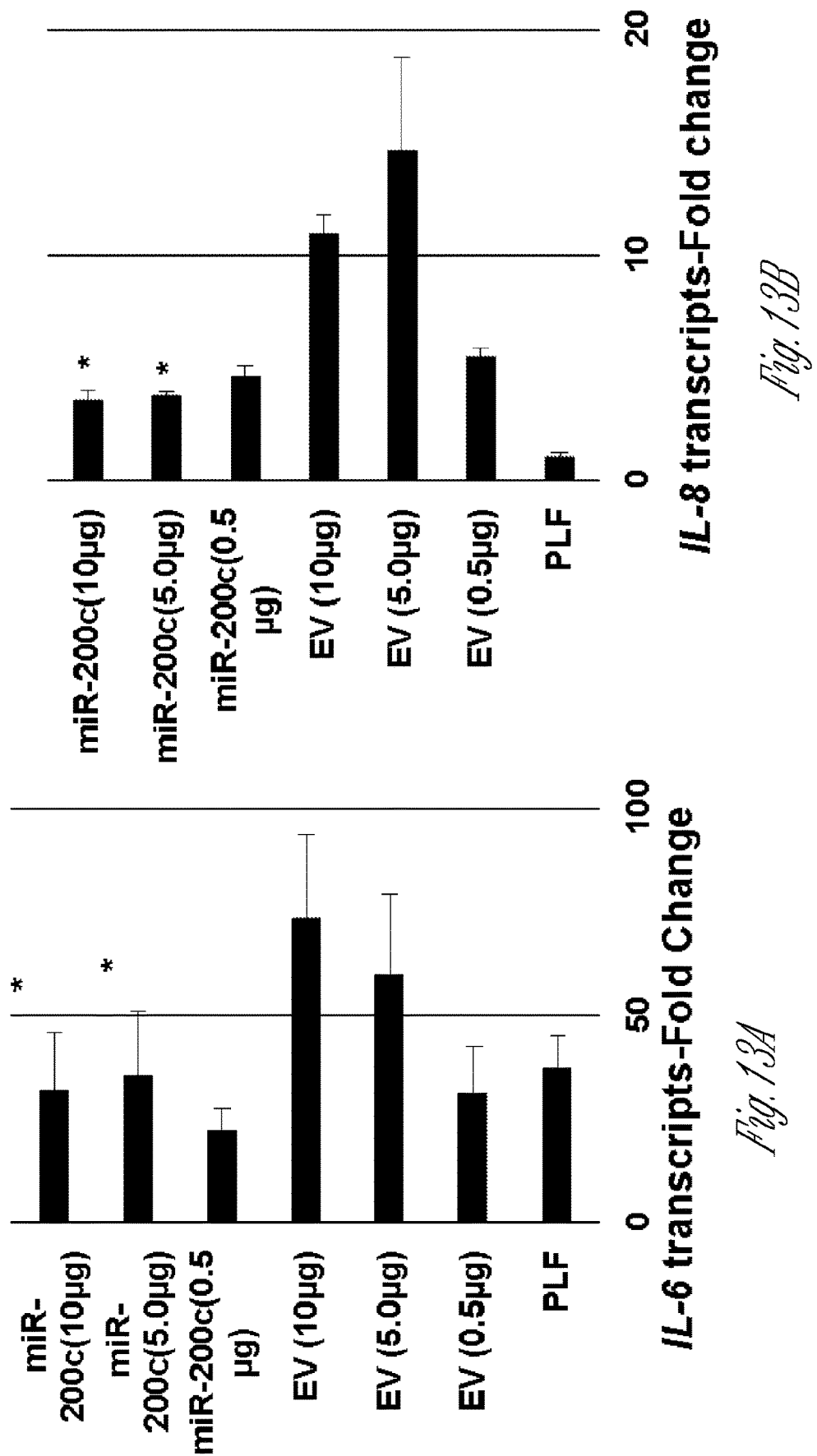
FIG. 13. miR-200c delivered using PEI nanoparticles inhibits IL-6, IL-8, and CCL-5 in primary human periodontal ligament fibroblasts. A)-C) the transcripts of IL-6 (A), IL-8 (B), and CCL-5 (C) in the cells with miR-200c or empty vector cultured in DMEM supplemented with LPS after 24 hours; D) and E) the amounts of IL-6 (D), IL-8 (E), and CCL-5 (F) secreted by the cells with miR-200c or empty vector cultured in DMEM supplemented with LPS after 12 and 32 hours, respectively. *: p<0.05 vs empty vector with the same amount.
Figure 13D:
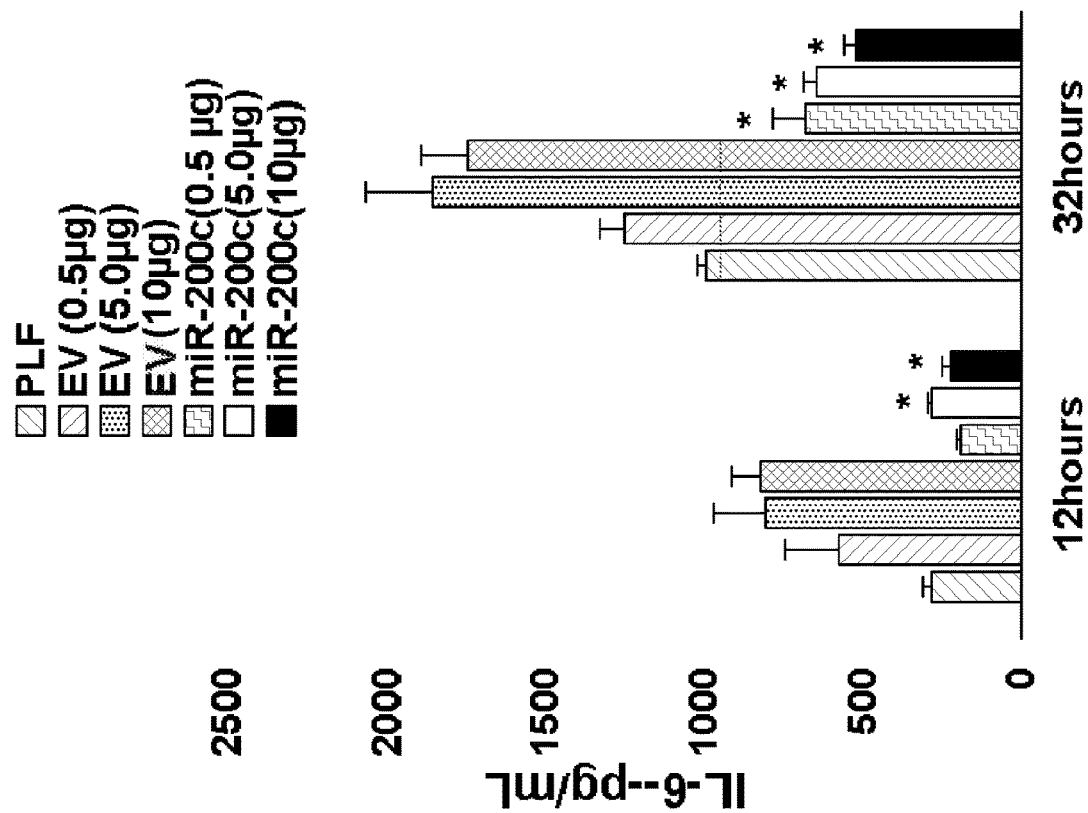
Figure 13C:
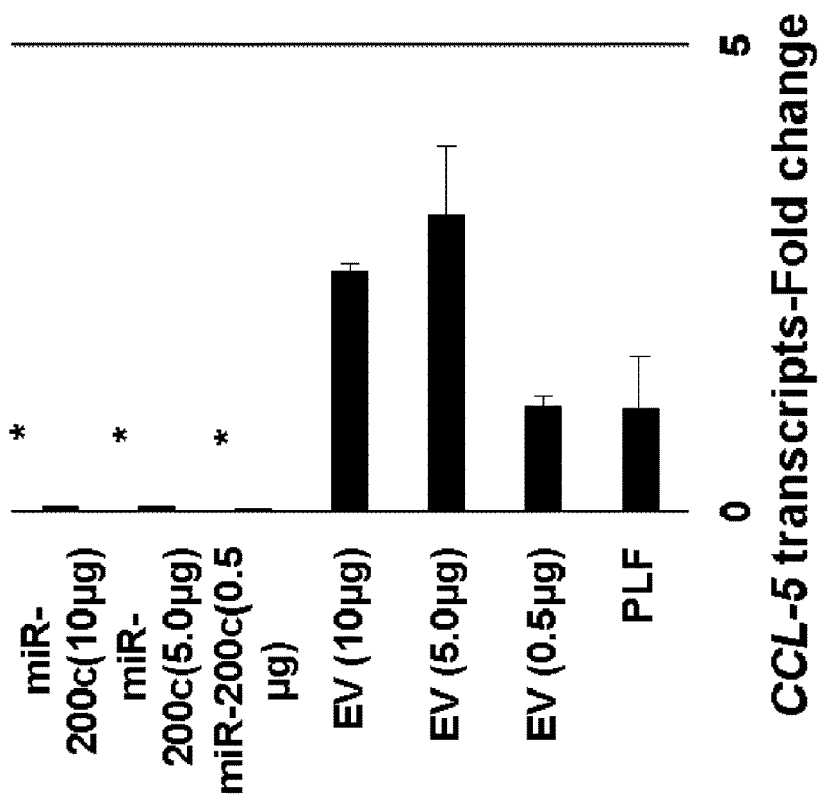
Figures 13E, 13F:
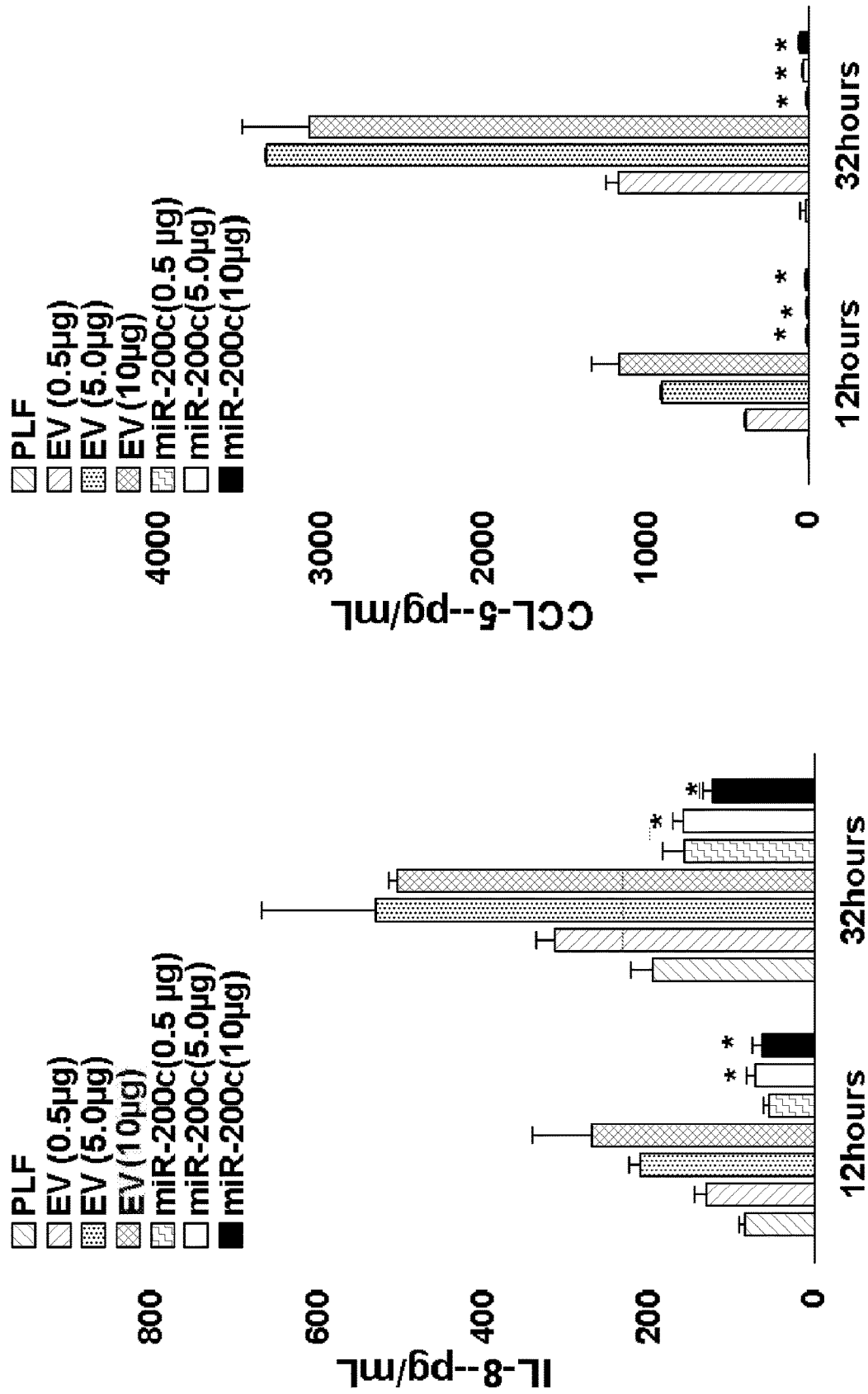

Plasmid miR-200c was incorporated into PEI to form nanoplexes at an N/P ratio of 10:1 {ratio of the total number of end amine groups (N) of PEI and the total number of DNA phosphate groups (P)}. PEI-miR-200c nanoplexes were visualized using TEM (FIG. 12A). PEI-miR-200c nanoplexes at 1, 2, 5, and 10 µg/per well were added to the medium of cultured primary human bone marrow MSCs and periodontal ligament fibroblasts in 6-well plates. PEI-empty vector (10 µg/per well) was used as a control. The medium was changed after 4 hours to remove excess nanoplexes and the cells were continuously cultured in DMEM medium. After 2 days miR-200c expression was detected using real-time PCR in periodontal ligament fibroblasts (FIG. 12B). miR-200c dose-dependent expression was also observed in human bone marrow MSCs (FIG. 12C).

miR-200c Delivered Using PEI Nanoparticles Inhibits IL-6, IL-8 and CCL-5 in Primary Human Periodontal Ligament Fibroblasts Primary human periodontal ligament fibroblasts were treated with PEI-miR-200c at different concentrations, the cells were cultured using DMEM with LPS supplement (1 µg/mL) for up to 32 hours. The transcripts levels of IL-8, IL-6, and CCL-5 in human periodontal ligament cells with PEI-miR-200c nanoplex treatment are lower than that of controls with treatment using empty vectors after 24 hours (FIGS. 13A, B, C). Although the transcripts of IL-6, IL-8 and CCL-5 are varied by the dose in the cells treated with empty vectors, all treatment using PEI-miR-200c nanoplexes at different doses show the efficacy on reducing these proinflammatory mediators. Furthermore, the concentration of IL-6, IL-8, and CCL-5 in the supernatant of cells with different treatments after 12 and 32 hours were also decreased after miR-200c nanoplex treatments (FIGS. 13D, E, F). Similar to the transcript quantitation, the cell receiving PEI-empty vector at 5 and 10 μg produce higher concentrations of IL-6, IL-8, and CCL-5 compared to control cells without transfection and the increase is statistically significant after 32 hours. However, the protein levels of these mediators in cells treated with PEI-miR-200c are significantly lower than that of cells treated with same concentration of empty vectors. Also, the miR-200c cells have lower levels of IL-6 and IL-8 than control cells without transfection after 32 hours.

miR-200c Directly Targets the 3'UTR of IL-6, IL-8, and CCL-5

Figure 14B:
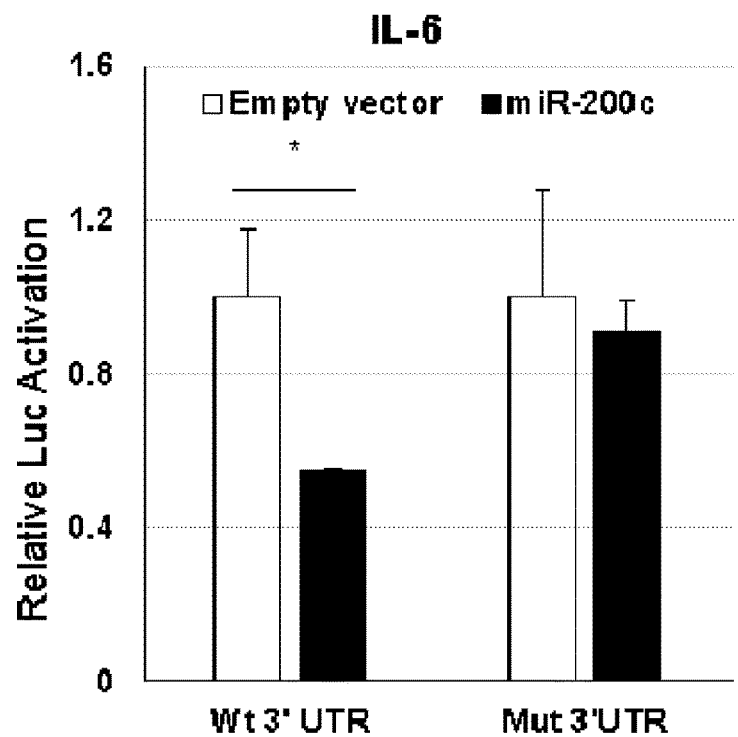
FIG. 14. miR-200c directly targets the 3'UTR of IL-6, IL-8, and CCL-5. A) The sequence and miR-200c binding region located in the 3'UTR and mutated 3'UTR of IL-6, IL-8, and CCL-5. (SEQ ID Nos:7-15) B)-D) Normalized luciferase activities of the 3' UTR IL-6, IL-8, and CCL-5-luciferase reporters and their 3'UTR-mutated-luciferase reporters treated with empty vector or miR-200c. *: p<0.05
Figure 14C:
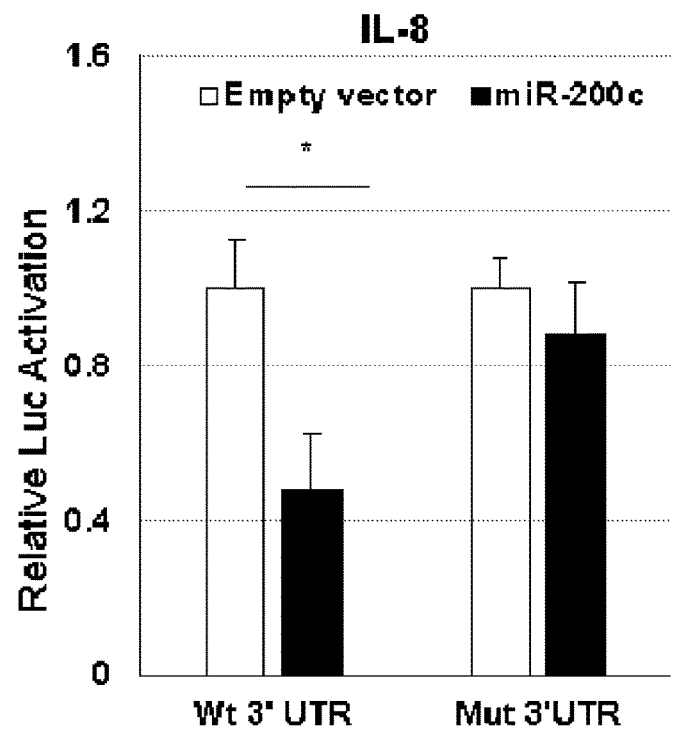
Figure 14D:
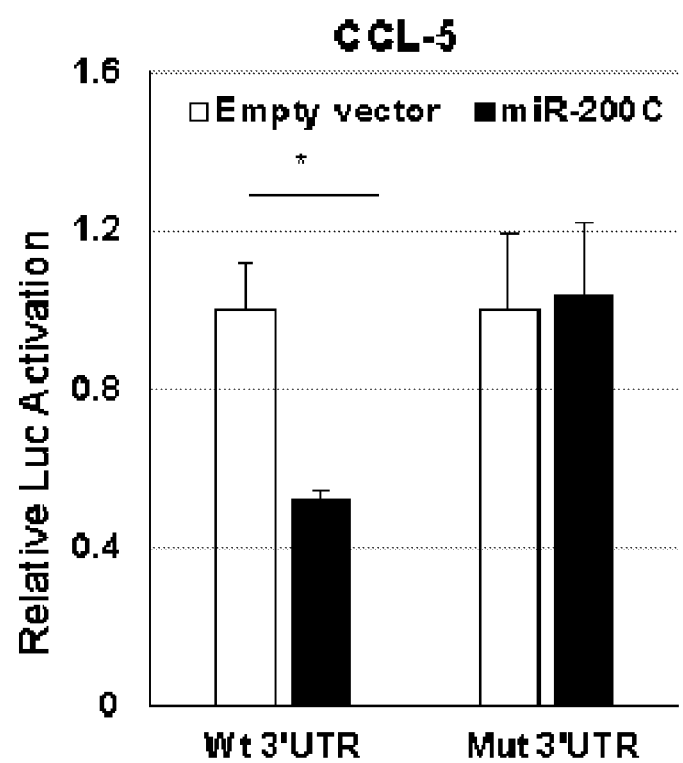

To test if miR-200c directly targets these mediators the 3'UTR sequence was cloned after the luciferase gene and luciferase activity was determine with and without miR-200c present. The sequence and miR-200c binding region located in the 3'UTR of each mediator is shown in FIG. 14A. miR-200c repressed luciferase activity from the IL-6, IL-8 and CCL-5 reporter constructs co-transfected in cells (FIGS. 14B, C, D). Normalized luciferase activity of the luciferase reporter with 3' UTR of IL-6, IL-8, and CCL-5 shows significantly lower with expression of miR-200c compared to with empty plasmid vector. However, there is no loss of luciferase activity when miR-200c binding sequence is mutated in the 3'UTR of IL-6, IL-8 and CCL-6 (FIG. 14). A miR-200c Inhibitor Reduces Binding Activity of miR-200c to 3' UTR of IL-6, IL-8, and CCL-5 and Eliminates its Inhibitory Effects.

Figure 15A:
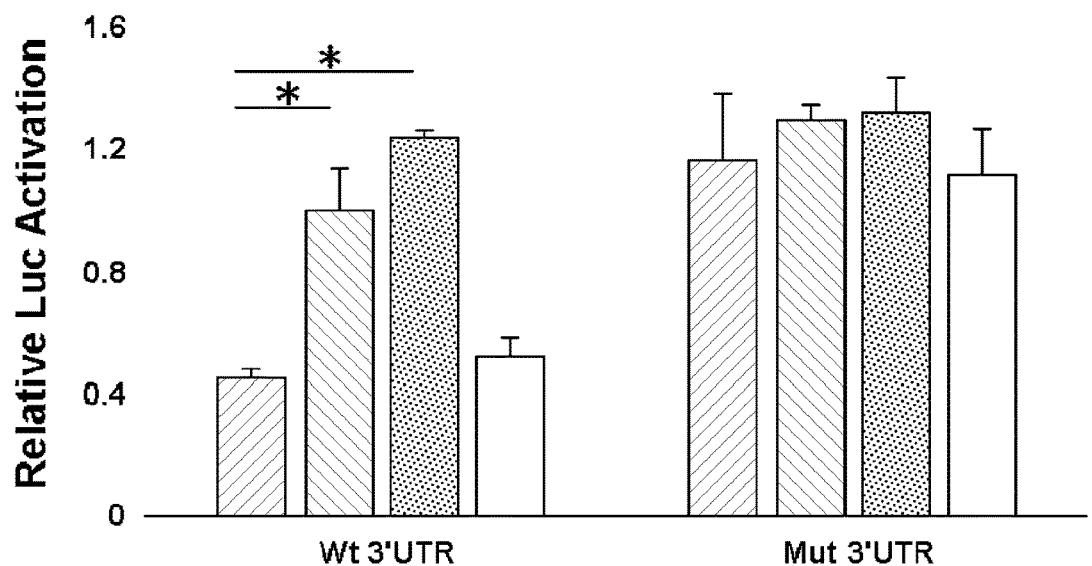
FIG. 15. PMIS-200c reduces binding activity of miR-200c to the 3'UTR of IL-6, IL-8, and CCL-5 and the function of miR-200c. A)-C) Normalized luciferase activities of the 3'UTR IL-6, IL-8, and CCL-5-luciferase reporters and their 3'UTR-mutated-luciferase reporters co-treated with miR-200c and PMIS-EV or PMIS-200c at different ratios of concentration. D)-F) the transcripts of IL-6 (D), IL-8 (E), and CCL-5 (F) in the cells co-treated with miR-200c and PMIS-EV or PMIS-200c cultured in DMEM supplemented with LPS after 24 hours; *: p<0.05
Figure 15B:
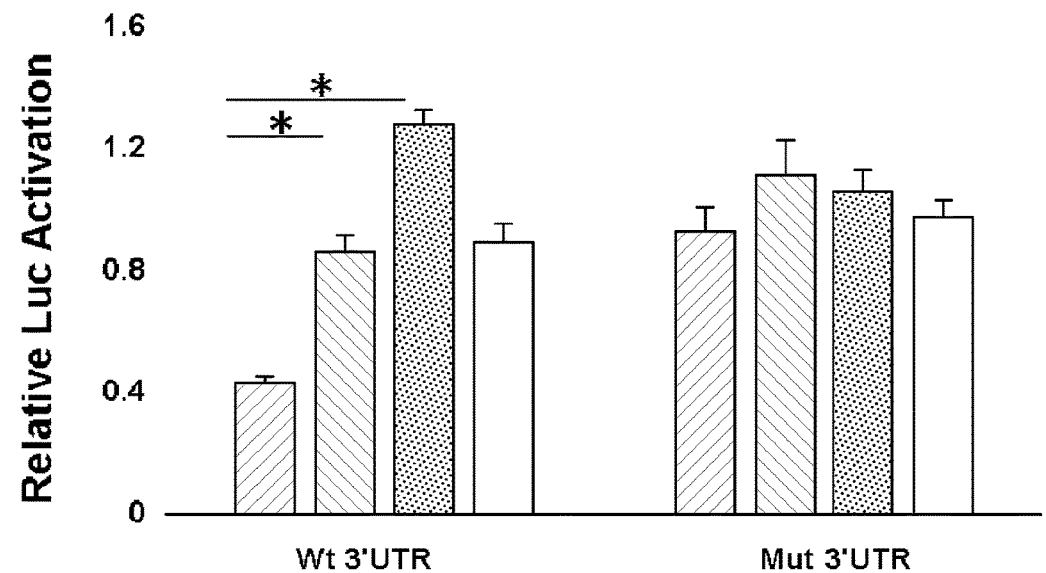
Figure 15C:
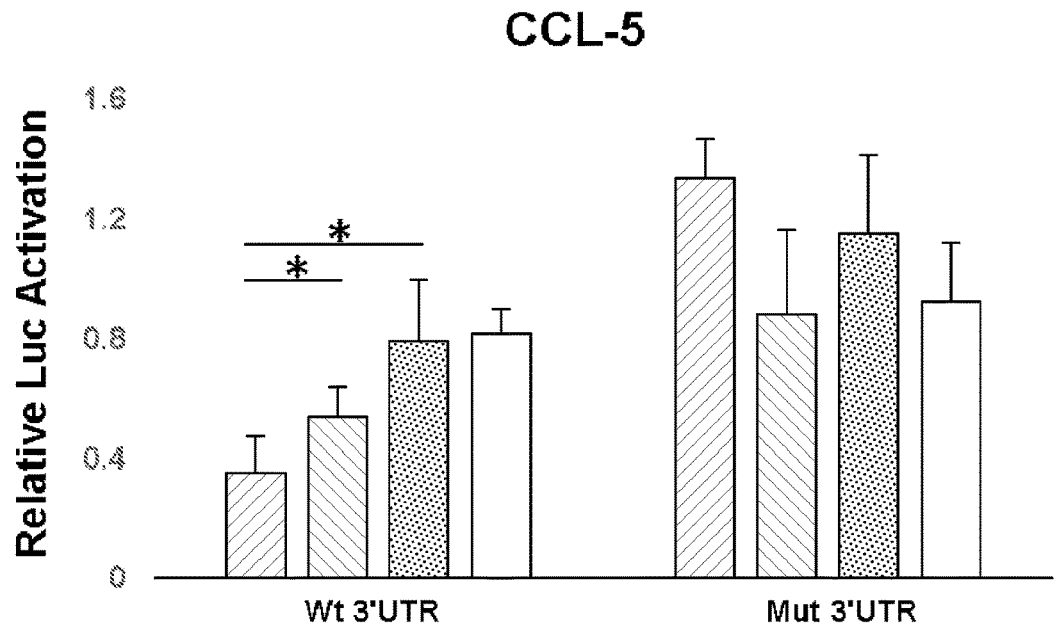
Figure 15D:
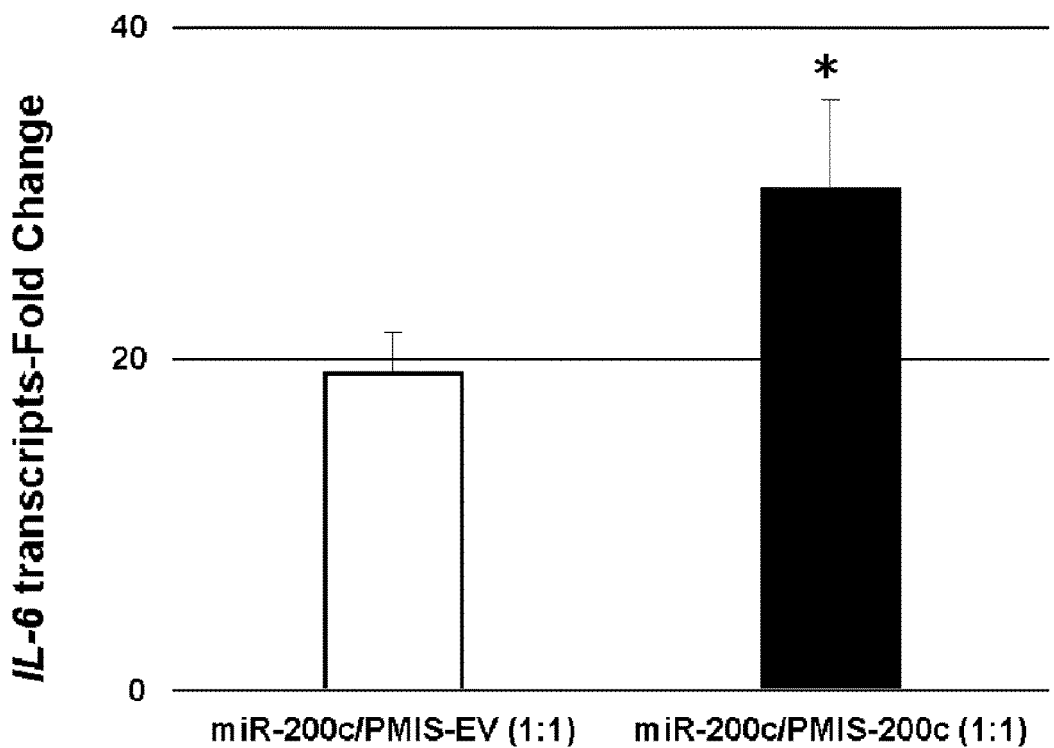
Figure 15E:
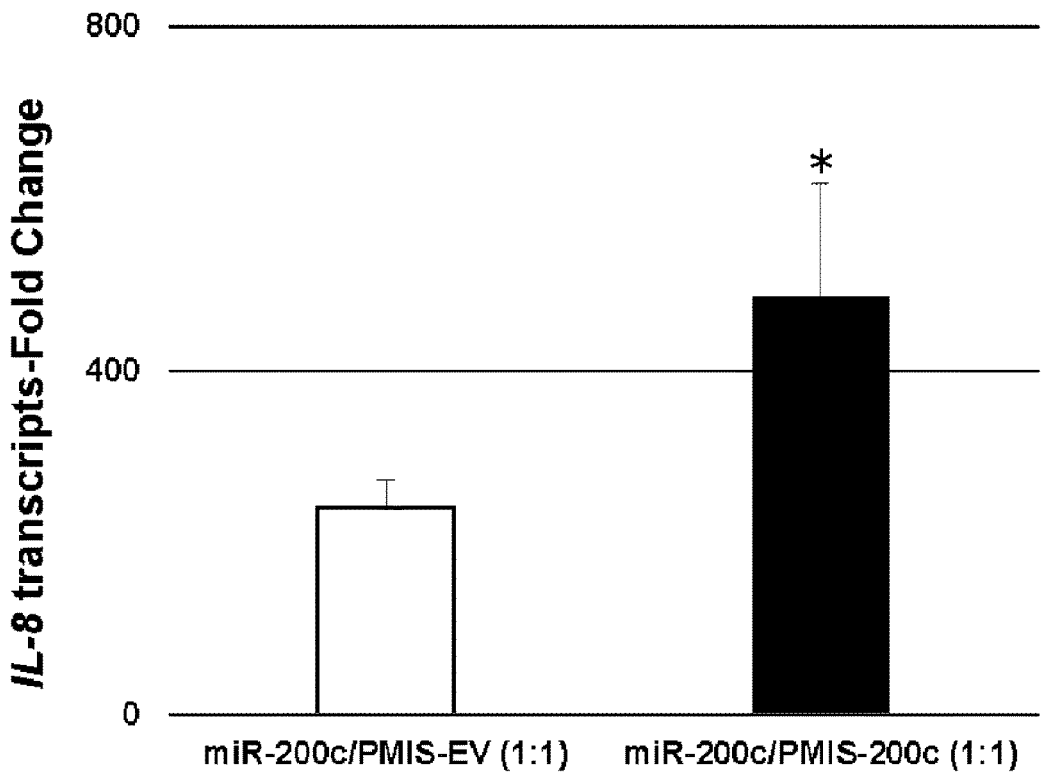
Figure 15F:
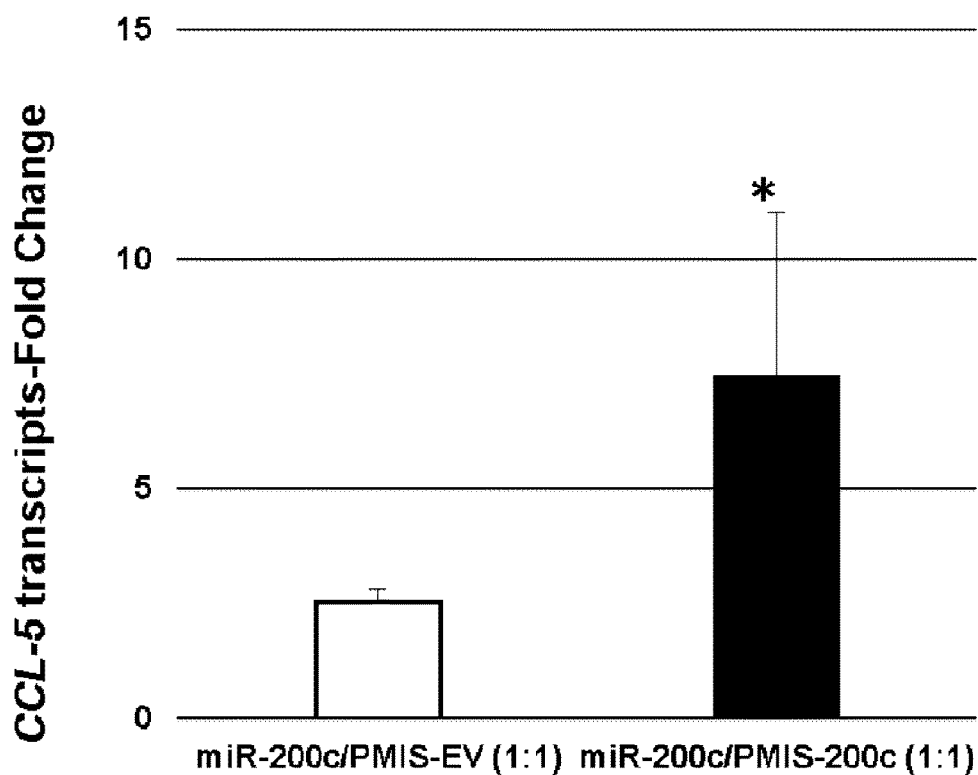
Figure 16A:
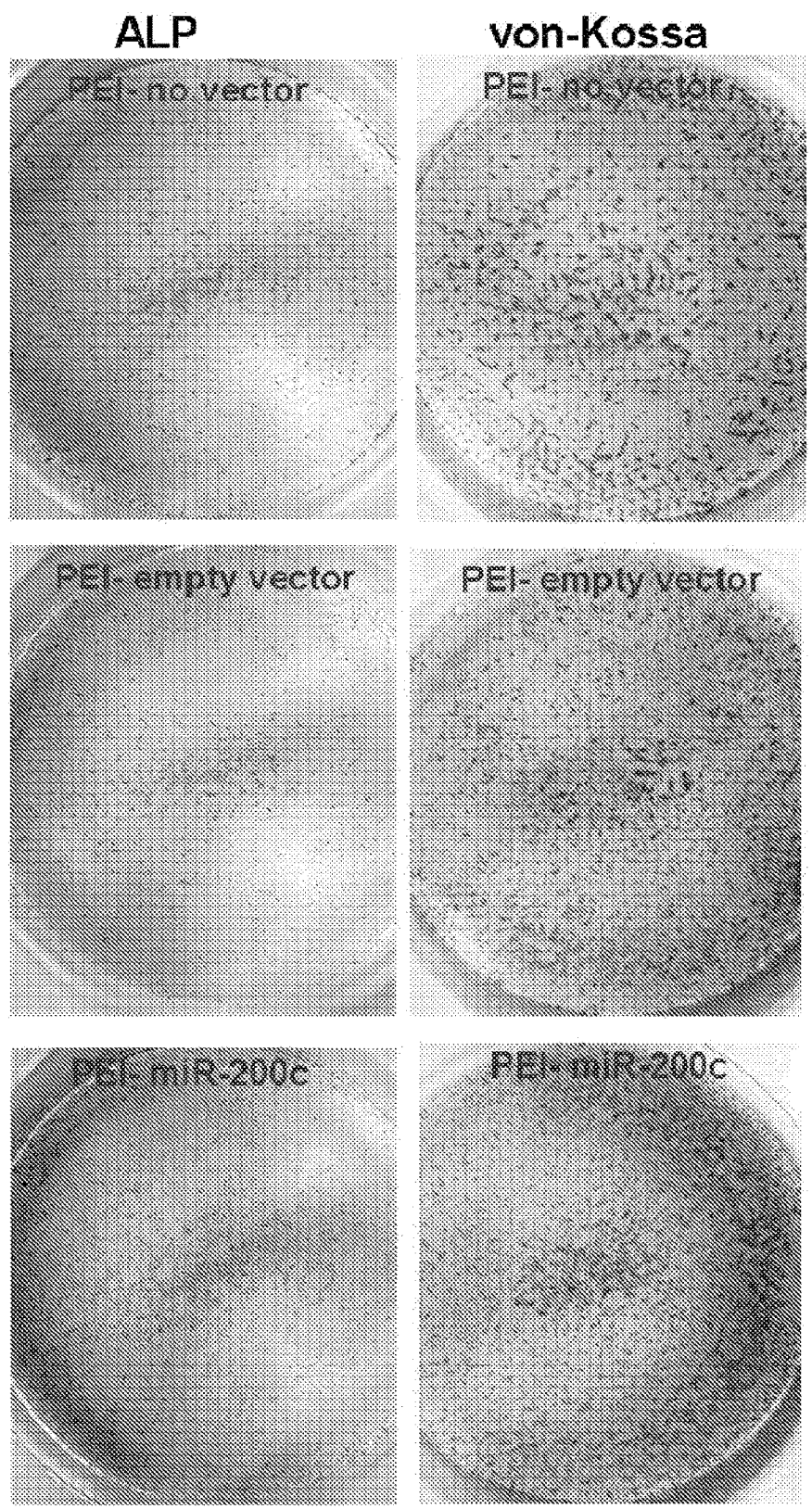
FIG. 16. Enhancement of osteogenic differentiation of human bone marrow MSCs with overexpression of miR-200c using PEI nanoparticles. A) Images of ALP and von-Kossa staining in MSCs overexpressing miR-200c, one and two weeks after treatment with osteogenic medium. B and C) the transcript of ALP (B) and Runx2 (C) in MSCs overexpressing miR-200c, one week after treatment with osteogenic medium. D) and E) Quantitative measurement of ALP levels (D) and calcium content (E) in MSCs overexpressing miR-200c, one and two week after treatment with osteogenic medium. Each measurement was made in triplicate. *: p<0.05.
Figure 16C:
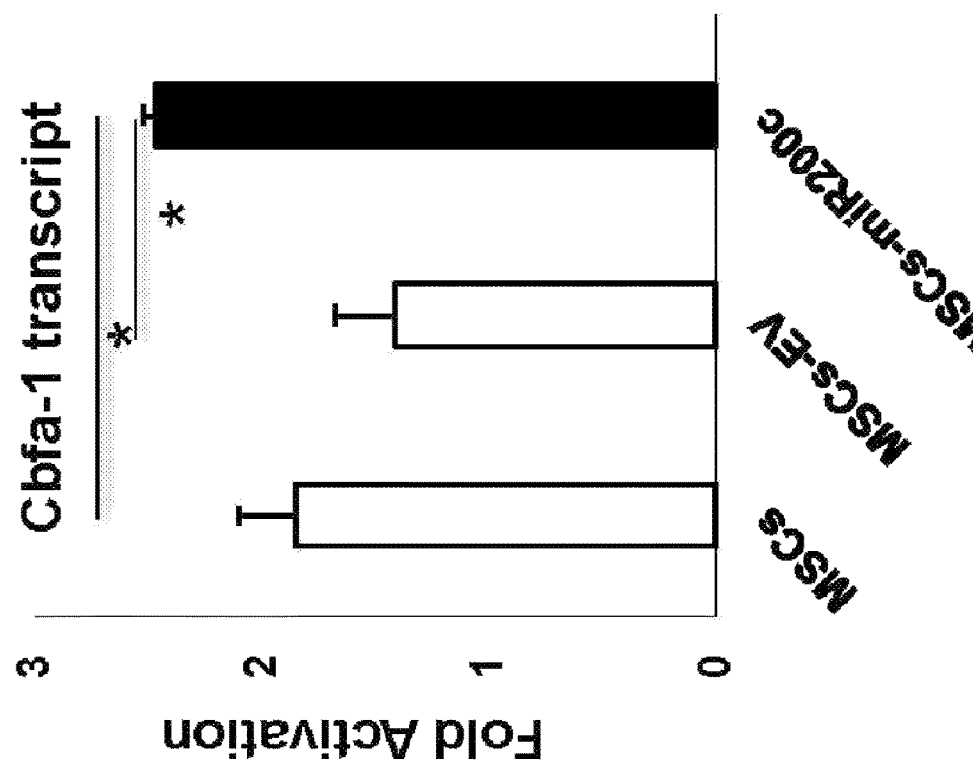
Figure 16B:
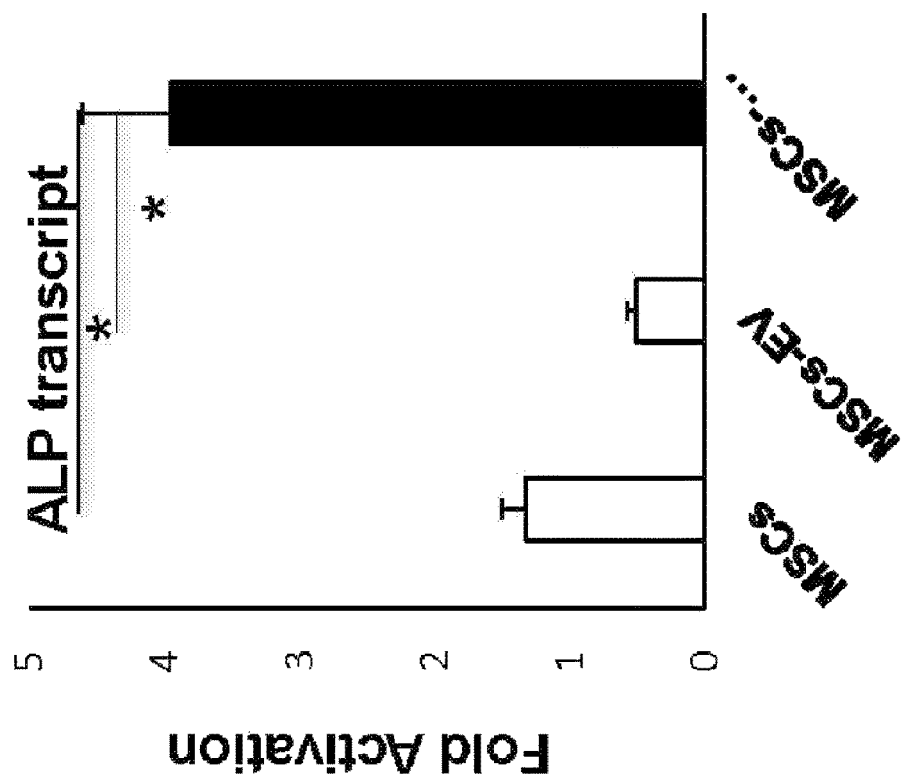
Figure 16E:
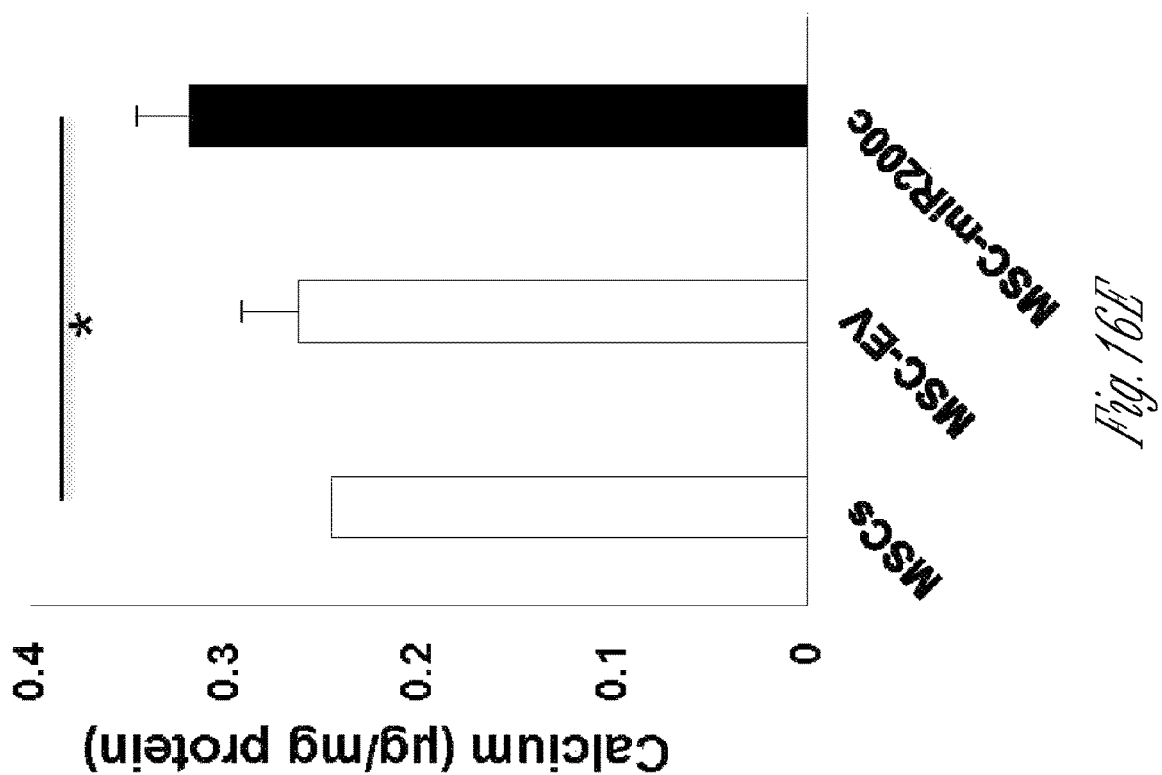
Figure 16D:
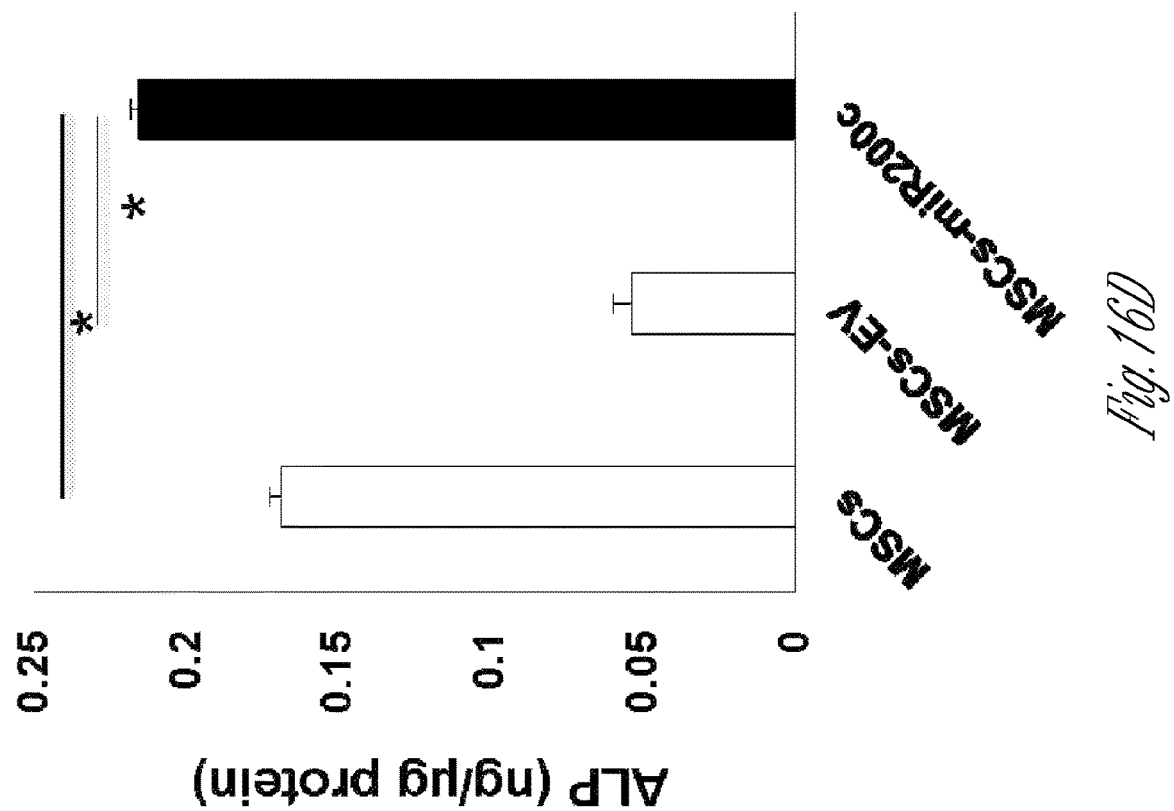

To further confirm if miR-200c directly targets 3' UTR of these mediators, the luciferase activity inhibited by miR-200c was determined after treatment with a plasmid-base miR inhibitor system (PMIS) designed to bind miR-200c (PMIS-200c). PMIS-200c significantly increased luciferase activity from the luciferase reporter containing the 3' UTR of IL-6, IL-8, and CCL-5 treated with miR-200c, compared to PMIS designed to bind empty vector (PMIS-EV) or miR-17/18 (PMIS-17/18). However, there is less change of luciferase activity when the mutated sequence in the 3'UTR of IL-6, IL-8 and CCL-6 was used (FIGS. 15A, B, C). In addition, PMIS-200c also significantly increases the transcripts of IL-6, IL-8 and CCL-5 in human periodontal ligament fibroblasts with overexpression of miR-200c after LPS stimulation compared to PMIS-EV. These results further indicate the inhibitory effects of IL-6, IL-8 and CCL-5 mediated by miR-200c by targeting their 3' UTRs.

miR-200c Delivered Using PEI Effectively Improves Osteogenic Differentiation of Human Bone Marrow MSCs Human bone marrow MSCs were transfected using PEI-miR-200c or PEI-empty vector at 1.0 μg/per well, the cells were subsequently cultured using DMEM supplemented with ascorbic acid and β-glycerophosphate up to 2 weeks. ALP staining of MSCs shows mineralization effects with different treatment in culture dishes, 1 week after culture in osteogenic medium (FIG. 16A). Staining was observed in both controls, including MSCs with and without treatment with the PEI-empty vector (FIG. 16A). PEI-miR-200c transfected cells show stronger ALP staining than that in controls (FIG. 16A). Positive staining of von-Kossa was observed in MSCs with and without treatment with the PEI-empty vector (FIG. 16A). The von-kossa staining was darker in the MSCs transfected with miR-200c (FIG. 16A). Quantitatively, the transcripts of ALP (FIG. 16B) and Runx2 (FIG. 16C) are significantly increased in the cells treated with PEI-miR-200c, compared to controls including MSCs treated with PEI, with or without empty vector. In addition, the ALP concentration (FIG. 16D) and calcium content (FIG. 16E) in the MSCs transfected with miR-200c was increased after 2 weeks in culture.

Discussion

In this study it was observed, for the first time, that overexpression of miR-200c effectively represses multiple proinflammatory mediators, including IL-6, IL-8 and CCL-5, in human preosteoblasts. The gene analysis indicated that miR-200c may directly targeting 3'UTR of these mediators. Overexpression of miR-200c may also promote OPG and improve osteogenic differentiation in these cells. In addition, these studies demonstrated that plasmid DNA containing miR-200c can be effectively delivered using a non-viral delivery system. miR-200c delivered using PEI nanoparticles was found to effectively inhibit IL-6, IL-8, and CCL-5 in human primary periodontal ligament fibroblasts and improve osteogenic differentiation in human bone marrow MSCs. These data strongly suggest that miR-200c may potentially be used to repress periodontitis-associated bone resorption and restore the periodontal bone defects by modulating imbalance and dysregulation of proinflammatory mediators and improving bone formation.

miR-200c Directly Targets the Proinflammatory Molecules IL-8, IL-6 and CCL-5

While miR-200c is underexpressed in gingival tissues of periodontitis patient, its function and underlying mechanism(s) in this chronic inflammatory disease is less understood. miR-200c suppression by IL-6 may direct constitutive activation of inflammatory signaling circuit in transformation and tumorigenesis (Rokavec et al., 2012). This was the first study indicating that miR-200c may potentially involve in inflammation suppression. Furthermore, miR-200c may reduce NF-kB activation by modifying TLR-4 signaling through the MyD88-dependent pathway (Wendlandt et al., 2012), and it may reduce IL-8 expression by targeting IKBKB in NF-kB signal pathway (Chuang et al., 2014). Another report indicated that miR-200c may target a NF-κB up-regulated TrkB/NTF3 autocrine signaling loop in breast tumors (Howe et al., 2012). However, there is no previous studies that investigated the anti-inflammatory activity of miR-200c in periodontitis and related bone resorption and bone formation.

miR-200c can effectively inhibit IL-8 expression in human preosteoblasts and periodontal ligament fibroblast under the stimulation of a bacterial endotoxin by binding to the IL-8 3' UTR. Moreover, it was also shown that miR-200c can effectively reduce IL-6 and CCL-5 expression in human preosteoblasts and periodontal ligament fibroblasts after they are treated with bacterial endotoxin. The reporter gene analysis also demonstrated that miR-200c effectively targets 3' UTRs of IL-6 and CCL-5. As IL-6, IL-8 and CCL-5 major proinflammatory mediators having critical roles in inflammation, these results strongly suggest that miR-200c possesses a powerful capability to reduce inflammation via post-transcriptional regulation of these proinflammatory mediators.

miR-200c Regulates Osteogenic Differentiation miR-200c enhanced OCN and calcium content in human preosteoblasts and miR-200c delivered using PEI nanoparticles promotes increased ALP, Runx2 and calcium content in human MSCs. While miR-200c was reported to participate in stem cell proliferation and differentiation, this is the first study that demonstrates the potential function of miR-200c to improve osteogenic differentiation and bone regeneration (Huang et al., 2014). Proinflammatory mediators have been demonstrated to impair bone formation by reducing differentiation of osteoblasts and their progenitor cells (Howe at al., 2012; Cao et al., 2013), which may potentially explain the function of miR-200c on enhancing bone formation. In addition, it was previously reported that miR-200c targets Noggin 3'UTR and down-regulates Noggin expression in dental epithelial cells. Noggin, an antagonist of BMP signals, is a secreted protein that binds and inactivates a number of BMPs, including BMP-2, 7. Noggin suppression has been demonstrated to promote BMP-induced bone regeneration in vitro and in vivo (Lian et al., 2012; Stoecklin-Wasmer at al., 2012). Therefore, the enhanced osteogenic differentiation mediated by overexpression of miR-200c may be accomplished by inhibiting both proinflammatory cytokines and Noggin since miR-200c inhibition of Noggin expression was observed in human bone marrow MSCs (data not shown). However, the exact underlying mechanism(s) of miR-200c regulation on osteogenic differentiation requires further studies.

Nanoparticle Delivery of miR-200c

Although non-viral gene delivery systems have shown promise as alternative approaches of recombinant viral vectors, nanoparticles are the only non-viral vectors that can provide a targeted intracellular delivery with controlled release properties. Nanoparticles can serve as a local drug delivery system to oral mucosa (Holpuch et al., 2010). PEI nanoparticles have been used as a non-viral vector for gene delivery due to their "proton-sponge" effect and high transfection efficiency (Hikiji et al., 2000). PEI was shown to be effective in transfecting cells even in the presence of serum (Wang et al., 2012). Previous studies have successfully delivered plasmid DNA using PEI nanoparticles (Chang et al., 2009). It was demonstrated that N/P ratios significantly influence the size, surface charge, transfection efficiency, and cytotoxicity of PEI nanoplexes. Previous studies have also shown that PEI-pDNA {encoding for platelet derived growth factor-B (PDGF-B)} nanoplexes can induce significantly higher bone regeneration in calvarial rat defects (Elangovan et al., 2014). In this study it was shown that PEI can effectively deliver miR-200c into primary human periodontal ligament fibroblasts and bone marrow MSCs, demonstrating the feasibility of transfecting miR-200c using PEI nanoparticles. These results along with previous in vivo studies strongly suggest that PEI nanoparticles may potentially be used as a delivery system to transfect miR-200c for clinical application purposes. In addition, it was observed that the up-regulated content of miR-200c expression is dose-dependent according to PEI-miR-200c nanoplex treatment.

The cellular inflammation response and inhibitory effects can be mediated by miR-200c in response to the stimulation by bacterial endotoxin. Interestingly, the secreted amounts of IL-6, IL-8, and CCL-5 increased with the dose of transfection of plasmid DNA. This is probably caused by the innate immune system of the cells that can recognize nucleic acids after transfection. It has been demonstrated that after plasmid DNA is detected by endosomal toll-like receptors, including TLR3, TLR7, and TLR8, and cytoplasmic RIG-I and MDA5, endosomal TLR-9 and cytoplasmic DAI may bind the DNA, resulting in the activation of NF-kB and interferon regulatory factor transcription factors (Mogensen, 2009). Therefore, in order to develop a plasmid miR-200c based approach for anti-inflammation an optimal transfection of miR-200c to limit plasmid NDA-induced innate immune response is necessary. Besides periodontitis, IL-6, IL-8, and CCL-5 as major proinflammatory mediators they also play critical roles in many inflammation-related diseases, including osteoarthritis and Parkinson's disease. Thus, the inhibitory effects mediated by miR-200c indicate that this miR may be potentially developed into a therapeutic tool for these diseases.

Summary

In this study, the molecular effects of overexpressed miR-200c was investigated using lentiviral vectors on modulating periodontitis-associated proinflammatory and bone metabolism factors and the biomarkers of osteogenic differentiation in human embryonic palatal mesenchyme (HEPM) cells, a cell line of preosteoblasts. It was demonstrated that overexpression of miR-200c in human preosteoblast cell line effectively suppresses multiple proinflammatory mediators, including IL-6, IL-8, and CCL-5, and increase OPG (an osteoclastogenesis inhibitor) and osteocalcin (OCN) and calcium content. In addition, polyethylenimine (PEI), a non-viral nanoparticle delivery system, was used to intracellularly deliver plasmid DNA containing miR-200c into primary human periodontal ligament fibroblasts and bone marrow MSCs. It was observed that miR-200c delivered using PEI can effectively inhibit IL-6, IL-8, CCL-5 in periodontal ligament fibroblasts and enhances osteogenic differentiation of human bone marrow MSCs in vitro. miR-200c directly targets the 3'UTR of IL-6, IL-8 and CCL-5. These data indicate the usefulness of miR-200c in prevention and restoration for periodontitis-induced bone loss, with the ability to modulate inflammation and bone formation.

Exemplary Embodiments

1. A method to prevent, inhibit or treat aveolar or periodontal bone loss, comprising: administering to a mammal an effective amount of a composition comprising isolated miRNA of one or more members of miR-200 family.
2. A method to enhance bone regeneration, comprising: administering to a mammal an effective amount of a composition comprising isolated miRNA of one or more members of miR-200 family.
3. A method to prevent, inhibit or treat peri-implantitis or periodontitis, comprising administering to a mammal an effective amount of a composition comprising isolated miRNA of one or more members of miR-200 family.
4. A method to prevent, inhibit or treat osteoarthritis, comprising administering to a mammal an effective amount of a composition comprising isolated miRNA of one or more members of miR-200 family.
5. The method of any one of embodiments 1 to 4 wherein the mammal is a human, bovine, ovine, caprine, equine, porcine, canine or feline.
6. The method of any one of embodiments 1 to 5 wherein the amount is effective to enhance osseointegration of a dental implant.
7. The method of embodiment 1, 2 or 3 wherein the amount is effective to enhance alveolar bone regeneration.
8. The method of any one of embodiments 1 to 7 wherein the mammal is a diabetic or has hypertension.
9. The method of any one of embodiments 1 to 8 wherein the amount is effective to promote osteogenic differentiation.
10. The method of any one of embodiments 1 to 9 wherein the amount is effective to modulate or inhibit one or more proinflammatory cytokines.
11. The method of embodiment 10 wherein the cytokine is IL-8 or IL-6.
12. The method of any one of embodiments 1 to 11 wherein the amount modulates osteoprotegerin (OPG) expression.

13. The method of any one of embodiments 1 to 12 wherein the composition comprises complexes of the isolated miRNA of one or more members of the miR-200 family and a carrier.
14. The method of embodiment 13 wherein the carrier comprises PEI or PLGA.
15. The method of any one of embodiments 1 to 14 wherein one miR-200 family member comprises miR-200c, miR-200a, miR-200b, miR-141 or miR-429.
16. The method of embodiment 15 wherein the miR-200 family member comprises miR-200c.
17. The method of any one of embodiments 1 to 16 wherein one miR-200 family member comprises a nucleic acid sequence with at least 80% nucleic acid sequence identity to one of SEQ ID Nos. 1-3.
18. The method of any one of embodiments 1 to 17 wherein the amount is effective to inhibit cartilage degeneration.
19. A pharmaceutical composition comprising at least one non-naturally occurring polymer comprising an amount of isolated miRNA of one or more members of miR-200 family effective to enhance bone regeneration, inhibit bone loss.
20. The composition of embodiment 19 wherein the non-naturally occurring polymer comprises PEI or PLGA.

REFERENCES

Eke et al., *J. Dent. Res.,* 91:914 (2012).
Papapanou and Tonetti, *Periodontol.* 22:8-21 (2000).
Müller and Ulbrich, *Clin. Oral Investig.* 9:98-104 (2005).
Armas et al., J, Culshaw S, Savarrio L. Treatment of peri-implant diseases: a review of the literature and protocol proposal. *Dent Update.* 472-480 (2013).
Jeffcoat, *Ann. Periodontol.,* 3:312-321 (1998).
Sidiropoulou-Chatzigiannis et al., *J. Int. Acad Periodontol.,* :77-84 (2007).
Khosla et al., *J. Clin. Endocrinol. Metab.* 97:2272-82. (2012).
Darveau, *Nat. Rev. Microbiol.,* 8:481-90 (2010).
Di Benedetto et al., *Clin. Dev. Immunol.,* 2013:503754 (2013).
Hajishengallis et al., *Adv. Exp. Med. Biol.,* 946:69-85 (2012).
Herath et al., *PLoS One,* 8:e58496 (2013).
Graves et al., *J. Oral Microbiol.* 17:3 (2011).
Yang et al., *J. Bone Miner. Res.,* :559-73 (2013).
Lacey et al., *Osteoarthritis Cartilage,* 17:735-42 (2009).
Hikiji et al., *Am. J. Physiol. Endocrinol. Metab,* 278:E1031-7. (2000)
Wang et al., *J. Dent. Res.,* :1003-10 (2012)
Chang et al., *Nat. Med.,* :682-9 (2009)
Chang et al., *Proc. Natl. Acad. Sci. USA,* 9469-74 (2013).
Singh et al., *Autoimmun. Rev.,* :1160-5 (2013).
Plank et al., *Clin. Exp. Allergy,* :981-99 (2013).
Lian et al., *Nat Rev. Endocrinol.,* :212-27 (2012).
Katoh and Katoh, *Int. J. Mol. Med.,* 22:271-5 (2008).
Stoecklin-Wasmer et al., *J. Dent. Res.,* 91:934-40 (2012)
Huang et al., *Stem Cell Res.,* :338-53 (2014).
Rokavec et al., *Mol. Cell,* 45:777-89 (2012).
Wendlandt et al., *Innate Immun.,* :846-55 (2012).
Howe et al., *PLoS One,* 7:e49987. (2012).
Cao et al., *Development,* :3348-59 (2013).
Chuang et al., *PLoS One,* :e95370 (2014).
Holpuch et al., *Pharm. Res.,* 27:1224-36 (2010).
Elangovan et al., *Biomaterials,* 35:737-747 (2014)
Mogensen, *Clin. Microbiol. Rev.,* 22:240-73 (2009)
Borgwardt et al., *Sci. Rep.,* 4:3904 (2014).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

The claims are as follows:

1. A method to prevent, inhibit or treat aveolar bone loss, periodontal bone loss, peri-implantitis, periodontitis, or osteoarthritis, or to enhance bone regeneration, comprising: administering to a mammal an effective amount of a composition comprising isolated miR-200c.

2. The method of claim 1 wherein the mammal is a human, bovine, ovine, caprine, equine, porcine, canine or feline.

3. The method of claim 1 wherein the amount is effective to enhance osseointegration of a dental implant.

4. The method of claim 1 wherein the amount is effective to enhance alveolar bone regeneration.

5. The method of claim 1 wherein the mammal is a diabetic or has hypertension.

6. The method of claim 1 wherein the amount is effective to promote osteogenic differentiation.

7. The method of claim 1 wherein the amount is effective to modulate or inhibit one or more proinflammatory cytokines.

8. The method of embodiment 7 wherein the cytokine is IL-8 or IL-6.

9. The method of claim 1 wherein the amount modulates osteoprotegerin (OPG) expression.

10. The method of claim 1 wherein the composition comprises complexes of the isolated miRNA and a carrier.

11. The method of embodiment 10 wherein the carrier comprises PE or PLGA.

12. The method of claim 1 wherein the composition consists of miR-200c.

13. The method of claim 1 wherein one miR-200 family member comprises a nucleic acid sequence with at least 80% nucleic acid sequence identity to one of SEQ ID Nos. 1-3.

14. The method of claim 1 wherein the amount is effective to inhibit cartilage degeneration.

15. The method of claim 1 wherein aveolar bone loss or periodontal bone loss is prevented, inhibited or treated.

16. The method of claim 1 wherein peri-implantitis, periodontitis, or osteoarthritis is prevented, inhibited or treated.

17. The method of claim 1 wherein bone regeneration is enhanced.

* * * * *

UNITED STATES PATENT AND TRADEMARK OFFICE
CERTIFICATE OF CORRECTION

PATENT NO. : 10,669,543 B2
APPLICATION NO. : 15/543816
DATED : June 2, 2020
INVENTOR(S) : Hong et al.

It is certified that error appears in the above-identified patent and that said Letters Patent is hereby corrected as shown below:

On the Title Page

In item (73), in "Assignee", in Column 1, Line 2, delete "FL" and insert --IA-- therefor In Column 2, under "Other Publications", Line 15, delete "Communicaiton" and insert --Communication-- therefor In item (57), in "Abstract", in Column 2, Lines 1-2, delete "aveolar" and insert --alveolar-- therefor In the Specification In Column 1, Line 56, delete "at" and insert --et-- therefor In Column 1, Line 61, delete "at" and insert --et-- therefor In Column 2, Line 1, delete "at" and insert --et-- therefor In Column 3, Line 2, delete "aveolar" and insert --alveolar-- therefor In Column 4, Line 55, delete "ug)" and insert --µg)-- therefor In Column 4, Line 55, delete "ug)" and insert --µg)-- therefor In Column 5, Line 44, delete "Bar-10 µm." and insert --Bar=10 µm.-- therefor In Column 8, Line 2, delete "TNFα," and insert --TNF-α,-- therefor In Column 12, Line 40, delete "gycolic" and insert --glycolic-- therefor In Column 12, Line 47, delete "pyrollidone," and insert --pyrrollidone,-- therefor Signed and Sealed this
Fifteenth Day of November, 2022

Katherine Kelly Vidal
*Director of the United States Patent and Trademark Office*

CERTIFICATE OF CORRECTION (continued)
U.S. Pat. No. 10,669,543 B2

In Column 13, Line 12, delete "add" and insert --acid-- therefor

In Column 13, Line 32, delete "ethylenamines." and insert --ethyleneamines.-- therefor In Column 15, Line 8, delete "monosterate" and insert --monostearate-- therefor In Column 15, Line 19, delete "day," and insert --clay,-- therefor In Column 15, Line 63, delete "TLR4" and insert --TLR-4-- therefor In Column 16, Line 22, delete "Runx2," and insert --Runx2;-- therefor In Column 17, Line 3, after "point", insert --.--

In Column 17, Line 25, delete "ug/mL)" and insert --µg/mL)-- therefor

In Column 17, Line 64, delete "NIP" and insert --N/P-- therefor

In Column 18, Line 24, delete "NIP" and insert --N/P-- therefor

In Column 20, Line 58, delete "alpha-0.05" and insert --alpha=0.05-- therefor

In Column 21, Line 23, after "OA", insert --.--

In Column 24, Line 51, delete "vector," and insert --vector;-- therefor

In Column 25, Line 61, delete "vive" and insert --*vivo*-- therefor

In Column 26, Line 44, delete "vanes" and insert --varies-- therefor

In Column 29, Line 17, delete "NIP" and insert --N/P-- therefor

In Column 29, Line 50, delete "Alter" and insert --After-- therefor

In Column 29, Line 52, delete "alter" and insert --after-- therefor

In Column 30, Line 20, delete "(ICT)," and insert --(µCT),-- therefor

In Column 30, Line 21, delete "Is" and insert --is-- therefor

In Column 30, Line 58, after "Stemcell", insert --and ScienceCell, respectively. Taqmen probe and primers for real-time PCR and Sybre Green primers analysis were purchased from Invitrogen. Measurements of *ALP* and calcium were made using kits purchased from AnaSpec, Inc. All other chemicals and media were purchased from Invitrogen.--

In Column 31, Line 55, delete "done" and insert --clone-- therefor

CERTIFICATE OF CORRECTION (continued)
U.S. Pat. No. 10,669,543 B2

In Column 37, Line 3, delete "at" and insert --et-- therefor

In Column 37, Line 12, delete "at" and insert --et-- therefor

In Column 38, Line 33, delete "aveolar" and insert --alveolar-- therefor

In the Claims

In Column 45, Line 2, in Claim 1, delete "aveolar" and insert --alveolar-- therefor In Column 46, Line 6, in Claim 11, delete "PE" and insert --PEI-- therefor In Column 46, Line 14, in Claim 15, delete "aveolar" and insert --alveolar-- therefor

SEQUENCE LISTING

```
<160> NUMBER OF SEQ ID NOS: 15

<210> SEQ ID NO 1
<211> LENGTH: 68
<212> TYPE: RNA
<213> ORGANISM: Artificial Sequence
<220> FEATURE:
<223> OTHER INFORMATION: A synthetic RNA

<400> SEQUENCE: 1
cccucgucuu acccagcagu guuuggugc gguugggagu cucuaauacu gccggguaau      60
gauggagg                                                              68

<210> SEQ ID NO 2
<211> LENGTH: 22
<212> TYPE: RNA
<213> ORGANISM: Artificial Sequence
<220> FEATURE:
<223> OTHER INFORMATION: A synthetic RNA

<400> SEQUENCE: 2
cgucuuaccc agcaguguuu gg                                              22

<210> SEQ ID NO 3
<211> LENGTH: 23
```

```
<212> TYPE: RNA
<213> ORGANISM: Artificial Sequence
<220> FEATURE:
<223> OTHER INFORMATION: A synthetic RNA

<400> SEQUENCE: 3
uaauacugcc ggguaaugau gga                                            23

<210> SEQ ID NO 4
<211> LENGTH: 18
<212> TYPE: DNA
<213> ORGANISM: Artificial Sequence
<220> FEATURE:
<223> OTHER INFORMATION: A synthetic primer

<400> SEQUENCE: 4
caacaagacc ctgcccgt                                                  18

<210> SEQ ID NO 5
<211> LENGTH: 20
<212> TYPE: DNA
<213> ORGANISM: Artificial Sequence
<220> FEATURE:
<223> OTHER INFORMATION: A synthetic primer

<400> SEQUENCE: 5
tcccatctgg tacctctccg                                                20

<210> SEQ ID NO 6
<211> LENGTH: 17
<212> TYPE: DNA
<213> ORGANISM: Artificial Sequence
<220> FEATURE:
<223> OTHER INFORMATION: A synthetic primer

<400> SEQUENCE: 6
cttcaaggtg gtagccc                                                   17

<210> SEQ ID NO 7
<211> LENGTH: 22
<212> TYPE: RNA
<213> ORGANISM: Artificial Sequence
<220> FEATURE:
<223> OTHER INFORMATION: A synthetic RNA

<400> SEQUENCE: 7
uaauacugcc gguaaugaug ga                                             22

<210> SEQ ID NO 8
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 8
taccacttga aacattttat gtattag                                        27

<210> SEQ ID NO 9
<211> LENGTH: 23
<212> TYPE: RNA
<213> ORGANISM: Artificial Sequence
<220> FEATURE:
<223> OTHER INFORMATION: A synthetic RNA

<400> SEQUENCE: 9
```
uaauacugcc ggguaaugau gga                    23

<210> SEQ ID NO 10
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 10
tttatttcta agtggaaaaa gtattag                27

<210> SEQ ID NO 11
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 11
atctctacta aaatacaaa aaattag                 27

<210> SEQ ID NO 12
<211> LENGTH: 23
<212> TYPE: RNA
<213> ORGANISM: Artificial Sequence
<220> FEATURE:
<223> OTHER INFORMATION: A synthetic RNE

<400> SEQUENCE: 12
uaauacugcc ggguaaugau gga                    23

<210> SEQ ID NO 13
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 13
tttatgtaac tggctatcta tatttttaa              29

<210> SEQ ID NO 14
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 14
ttctaagtgg aaaactcgta gcca                   24

<210> SEQ ID NO 15
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 15
actccttcag tacaacaaca acaa                   24